United States Patent
Spuhler et al.

(10) Patent No.: US 10,722,880 B2
(45) Date of Patent: Jul. 28, 2020

(54) HYDROPHILIC COATING OF FLUIDIC CHANNELS

(71) Applicant: Cellular Research, Inc., Menlo Park, CA (US)

(72) Inventors: Philipp Spuhler, Menlo Park, CA (US); Sixing Li, Menlo Park, CA (US)

(73) Assignee: Cellular Research, Inc., Menlo Park, CA (US)

( * ) Notice: Subject to any disclaimer, the term of this patent is extended or adjusted under 35 U.S.C. 154(b) by 301 days.

(21) Appl. No.: 15/868,811

(22) Filed: Jan. 11, 2018

(65) Prior Publication Data

US 2018/0200710 A1 Jul. 19, 2018

Related U.S. Application Data

(60) Provisional application No. 62/446,223, filed on Jan. 13, 2017.

(51) Int. Cl.
*B01L 3/00* (2006.01)
*C12N 15/10* (2006.01)
(Continued)

(52) U.S. Cl.
CPC ......... *B01L 3/502* (2013.01); *B01L 3/502746* (2013.01); *B01L 3/502784* (2013.01); *C12N 15/1065* (2013.01); *C12Q 1/6869* (2013.01); *C12Q 1/6874* (2013.01); *G01N 15/1031* (2013.01); *G01N 15/1056* (2013.01); *G01N 15/1484* (2013.01); *B01L 2200/0647* (2013.01); *B01L 2200/0668* (2013.01);
(Continued)

(58) Field of Classification Search
CPC ........... C12N 15/1065; C12N 15/1034; C12N 15/10; C12N 15/09; C12Q 1/6869; C12Q 1/68; B01L 3/502746; B01L 3/502784; B01L 3/502; B01L 3/50
USPC ............................................ 422/503, 500, 50
See application file for complete search history.

(56) References Cited

U.S. PATENT DOCUMENTS 4,510,244 A 4/1985 Parks et al.
4,725,536 A 2/1988 Fritsch et al.
(Continued)

FOREIGN PATENT DOCUMENTS

DE 102008025656 12/2009
EP 0 799 897 10/1997
(Continued)

OTHER PUBLICATIONS

Achim et al., May 2015, High-throughput spatial mapping of single-cell RNA-seq data to tissue of origin. Nature Biotechnology, 33(5):503-511.
(Continued)

*Primary Examiner* — Christine T Mui
(74) *Attorney, Agent, or Firm* — Kathleen Y. Rao; Bret E. Field; Bozicevic, Field & Francis LLP

(57) ABSTRACT

Disclosed herein are methods, devices, and systems for efficient loading and retrieval of particles. In some embodiments, a fluidic channel of a flowcell comprises a ceiling, a first sidewall, and a bottom, wherein the contact angle of the ceiling is at least 10 degrees smaller than the contact angle of the first sidewall, and wherein the bottom of the fluidic channel comprises a substrate that comprises a plurality of microwells.

30 Claims, 50 Drawing Sheets

(51) Int. Cl.
*G01N 15/10* (2006.01)
*C12Q 1/6874* (2018.01)
*G01N 15/14* (2006.01)
*C12Q 1/6869* (2018.01)
*C12N 15/09* (2006.01)
*C12Q 1/68* (2018.01)

(52) U.S. Cl.
CPC ..... *B01L 2200/14* (2013.01); *B01L 2300/088* (2013.01); *B01L 2300/0816* (2013.01); *B01L 2300/0851* (2013.01); *B01L 2300/0858* (2013.01); *B01L 2300/0864* (2013.01); *B01L 2300/0877* (2013.01); *B01L 2300/0893* (2013.01); *B01L 2300/12* (2013.01); *B01L 2300/161* (2013.01); *B01L 2300/165* (2013.01); *B01L 2400/0406* (2013.01); *B01L 2400/088* (2013.01); *G01N 2015/1006* (2013.01); *G01N 2015/1081* (2013.01)

(56) References Cited

U.S. PATENT DOCUMENTS

| | | | |
|---|---|---|---|
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchick et al. |
| 5,962,272 A | 10/1999 | Chenchick et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,663,077 B2 | 11/2003 | Brenner |
| 6,753,147 B2 | 6/2004 | Vogelstein et al. |
| 6,787,308 B2 | 9/2004 | Balasubramanian et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,223,364 B1 * | 5/2007 | Johnston ............... B01L 3/5023 422/502 |
| 7,393,665 B2 | 7/2008 | Brenner |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,645 B2 | 2/2017 | Fan et al. |
| 9,567,646 B2 | 2/2017 | Fan et al. |
| 9,582,877 B2 | 2/2017 | Fu et al. |
| 9,598,736 B2 | 3/2017 | Fan et al. |
| 9,637,799 B2 | 5/2017 | Fan et al. |
| 9,708,659 B2 | 7/2017 | Fodor et al. |
| 9,787,810 B1 | 8/2017 | Fodor et al. |
| 9,816,137 B2 | 11/2017 | Fodor et al. |
| 9,845,502 B2 | 12/2017 | Fodor et al. |
| 9,905,005 B2 | 2/2018 | Fu et al. |
| 9,951,386 B2 | 4/2018 | Hindson et al. |
| 10,002,316 B2 | 6/2018 | Fodor et al. |
| 10,047,394 B2 | 8/2018 | Fodor et al. |
| 10,059,991 B2 | 8/2018 | Fodor et al. |
| 2002/0065609 A1 | 5/2002 | Ashby |
| 2002/0072058 A1 | 6/2002 | Voelker et al. |

(56) References Cited

U.S. PATENT DOCUMENTS

| | | |
|---|---|---|
| 2002/0168665 A1 | 11/2002 | Okawa |
| 2002/0187480 A1 | 12/2002 | Brandon |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0047769 A1 | 3/2004 | Tanaami |
| 2004/0096368 A1 | 5/2004 | Davis |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0053952 A1 | 3/2005 | Hong et al. |
| 2005/0105077 A1 | 5/2005 | Padmanabhan |
| 2005/0170373 A1 | 8/2005 | Monforte |
| 2005/0250147 A1 | 11/2005 | Macevicz |
| 2006/0002624 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2006/0280352 A1 | 12/2006 | Muschler |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0105090 A1 | 5/2007 | Cassidy et al. |
| 2007/0117121 A1 | 5/2007 | Hutchison |
| 2007/0117134 A1 | 5/2007 | Kou |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0220385 A1 | 9/2009 | Brown |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal |
| 2009/0298709 A1 | 12/2009 | Ma |
| 2010/0069250 A1 | 3/2010 | White, III |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0159533 A1 | 6/2010 | Lipson et al. |
| 2010/0255471 A1 | 10/2010 | Clarke |
| 2010/0267028 A1 | 10/2010 | Clarke |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0014977 A1 | 1/2012 | Furihata et al. |
| 2012/0034607 A1 | 2/2012 | Rothberg |
| 2012/0040843 A1 | 2/2012 | Ducree et al. |
| 2012/0045368 A1* | 2/2012 | Hinz .................. G01N 27/4148 422/69 |
| 2012/0045844 A1 | 2/2012 | Rothberg et al. |
| 2012/0065081 A1 | 3/2012 | Chee |
| 2012/0071331 A1 | 3/2012 | Casbon |
| 2012/0149603 A1 | 6/2012 | Cooney |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0147860 A1 | 5/2014 | Kaduchak |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0206079 A1 | 7/2014 | Malinoski |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0066385 A1 | 3/2015 | Schnall-levin et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0298091 A1 | 10/2015 | Weitz |
| 2015/0307874 A1 | 10/2015 | Jaitin |
| 2015/0376609 A1 | 12/2015 | Hindson et al. |
| 2016/0026758 A1 | 1/2016 | Jabara et al. |
| 2016/0122753 A1 | 5/2016 | Mikkelsen |

(56) References Cited

U.S. PATENT DOCUMENTS

2016/0244628 A1 8/2016 Mason
2016/0257993 A1 9/2016 Fu et al.
2016/0289669 A1 10/2016 Fan et al.
2016/0289740 A1 10/2016 Fu et al.
2016/0312276 A1 10/2016 Fu et al.
2016/0320720 A1 11/2016 Fan et al.
2016/0376648 A1 12/2016 Fodor et al.
2017/0073730 A1 3/2017 Betts et al.
2017/0314067 A1 11/2017 Shum et al.
2017/0342405 A1 11/2017 Fu et al.
2017/0342465 A1 11/2017 Shum et al.
2017/0344866 A1 11/2017 Fan et al.
2018/0002764 A1 1/2018 Fan et al.
2018/0037942 A1 2/2018 Fu et al.

FOREIGN PATENT DOCUMENTS

| EP | 1 473 080 | 11/2004 |
|---|---|---|
| EP | 1 647 600 | 4/2006 |
| EP | 1 845 160 | 10/2007 |
| EP | 2 623 613 | 8/2013 |
| EP | 2 605 769 | 11/2014 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/059355 | 8/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 07/087310 | 8/2007 |
| WO | WO 07/087312 | 8/2007 |
| WO | WO 07/147079 | 12/2007 |
| WO | WO 08/096318 | 8/2008 |
| WO | WO 08/147428 | 12/2008 |
| WO | WO 08/150432 | 12/2008 |
| WO | WO 09/148560 | 12/2009 |
| WO | WO 09/152928 | 12/2009 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/148525 | 10/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 15/103339 | 7/2015 |
| WO | WO 15/134787 | 9/2015 |
| WO | WO 15/200869 | 12/2015 |
| WO | WO 16/138500 | 9/2016 |

OTHER PUBLICATIONS

Algae, Wikipedia.org, accessed Mar. 4, 2016, 20 pp.
Alkan et al., Oct. 2009, Personalized copy number and segmental duplication maps using next-generation sequencing. Nat Genet., 41(10):1061-1067.
Anderson, Feb. 11, 2014, Study describes RNA sequencing applications for molecular indexing methods, genomeweb.com, 5 pp.
ANSORGE, 2009, Next-generation DNA sequencing techniques. New Biotechnology, 25(4):195-203.
Applied Biosystems, Apr. 2008, SOLiD™ System Barcoding, Application Note, 4 pp.
Archaea, Wikipedia.org, accessed May 11, 2016, 26 pp.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bogdanova et al., Jan. 2008, Normalization of full-length enriched cDNA, Molecular Biosystems, 4(3):205-212.
Bonaldo et al., Sep. 1996, Normalization and subtraction: two approaches to facilitate gene discovery. Genome Res., 6(9):791-806.
Bontoux et al, "Integrating whole transcriptome assays on a lab-on-a-chip for single cell gene profiling", Lab on a Chip, (2008) vol. 8, No. 3, pp. 443-450.
Brady et al., "Construction of cDNA libraries form single cells", Methods in Enzymology, Academic Press, US, (1993) vol. 225, doi:10.1016/0076-6879(93)25039-5, ISSN 0076-6879, pp. 611-623.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, in vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.

(56) References Cited

OTHER PUBLICATIONS

Brodin et al., 2015, Challenges with using primer IDs to improve accuracy of next generation sequencing, 19(3):1-12.
Buschmann et al., Aug. 7, 2014, Enhancing the detection of barcoded reads in high throughput DNA sequencing DNA by controlling the false discovery rate, BMC Bioinformatics, 15(1):264.
Butkus, Feb. 6, 2014, Cellular research set to launch first gene expression platform using 'molecular indexing' technology, genomeweb.com, 5 pp.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification, Nucleic Acids Res., 16(23):11141-11156.
Chang et al., Aug. 2002, Detection of allelic imbalance in ascitic supernatant by digital single nucleotide polymorphism analysis, Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Clontech Laboratories, Inc., May 15, 2007, Super SMART™ PCR cDNA Synthesis Kit User Manual, 39 pp.
Cloonan et al., "Stem cell transcriptome profiling via massive-scale mRNA sequencing", Nature Methods, (Jul. 2008) vol. 5, No. 7, pp. 613-619.
Costa et al., Aug. 22, 2012, Single-tube nested real-time PCR as a new highly sensitive approach to trace hazelnut, J. Agric Food Chem, 60(33):8103-8110.
Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Custom Antibody Services, Precision Antibody, accessed Apr. 16, 2014, 2 pp.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.

De Saizieu et al., 1998, Bacterial transcript imaging by hybridization of total RNA to oligonucleotide arrays. Nature Biotechnology, 16:45-48.
Di Carlo et al., Dec. 1, 2008, Dynamic single-cell analysis for quantitative biology, Analytical Chemistry, 78(23):7918-7925.
Dirks et al., Oct. 26, 2004, Triggered amplification by hybridization chain reaction., Proc Nat Acad Sci U S A, 101(43), 15275-15278.
Eberwine et al., "Analysis of gene expression in single live neurons", Proc. Natl. Acad. Sci. USA, (Apr. 1992) vol. 89, No. 7, pp. 3010-3014.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Feb. 6, 2015, Combinatorial labeling of single cells for gene expression cytometry. Science, 347(6222):1258367-8.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pages.
Feldhaus et al., Jan. 15, 2000, Oligonucleotide-conjugated beads for transdominant genetic experiments, Nucleic Acids Res., 28(2):534-543.
Fish, Wikipedia.org, accessed Nov. 2, 2014, 11 pp.
Fox-Walsh et al., Oct. 2011, A multiplex RNA-seq strategy to profile poly(A+) RNA: application to analysis of transcription response and 3' end formation., Genomics, 98(4),266-271.
Fu et al., Marcy 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Fungus, Wikipedia.org, accessed Jun. 3, 2013, 28 pp.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2),1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harbers, "The current status of cDNA cloning", Genomics, (2008) vol. 91, No. 3, pp. 232-242.
Harrington et al., 2009, Cross-sectional characterization of HIV-1 env compartmentalization in cerebrospinal fluid over the full disease course, AIDS, 23(8) 907-915.
Hartmann, "Gene expression profiling of single cells on large-scale oligonucleotide arrays", Nucleic Acids Research, (Oct. 2006) vol. 34, No. 21, p. e143.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.

(56) References Cited

OTHER PUBLICATIONS

Hiatt et al., Feb. 2010, Parallel, tag-directed assembly of locally derived short sequence reads, Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
How many species of bacteria are there? Wisegeek.org, accessed Jan. 21, 2014, 2 pp.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al, "Highly multiplexed and strand specific single-cell RNA 5' end sequencing", Nature Protocols, (2012) vol. 7, No. 5, pp. 813-828.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2)163-168.
Jabara et al., Dec. 3. 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Junker et al., May 21, 2015, Single-cell transcriptomics enters the age of mass production, Molecular Cell. 58:563-564.
Kanagawa, 2003, Bias and artifacts in multitemplate polymerase chain reactions (PCR), Journal of Bioscience and Bioengineering, 96(4):317-323.
Karrer et al., "In situ isolation of mRNA from individual plant cells: creation of cell-specific cDNA libraries,", Proc. Natl. Acad. Sci. USA, (Apr. 1995) vol. 92, No. 9, pp. 3814-3618.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers, Nature Methods, 9(1):72-76.
Klein et al., May 21, 2015, Droplet barcoding for single-cell transcriptomics applied to embryonic stem cells, Cell, 161:1187-1201.
Ko et al., "RNA-conjugated template-switching RT-PCR method for generating an *Escherichia coli* cDNA library for small RNAs", Journal of Microbiological Methods, (2006) vol. 64, No. 3, pp. 297-304.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.

Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kurimoto et al, "Global single-cell cDNA amplification to provide a template for representative high-density oligonucleotide microarray analysis", Nature Protocols, (2007) vol. 2, No. 3, pp. 739-752.
Kurimoto et al., Mar. 17, 2006, An improved single-cell cDNA amplification method for efficient high-density oligonucleotide microarray analysis, Nucleic Acids Res., 34(5):e42.
Lamble et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.
List of sequenced bacterial genomes, Wikipedia.org, accessed Jan. 24, 2014, 57 pp.
Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science; 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Maeda et al., "Development of a DNA barcode tagging method for monitoring dynamic changes in gene expression by using an ultra high-throughput sequencer", BioTechniques, (Jul. 2008), vol. 45, No. 1, pp. 95-97.
Makrigiorgos et al., Sep. 2002, A PCR-Based amplification method retaining quantities difference between two complex genomes. Nature Biotech, 20(9):936-939.
Mammal, Wikipedia.org, accessed Sep. 22, 2011, 16 pp.
Marcus et al., 2006, Microfluidic single-cell mRNA isolation and analysis, Ana. Chem. 78:3084-3089.
Mardis, "Next-generation DNA sequencing methods", Annu. Rev. Genomics Hum. Genet., (2008) vol. 9, pp. 387-402.
Marguerat et al, "Next-generation sequencing: applications beyond genomes", Biochemical Society Transactions, (2008) vol. 36, No. 5, pp. 1091-1096.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.
McCloskey et al., Dec. 2007, Encoding PCR products with batch-stamps and barcodes. Biochem Genet, 45(11-12):761-767.
Medvedev et al., Nov. 2010, Detecting copy number variation with mated short reads. Genome Res. 20(11):1613-1622.

(56) References Cited

OTHER PUBLICATIONS

Mei et al., Mar. 22, 2010, Identification of recurrent regions of Copy-Number Variants across multiple individuals. BMC Bioinformatics. 11:147.

Merriam-Webster, definition of associate,: http://www.merriam-webster.com/dictionary/associate, accessed Apr. 5, 2016.

Meyer et al., "Parallel tagged sequencing on the 454 platform", Nature Protocols, (2008) vol. 3, No. 2, pp. 267-278.

Miller et al., 2006, Directed evolution by in vitro compartmentalization, Nature Methods, 3:561-570.

Miner et al, 2004, Molecular barcodes detect redundancy and contamination in hairpin-bisulfite PCR, Nucleic Acids Research, 32(17):e135.

Mortazavi et al., 2008, Mapping and quantifying mammalian transcriptornes by RNA-Seq. Nat. Methods. 5:621-628.

Murinae, Wikipedia.org, accessed Mar. 18, 2013, 21 pp.

Nadai et al., 2008, Protocol for nearly full-length sequencing of HIV-1 RNA from plasma, PLoS ONE, 3(1):e1420.

Nagai et al., 2001, Development of a microchamber array for picoleter PCR, Anal. Chem., 73:1043-1047.

Navin et al., 2015, The first five years of single-cell cancer genomics and beyond, Genome Research, 25(10):1499-1507.

Newell et al., Jan. 27, 2012, Cytometry by time-of-flight shows combinatorial cytokine expression and virus-specific cell niches within a continuum of CD8+ T cell phenotypes. Immunity. 36(1):142-152.

Novak et al., Jan. 20, 2011, Single-cell multiplex gene detection and sequencing with microfluidically generated agarose emulsions, Angew Chem Int Ed Engl., 50(2):390-395.

Ogino et al., Nov. 2002, Quantification of PCR bias caused by a single nucleotide polymorphism in SMN gene dosage analysis. J Mol Diagn. 4(4):185-190.

Ozkumur et al., Apr. 3, 2013, Inertial focusing for tumor antigen-dependent and -independent sorting of rare circulating tumor cells, Sci Transl Med, 5(179):1-20.

Parameswaran et al., 2007, A pyrosequencing-tailored nucleotide barcode design unveils opportunities for large-scale sample multiplexing. Nucleic Acids Res. 35(19):e130.

Park et al., May 2010, Discovery of common Asian copy number variants using integrated high-resolution array CGH and massively parallel DNA sequencing. Nat Genet. 42(5):400-405.

Patanjali et al., Mar. 1991, Construction of a uniform-abundance (normalized) CNDA library, Proceedings of the National Academy of Sciences, 88(5):1943-1947.

Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.

Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.

Picelli et al., Jul. 30, 2014, Tn5 transposase and tagmentation procedures for massively scaled sequencing projects, Genome Research 24(12):2033-2040.

Pihlak et al., 2008, Rapid genome sequencing with short universal tiling probes. Nature Biotechnology, 26:676-684.

Pinkel et al., 2005, Comparative Genomic Hybridization. Annual Review of Genomics and Human Genetics, 6:331-354.

Plant, Wikipedia.org, accessed Aug. 28, 2015, 14 pp.

Pleasance et al., Jan. 14, 2010, A small-cell lung cancer genome with complex signatures of tobacco exposure. Nature. 463(7278)184-190.

Plessy et al., Feb. 2013; Population transcriptomics with single-cell resolution: a new field made possible by microfluidics: a technology for high throughput transcript counting and data-driven definition of cell types, Bioessays, 35(2):131-140.

Protozoa, Wikipedia.org, accessed May 11, 2016, 10 pp.

Qiu et al., Oct. 2003, DNA sequence-based "bar codes" for tracking the origins of expressed sequence tags from a maize cDNA library constructed using multiple mRNA sources. Plant Physiol. 133(2):475-481.

Rajeevan et al., Oct. 2003, Global amplification of sense RNA: a novel method to replicate and archive mRNA for gene expression analysis, Genomics, 82(4):491-497.

Roche Diagnostics GmbH, 2006, Genome Sequencer 20 System: First to the Finish (product brochure), 40 pp.

Sasagawa et al., 2013, Quartz-Seq: a highly reproducible and sensitive single-cell RNA sequencing method, reveals non-genetic gene-expression heterogeneity. Genome Biology, 14:R31.

Sasuga et al., Dec. 2008, Single-cell chemical lysis method for analyses of intracellular molecules using an array of picoliter-scale microwells, Anal Chem, 80(23):9141-9149.

Satija et al., May 2015, Spatial reconstruction of single-cell gene expression data. Nature Biotechnology, 33(5):495-508.

Schmitt et al., Sep. 4, 2012, Detection of ultra-rare mutations by next-generation sequencing. Proc Natl Acad Sci U S A. 109(36):14508-14513.

Sebat et al., 2004, Large-Scale Copy Number Polymorphism in the Human Genome. Science, 305:525-528.

Shalek et al., Jun. 13, 2013, Single-cell transcriptomics reveals bimodality in expression and splicing in immune cells. Nature. 498(7453):236-240.

Shendure et al., "Next-generation DNA sequencing", Nature Biotechnology, (Oct. 2008) vol. 26, No. 10, pp. 1135-1145.

Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.

Shoemaker et al., 1996, Quantitative phenotypic analysis of yeast deletion mutants using a highly parallel molecular bar-coding strategy. Nature Genetics, 14:450-456.

Simpson et al., Feb. 15, 2010, Copy Number variant detection in inbred strains from short read sequence data. Bioinformatics. 26(4):565-567.

Smith et al., 2010, Highly-multiplexed barcode sequencing: an efficient method for parallel analysis of pooled samples, Nucleic Acids Research, 38(13):e142.

Sommer et al., Nov. 16, 1989, Minimal homology requirements for PCR primers, Nucleic Acids Research, 17(16):6749.

Song et al., 2013, Design rules for size-based cell sorting and sheathless cell focusing by hydrophoresis, Journal of Chromatography A, 1302:191-196.

Soumillon et al., Mar. 5, 2014, Characterization of directed differentiation by high-throughput single-cell RNA-Seq, bioRxiv preprint, http://biorxiv.org/content/early/2014/03105/003236.full.pdf, 13 pp.

Speicher et al., Oct. 2005, The new cytogenetics: blurring the boundaries with molecular biology, Nature Reviews Genetics, 6(10):782-792.

Stratagene 1998 Catalog, Gene Characterization Kits, p. 39.

Subkhankulova et al., "Comparative evaluation of linear and exponential amplification techniques for expression profiling at the single cell level", Genome Biology, (Mar. 2006) vol. 7, No. R18, pp. 1-16.

Takahashi et al., Mar. 2006, Novel technique of quantitative nested real-time PCR assay for *Mycobacterium* tuberculosis DNA, Journal of Clinical Microbiology, 44(3)1029-1039.

Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.

Tang et al, "RNA-Seq analysis to capture the transcriptome landscape of a single cell", Nature Protocols, (2010) vol. 5, No. 3, pp. 516-535.

Taudien et al., Apr. 19, 2010, Haplotyping and copy number estimation of the highly polymorphic human beta-defensin locus on 8p23 by 454 amplicon sequencing. BMC Genomics. 11:252.

The Tibbs Times, UNC bioscience newsletter, Apr. 2010, 17 pp.

Tomaz et al., Aug. 2010, Differential methylation as a cause of allele dropout at the imprinted GNAS locus. Genet Test Mol Biomarkers. 14(4):455-460.

(56) References Cited

OTHER PUBLICATIONS

Treutlein et al., May 15, 2014, Reconstructing lineage hierarchies of the distal lung epithelium using single-cell RNA-seq. Nature. 509(7500):371-375.
Vandesompele et al., Jun. 18, 2002, Accurate normalization of real-time quantitative RT-PCR data by geometric averaging of multiple internal control genes, Genome Biology, 3(7).
Velculescu et al., 1995, Serial Analysis of Gene Expression. Science, 270:484-487.
Velculescu et al., 1997, Characterization of the Yeast Transcriptome. Cell, 88:243-251.
Virus, Wikipedia.org, accessed Nov. 24, 2012, 34 pp.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for tanscriptomics. Nature Reviews Genetics, 10:57-63.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weiner et al., Apr. 2008, Kits and their unique role in molecular biology: a brief retrospective, BioTechniques, 44:701-704.
White et al., Aug. 23, 2011, High-throughput microfluidic single-cell RT-gPCR, PNAS, 108(34):13999-14004.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage, Genome Res. 19(9):1586-1592.
Zhang et al., Jun. 19, 2012, DNA-based hybridization chain reaction for amplified bioeiectronic signal and ultrasensitive detection of proteins. Anal Chem., 84(12)5392-5399.
Zhang et al., Mar. 20, 2011, The Impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion, Nature Biotechnology, 19:78-81.
Zhu et al., "Reverse transcriptase template switching: a SMART approach for full-length cDNA library construction.", BioTechniques, (Apr. 2001) vol. 30, No. 4, pp. 892-897.
Office Action dated Sep. 8, 2017 in U.S. Appl. No. 15/046,225.
Office Action dated May 3, 2018 in U.S. Appl. No. 15/046,225.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office action dated Jan. 9, 2018 in U.S. Appl. No. 15/217,896.
Office action dated Jan. 12, 2016 in U.S. Appl. No. 15/217,886.
Office action dated Jul. 20, 2018 in U.S. Appl. No. 15/217,886.
Office Action dated Oct. 11, 2016 in U.S. Appl. No. 15/224,460.
Office Action dated May 8, 2017 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
Office Action dated Jul. 28, 2017 in U.S. Appl. No. 14/975,441.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. App. No. 14/381,488.
Office Action dated Feb. 13, 2017 in U.S. Appl. No. 14/381,488.
Office Action dated Jun. 7, 2017 in U.S. App. No. 14/381,488.
Office Action dated Nov. 16, 2017 in U.S. Appl. No. 14/381,488.
Office Action dated May 10, 2018 in U.S. Appl. No. 14/381,488.
International Search Report and Written Opinion dated Sep. 6, 2013 in PCT/US13/028103.
Examination Report No. 1 for standard patent application, dated Oct. 24, 2017, Australian patent application No. 2013226081.
Office Action dated Feb. 17, 2017 in Canadian patent application No. 2,865,575.
Office Action dated Feb. 15, 2018 in Canadian patent application No. 2,865,575.
Office Action dated Jun. 6, 2016 in Chinese patent application No. 201380022137.9.
Office Action dated Dec. 27, 2016 in Chinese patent application No. 201380022187.9.
Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4,.
Extended European Search Report dated Feb. 8, 2018 in patent application No. 17202409.3.

(56) References Cited

OTHER PUBLICATIONS

Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1406829.8.
Official Action dated Dec. 28, 2016 in Japanese patent application No. 2014-558975.
Final Decision dated Aug. 30, 2017 in Japanese patent application No. 2014-558975.
Notice of Reasons for Rejection dated Apr. 2, 2018 in Japanese patent application No. 2014-558975.
Search Report and Written Opinion dated Mar. 1, 2016 in Singapore patent application No. 11201405274W.
Written Opinion dated May 26, 2017 in Singapore patent application No. 11201405274W.
International search report and written opinion dated Aug. 16, 2013 for PCT/US2013/027891.
Extended European Search Report dated Dec. 15, 2015 in European patent application No. 13754428.4.
Examination Report dated Mar. 16, 2018 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
International Search Report and Written Opinion dated Feb. 3, 2015 in PCT/US/14/053301.
Examination Report No. 1 for standard patent application, dated Jul. 20, 2018 Australian patent application No. 2014312208.
Examination Report dated Apr. 10, 2017 in European patent application No. 14761937.3.
Examination Report dated Oct. 10, 2017 in European patent application No. 14761937.3.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Combined Search and Examination Report dated Feb. 21, 2017 in GB patent application No. 1609740.4.
Examination Report dated Jan. 3, 2018 in GB patent application No. 1609740.4.
Third Party Observation dated Jun. 14, 2018 in Japanese patent application No. 2016-537867.
Official Action dated Jul. 30, 2018 in Japanese patent application No. 2016-537867.
Office Action dated May 13, 2016 in U.S. Appl. No. 14/508,911.
Office Action dated Mar. 24, 2017 in U.S. Appl. No. 15/409,355.
Office Action dated Oct. 16, 2017 in U.S. Appl. No. 15/409,355.
International search report and written opinion dated Dec. 19, 2014 for PCT Application No. US2014/059542.
First Office Action dated Dec. 19, 2017 in Chinese patent application No. 201480061859.1.
Office Action dated Jul. 25, 2018 in U.S. Appl. No. 15/108,268.
Office Action dated Nov. 9, 2017 in U.S. Appl. No. 15/004,618.
Office Action dated Jul. 5, 2016 in U.S. Appl. No. 15/004,618.
International Search Report and Written Opinion dated Jun. 20, 2016 in PCT/US16/14612.
Extended European Search Report dated Jun. 11, 2018 in European patent application No. 16740872.3.
Office Action dated Jan. 19, 2017 in U.S. Appl. No. 15/055,445.
Office Action dated Nov. 1, 2017 in U.S. Appl. No. 15/667,125.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.
Office Action dated Sep. 8, 2017 in U.S. Appl. No. 15/134,967.
International Search Report and Written Opinion dated Sep. 28, 2016 in PCT/US16/028694.
International Search Report and Written Opinion dated Sep. 27, 2016 in PCT/US16/034473.
International Search Report and Written Opinion dated Jan. 31, 2017 in PCT/US16/050694.
Office Action dated Mar. 8, 2018 in U.S. Appl. No. 15/608,780.
International Search Report and Written Opinion dated Sep. 8, 2017 in PCT/US2017/030097.
International Search Report and Written Opinion dated Aug. 7, 2017 in PCT/US2017/034576.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.
Statement of Opposition of Strawman Limited filed against European Patent No. EP2414548B1 dated Jul. 19, 2016.
Statement of Opposition filed against European Patent No. EP2414548B1 dated Jul. 26, 2016.
Statement of Opposition filed against European Patent No. EP2414548B1 dated Jul. 21, 2016.
Submission dated Jan. 15, 2018 by Strawman Limited in preparation for upcoming oral-proceedings in opposition against European Patent No. EP2414548B1.
Submission dated Jan. 15, 2018 by Vossius & Partner in preparation for upcoming oral proceedings in opposition against European Patent No. EP2414548B1.
Third-Party Pre-Issuance Submission filed on Jun. 16, 2018 for U.S. Appl. No. 15/847,752.
Third-Party Pre-Issuance Submission filed on Jun. 6, 2018 for U.S. Appl. No. 15/847,752.
Third-Party Pre-Issuance Submission filed on May 21, 2018 for U.S. Appl. No. 15/847,752.

\* cited by examiner

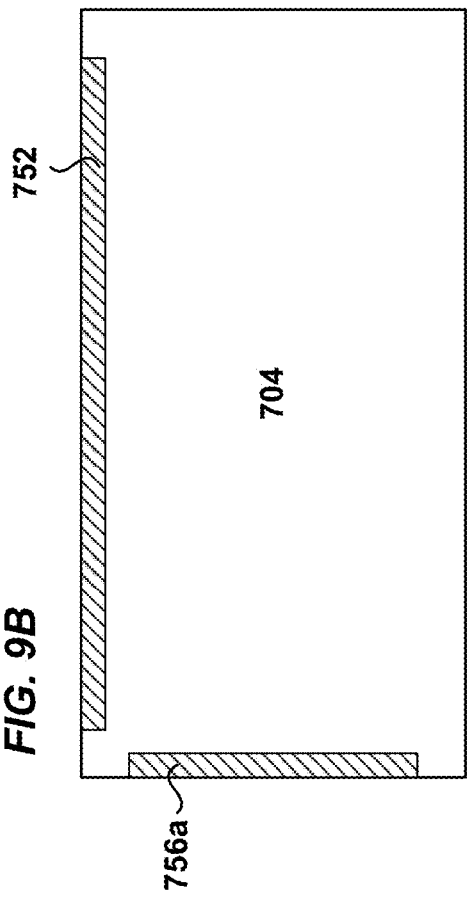
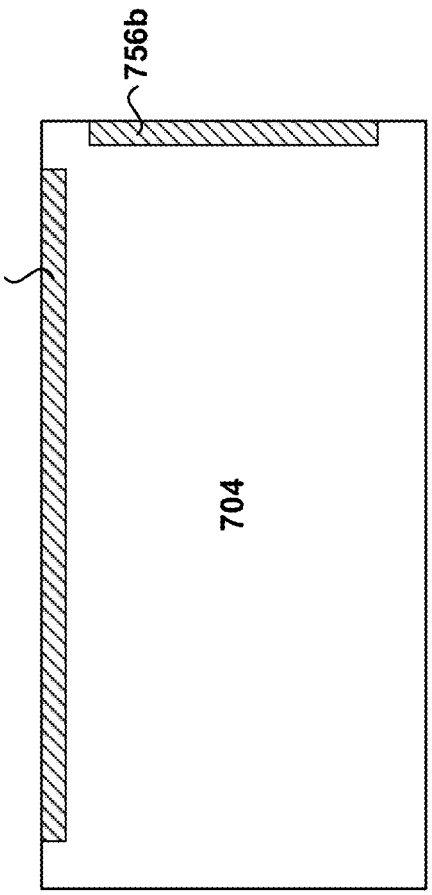
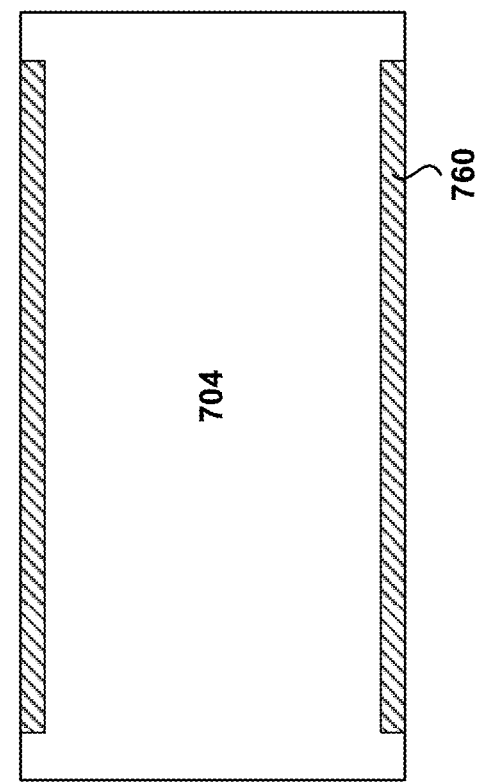

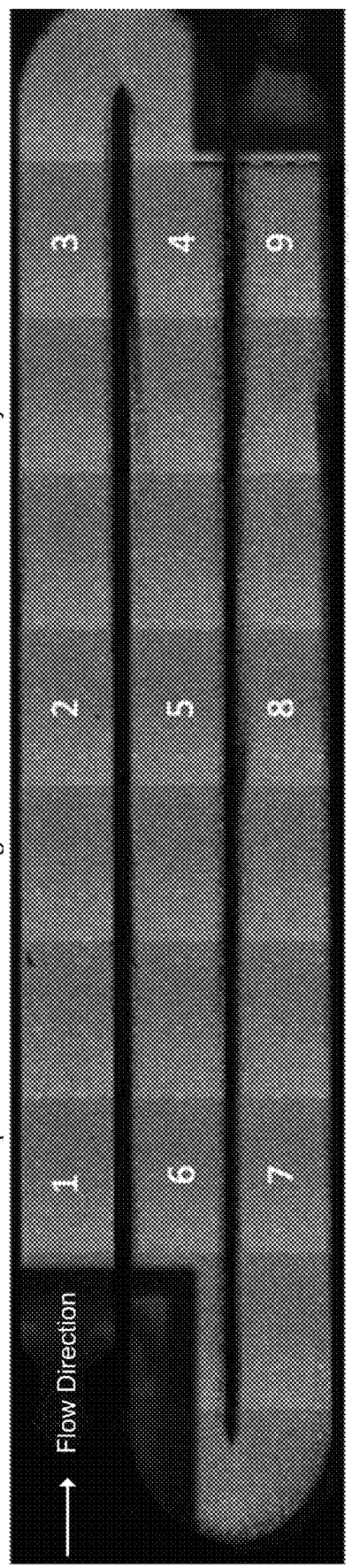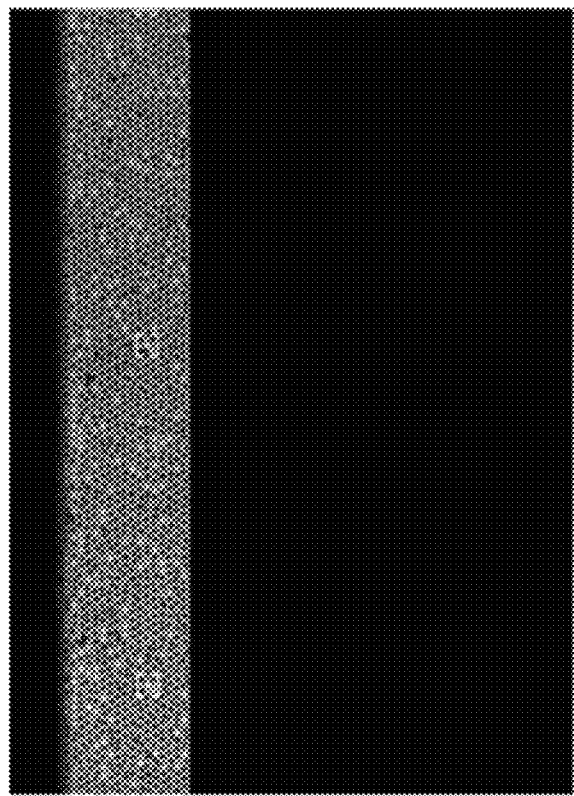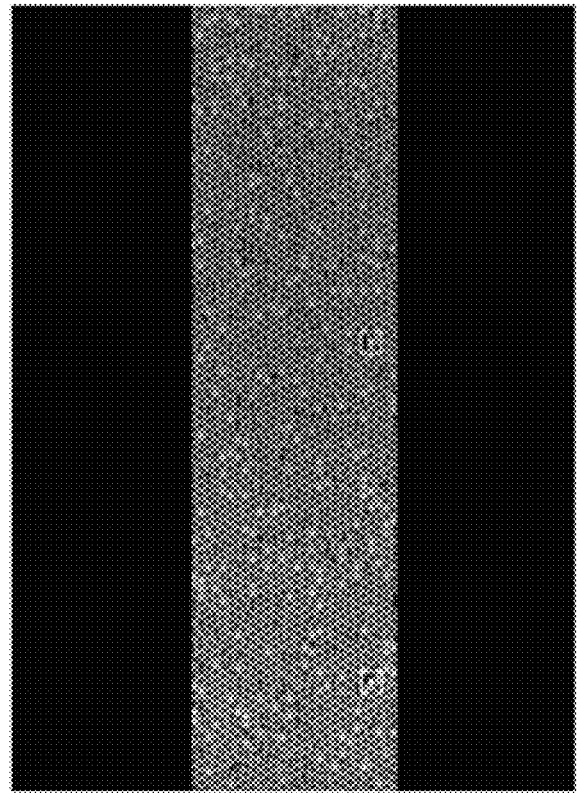
FIG. 11A Hydrophilic Coating on Ceiling and Sidewalls: Incomplete Air Displacement Resulted in High Bead Doublets at Flowcell Boundary
FIG. 11B Center
FIG. 11C Boundary

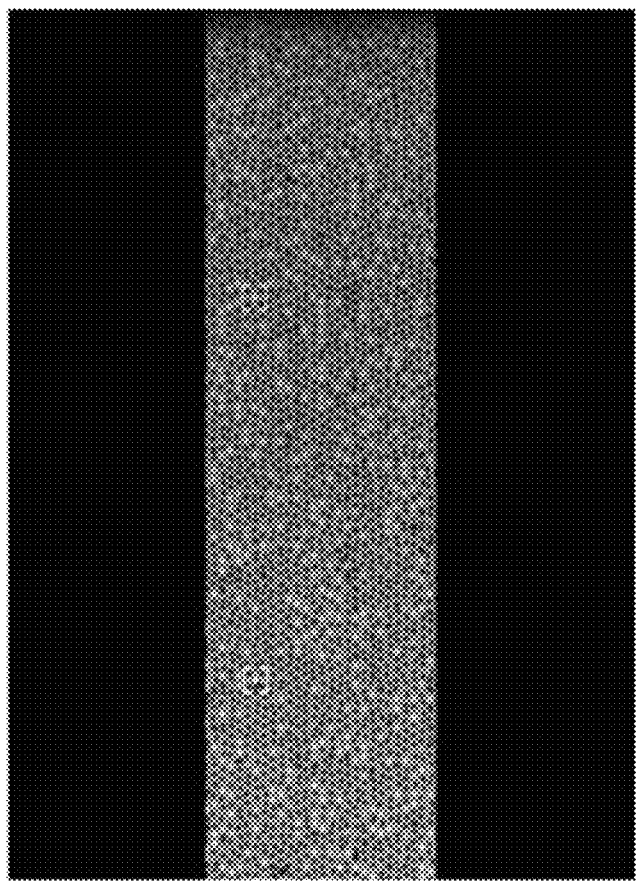
FIG. 11D Center
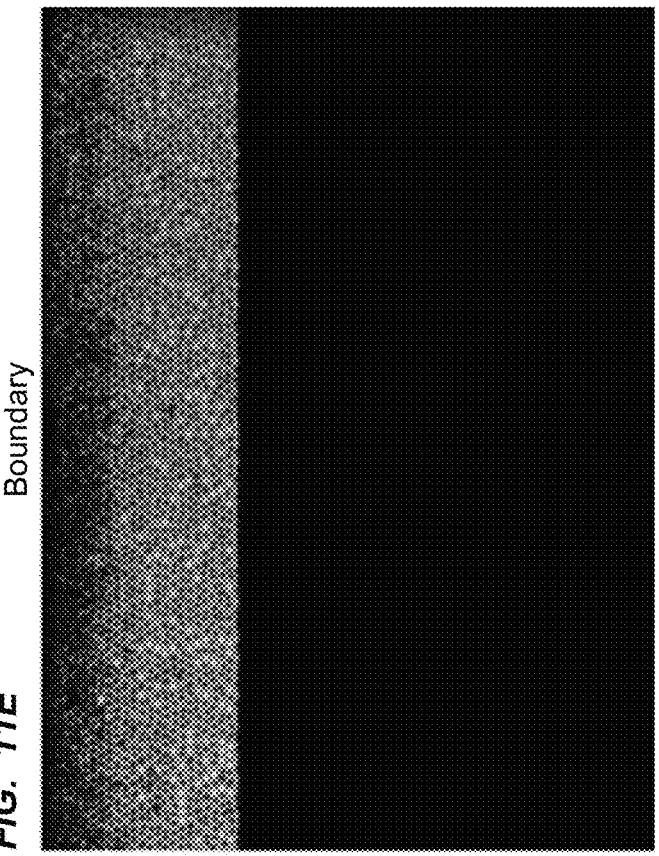
FIG. 11E Boundary

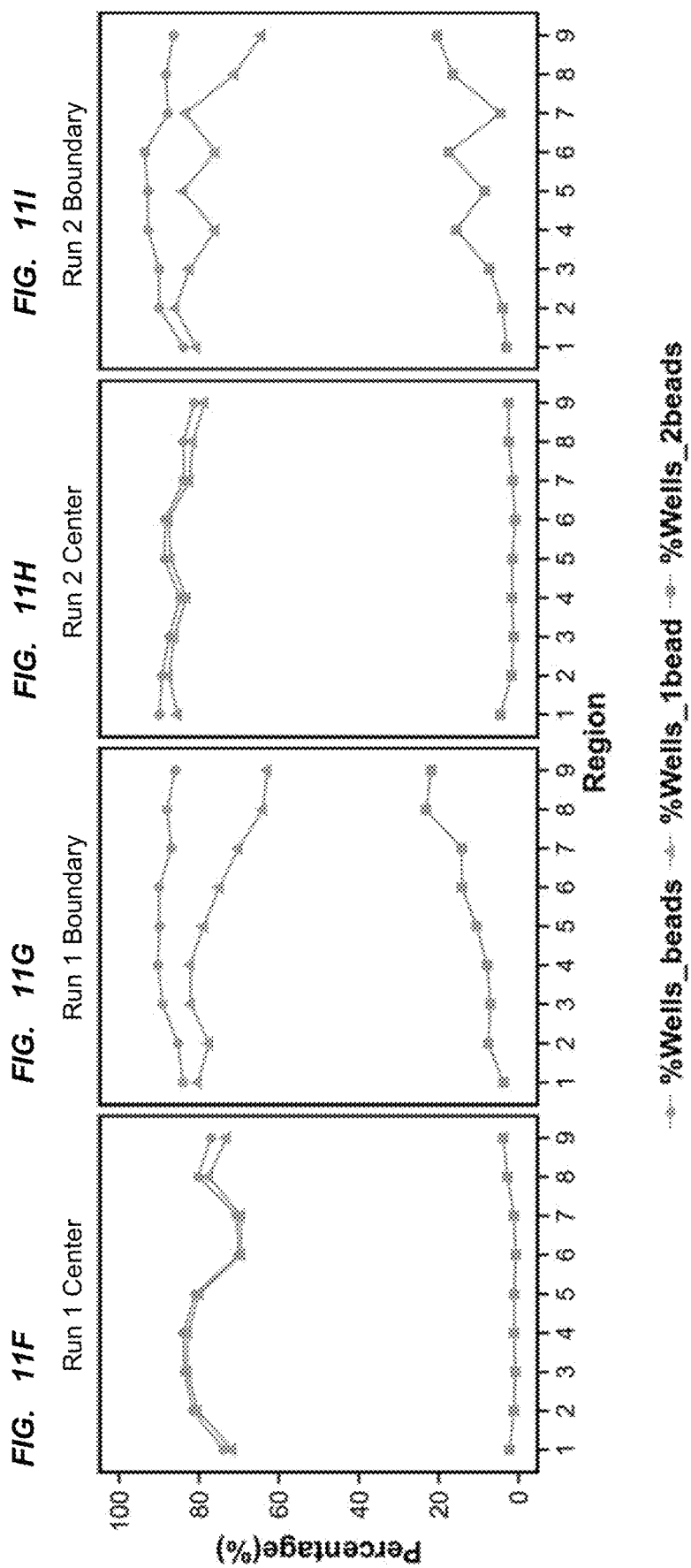

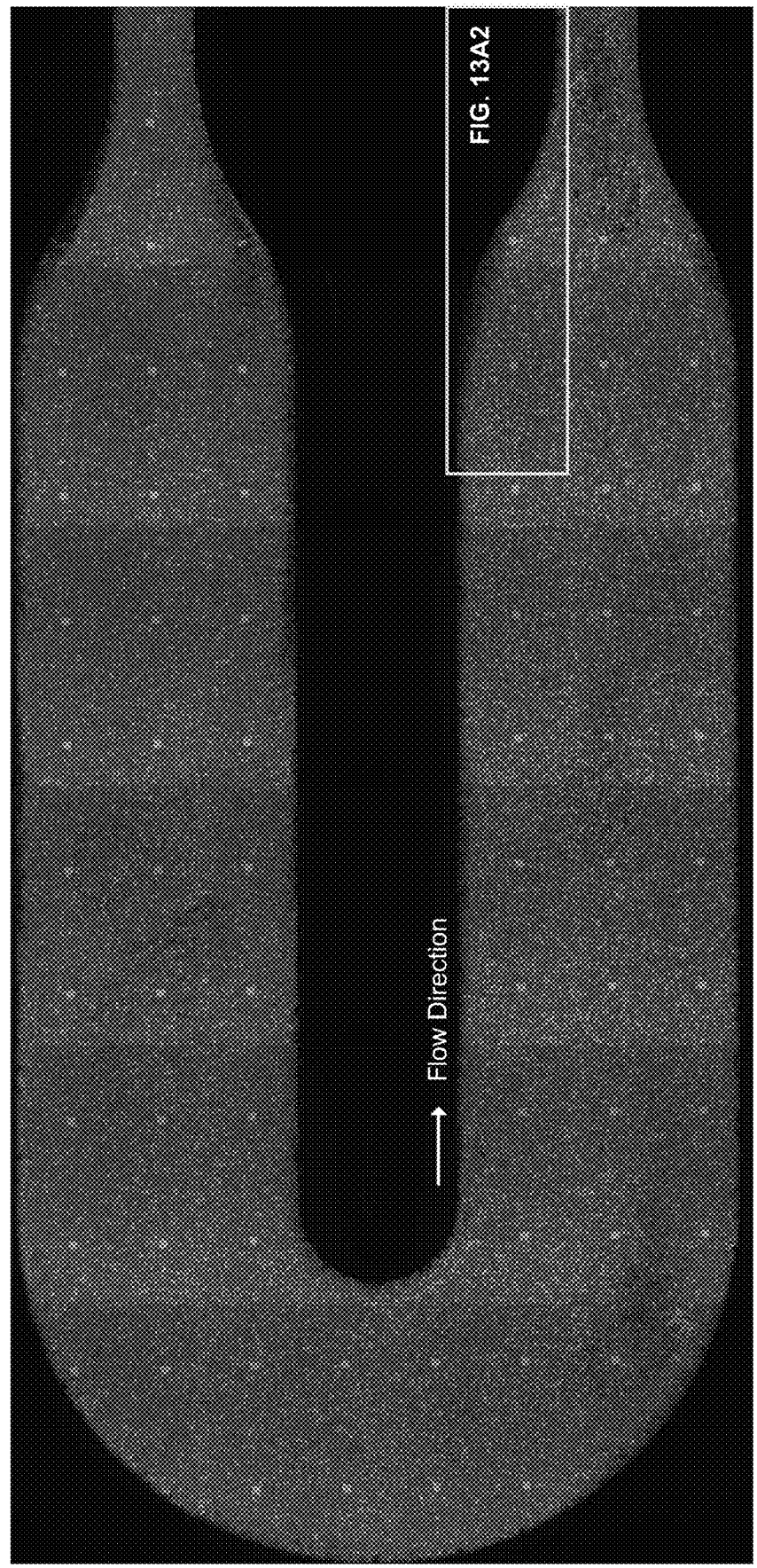
FIG. 13A1

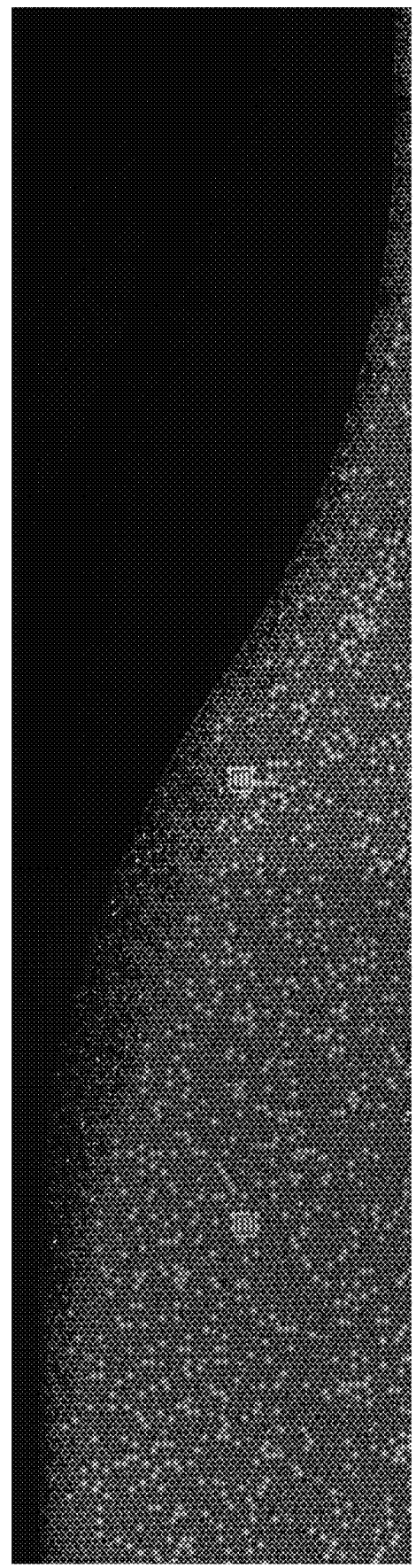
FIG. 13A2

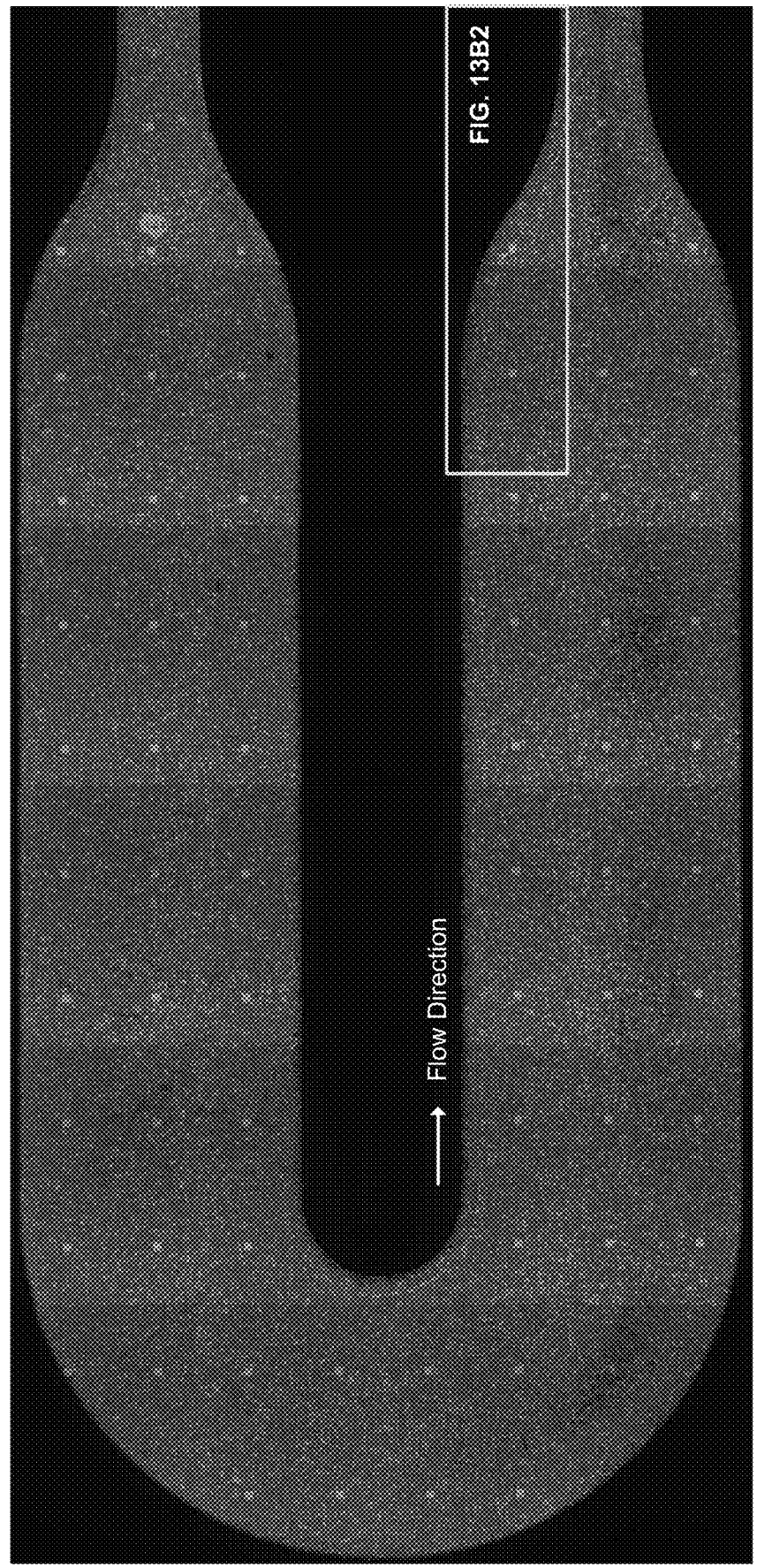
FIG. 13B1

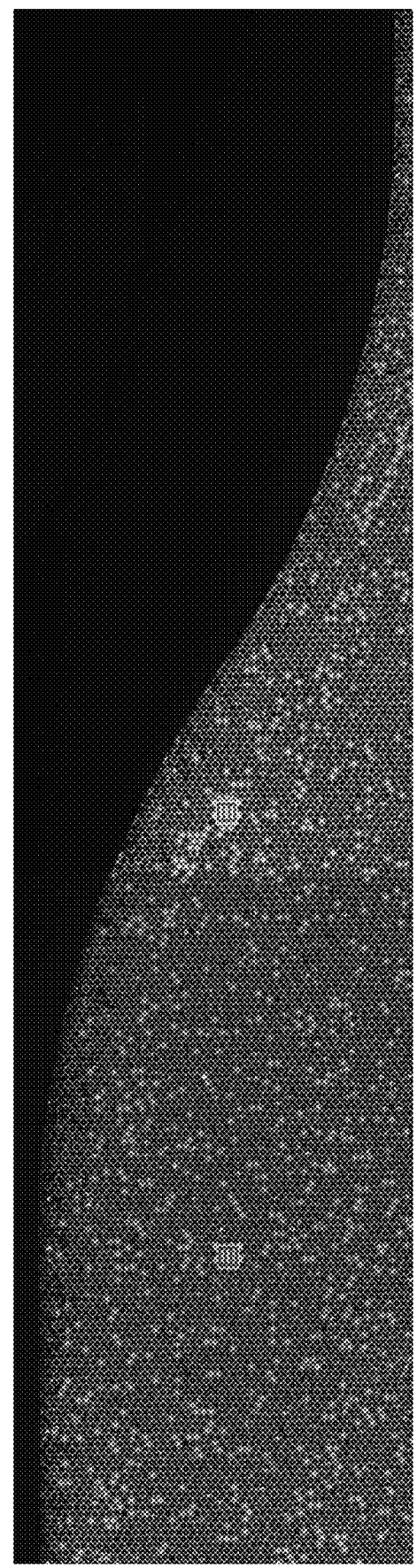
FIG. 13B2

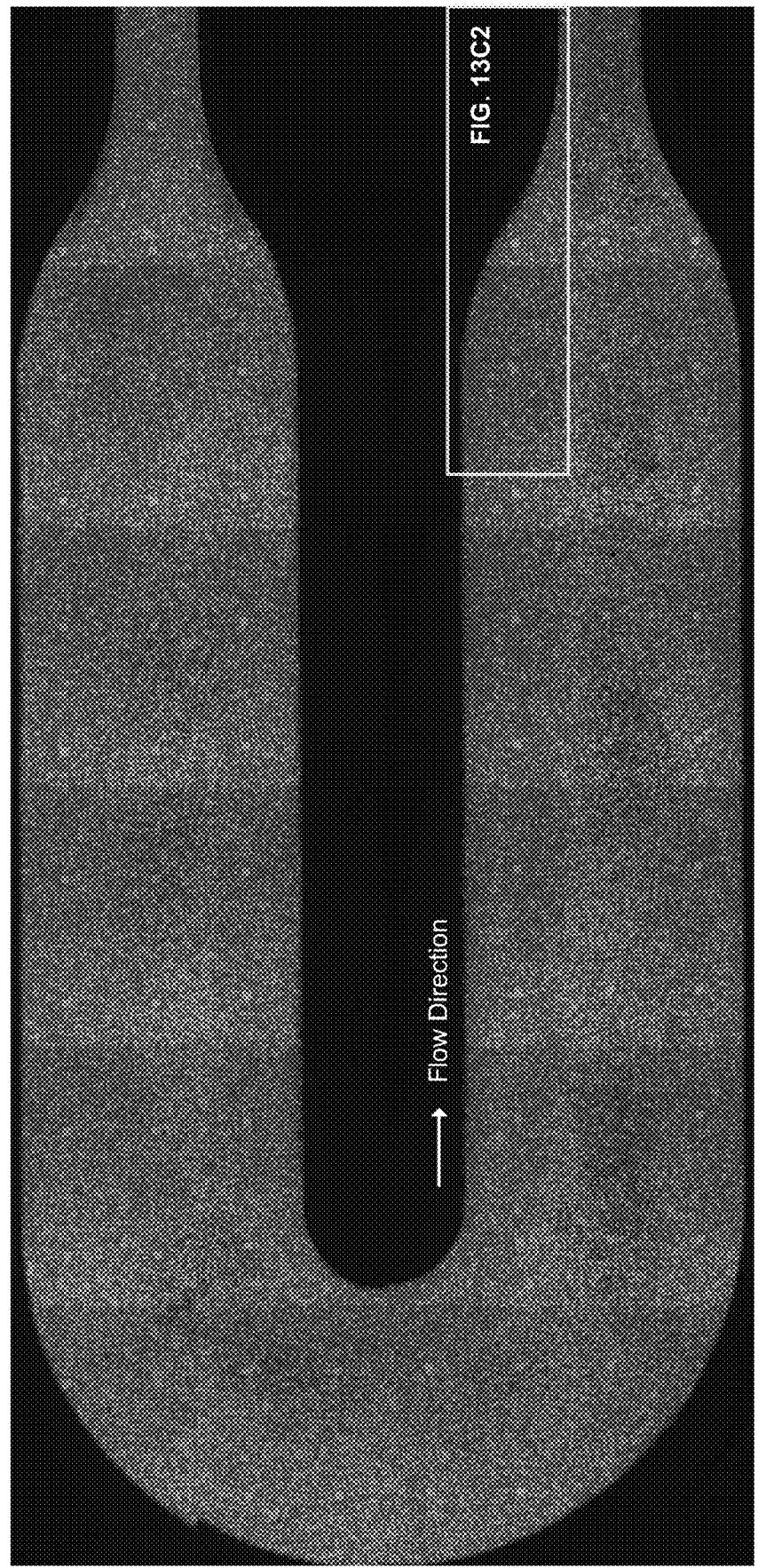
FIG. 13C1

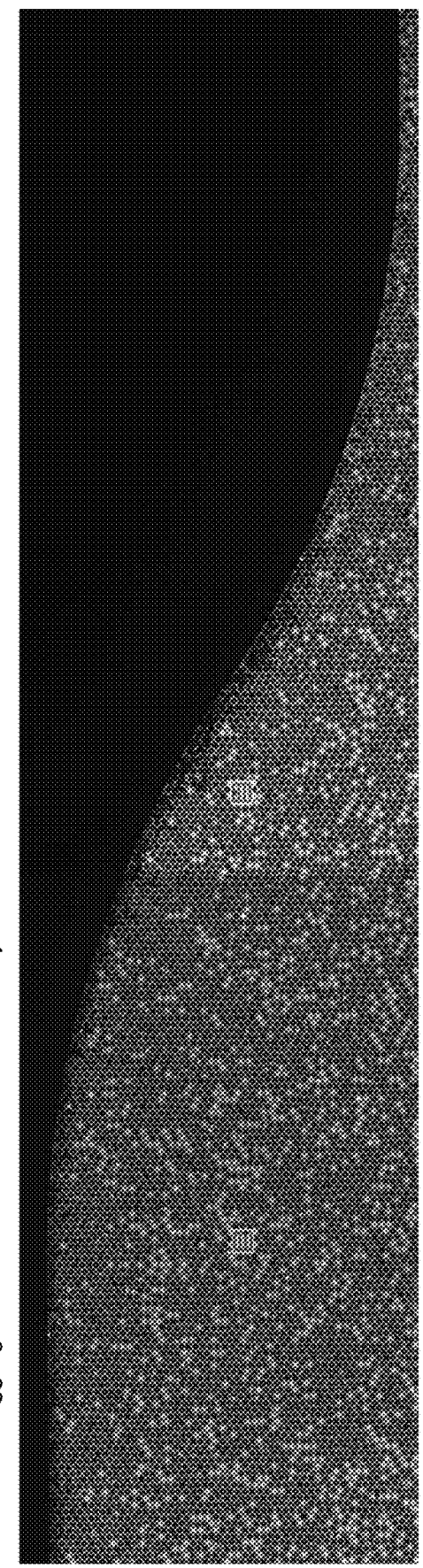
FIG. 13C2

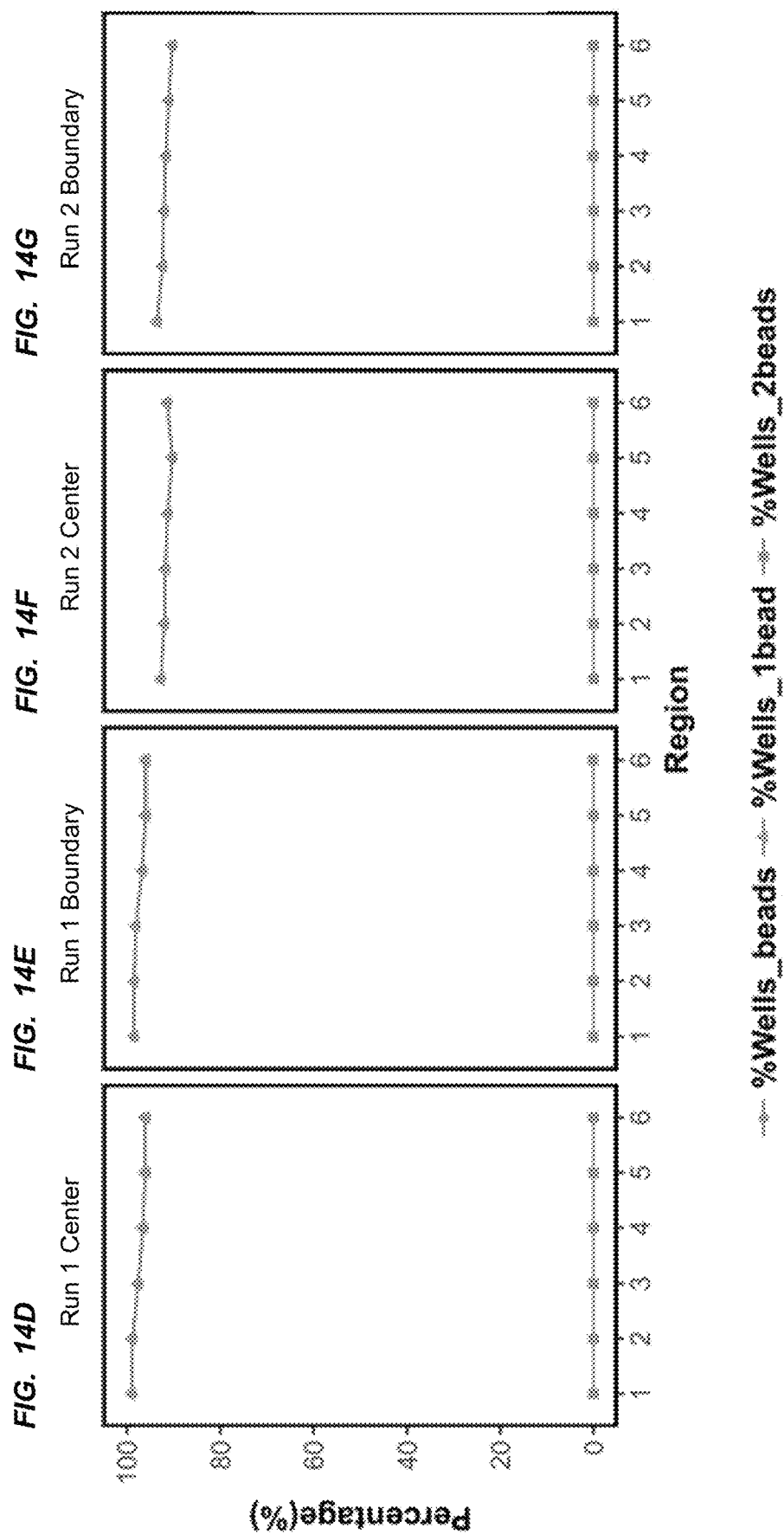

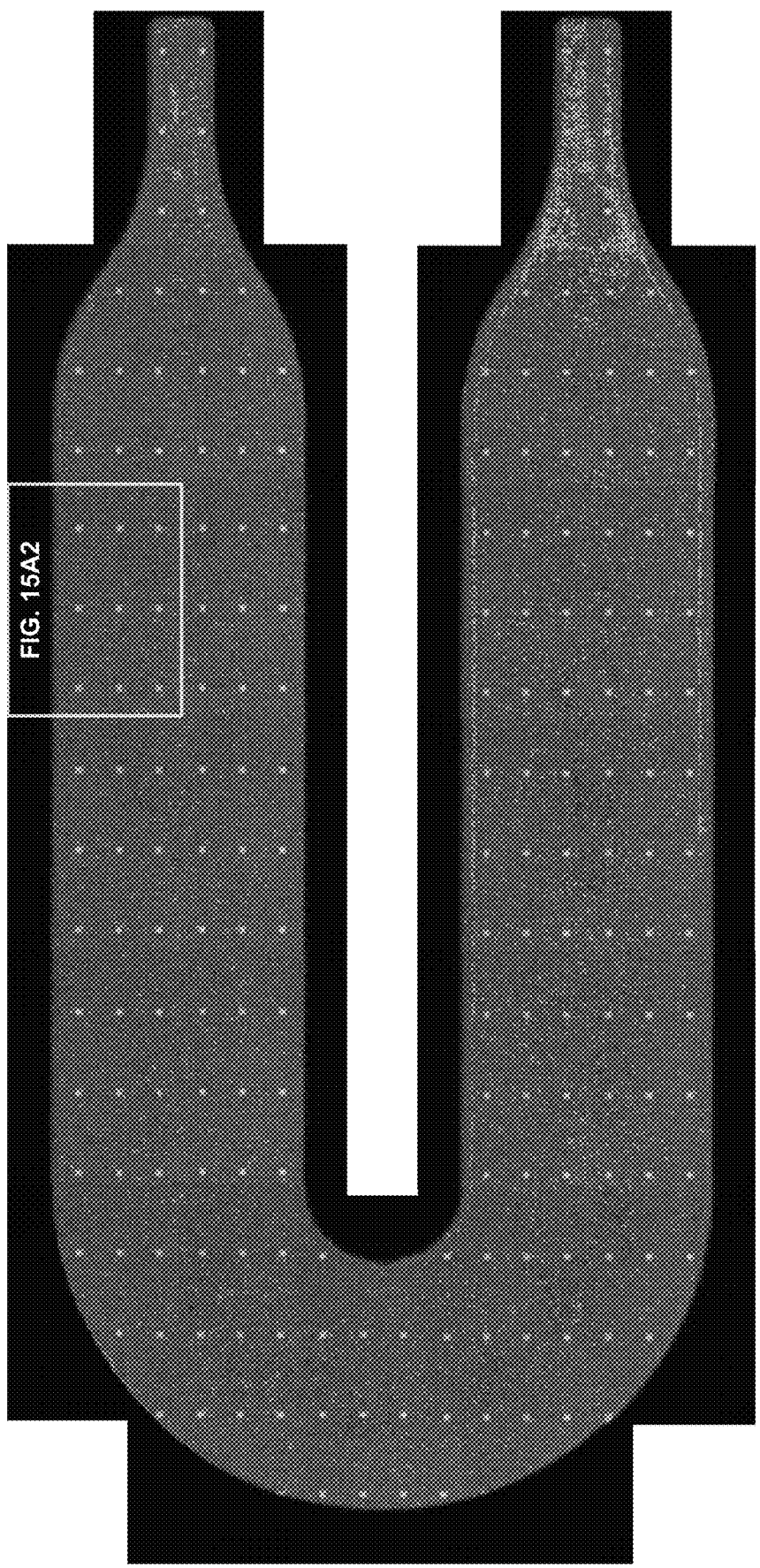
FIG. 15A1

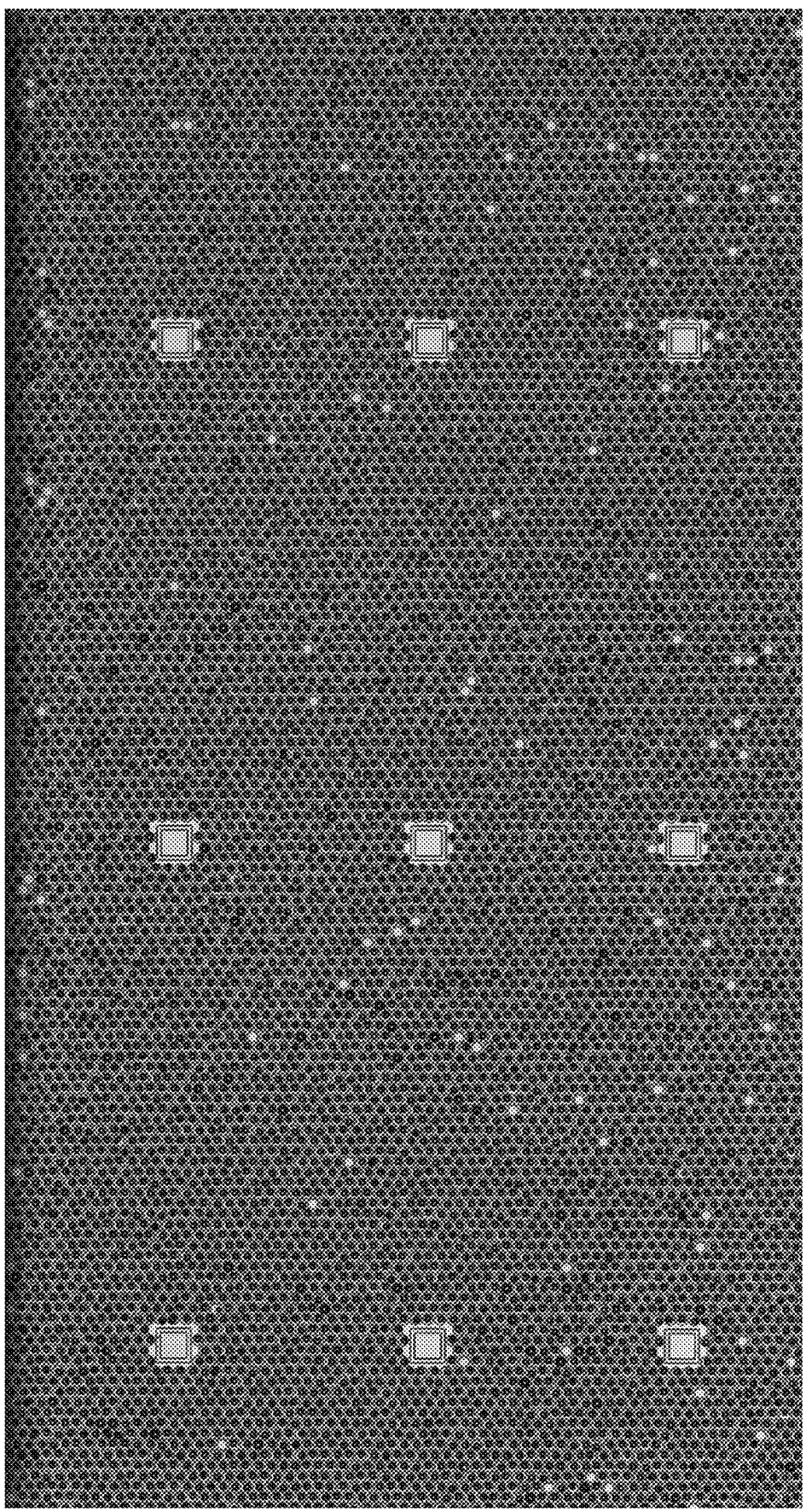
FIG. 15A2

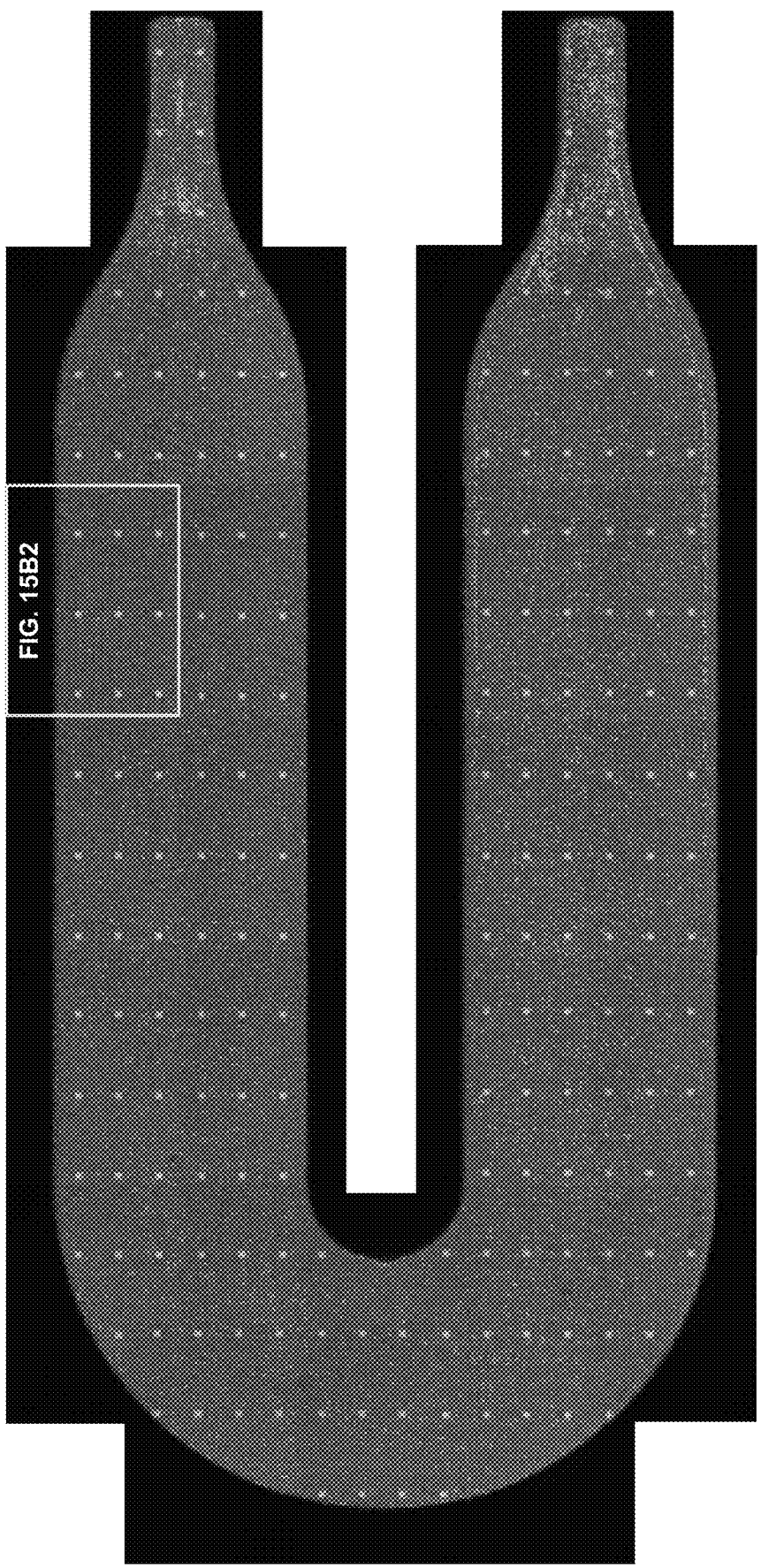
FIG. 15B1

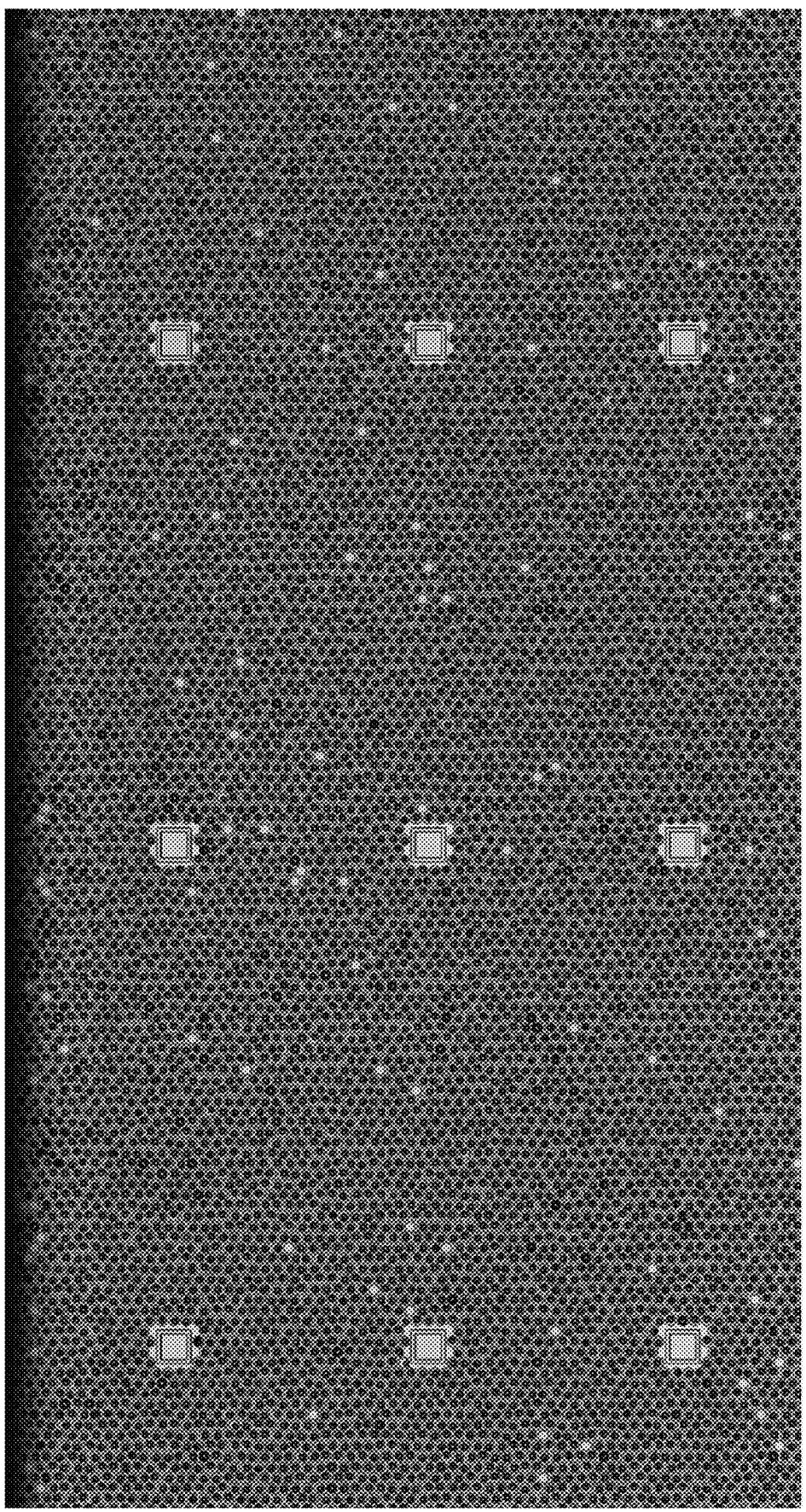
FIG. 15B2

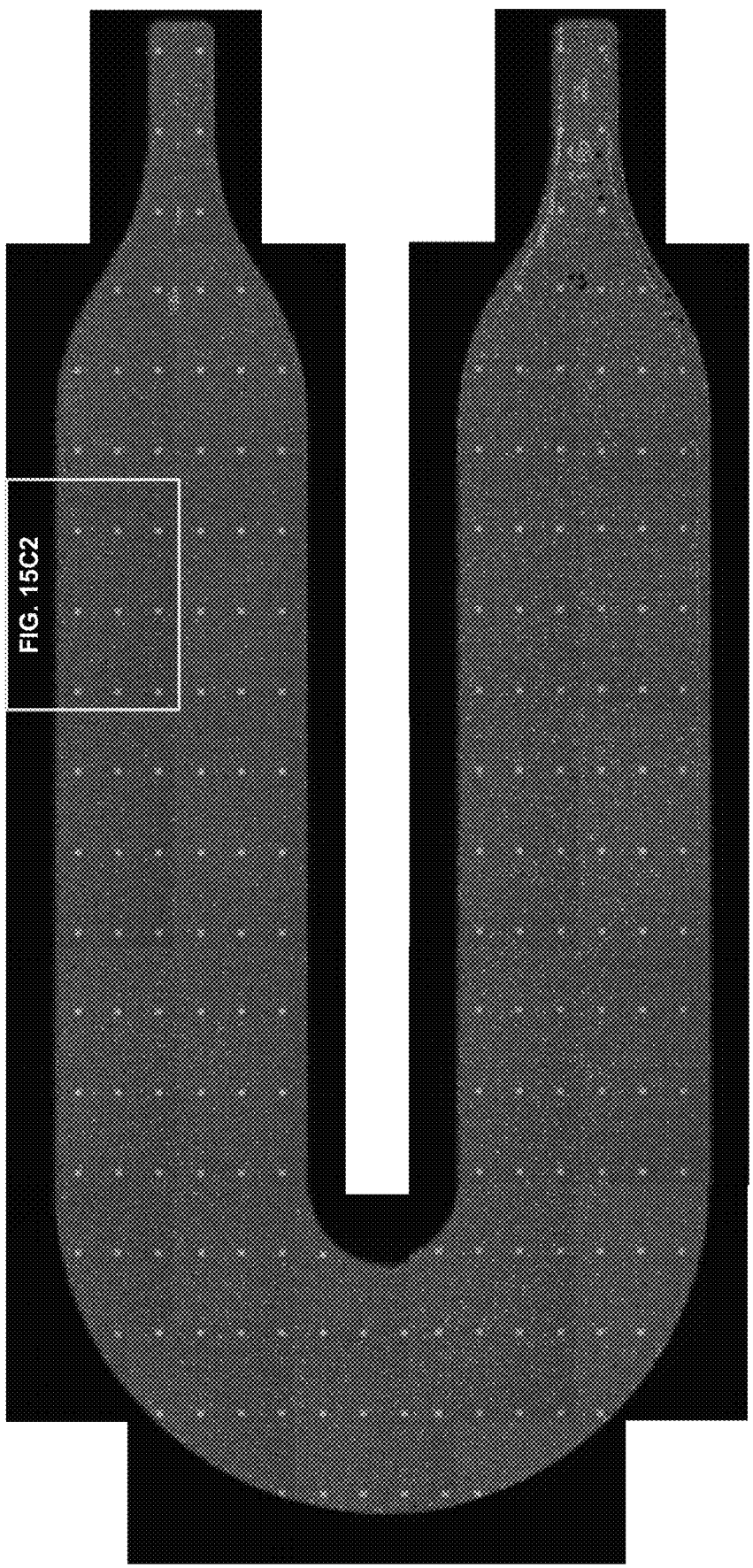
FIG. 15C1

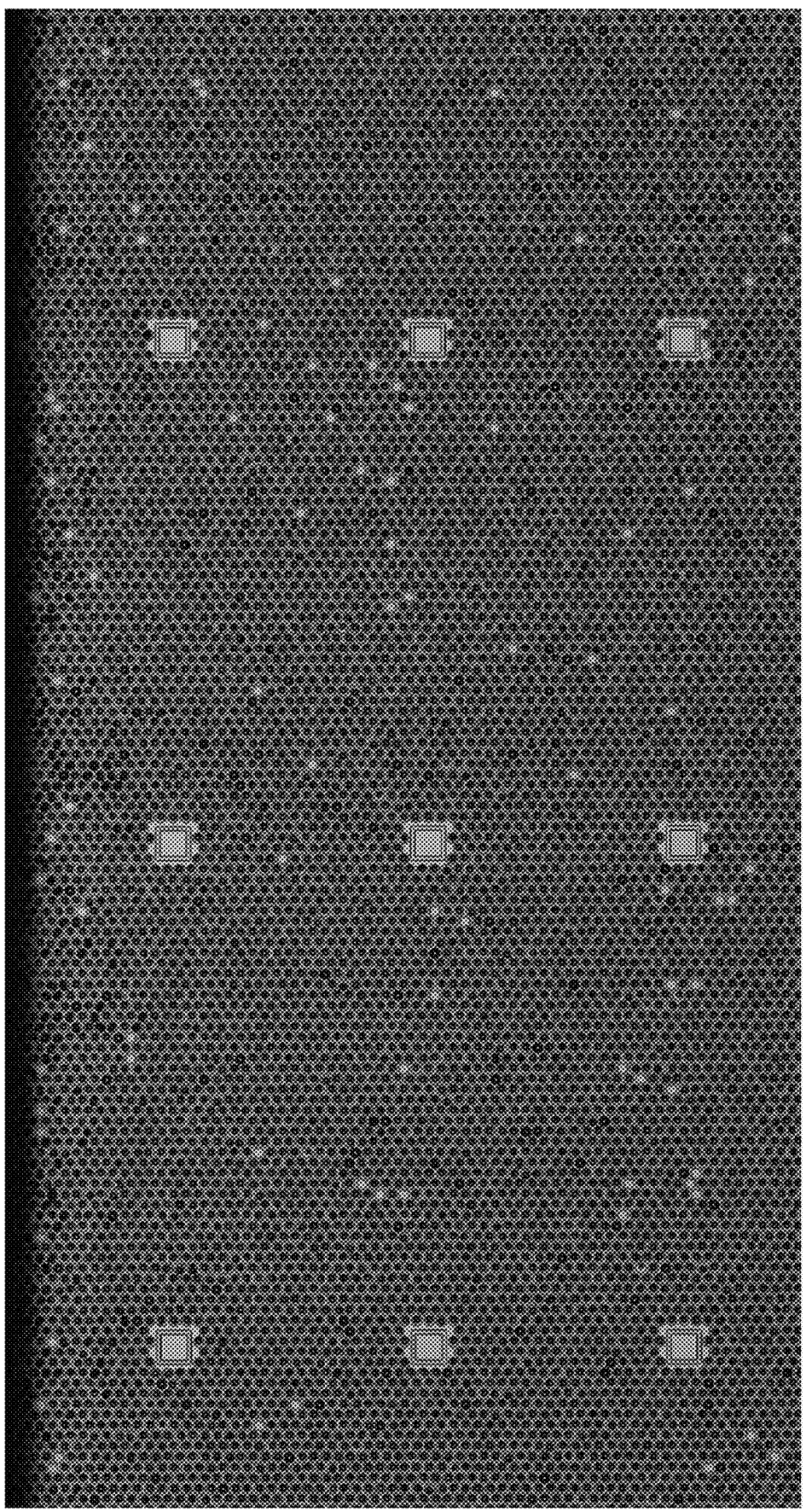
FIG. 15C2

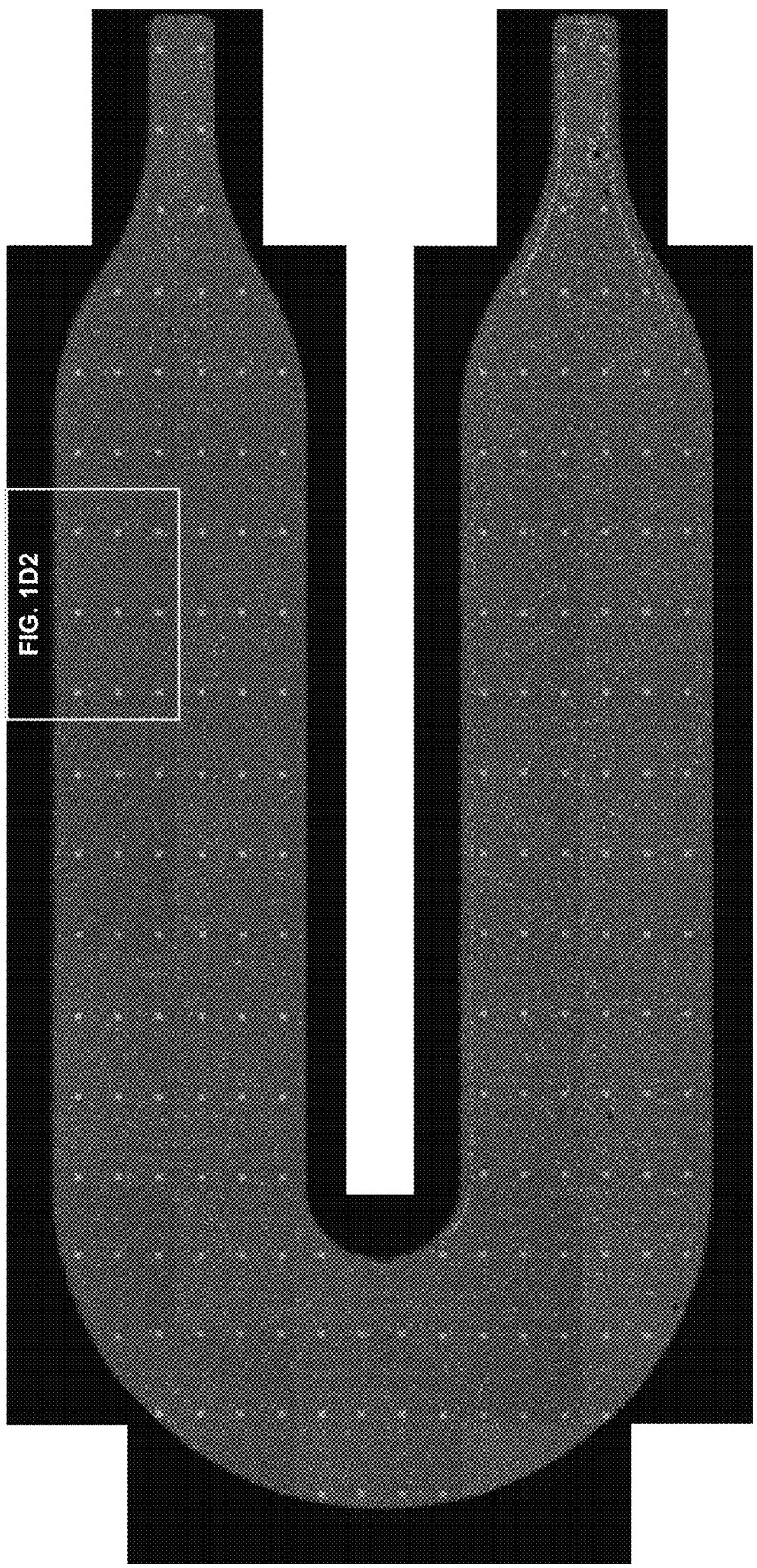
FIG. 15D1

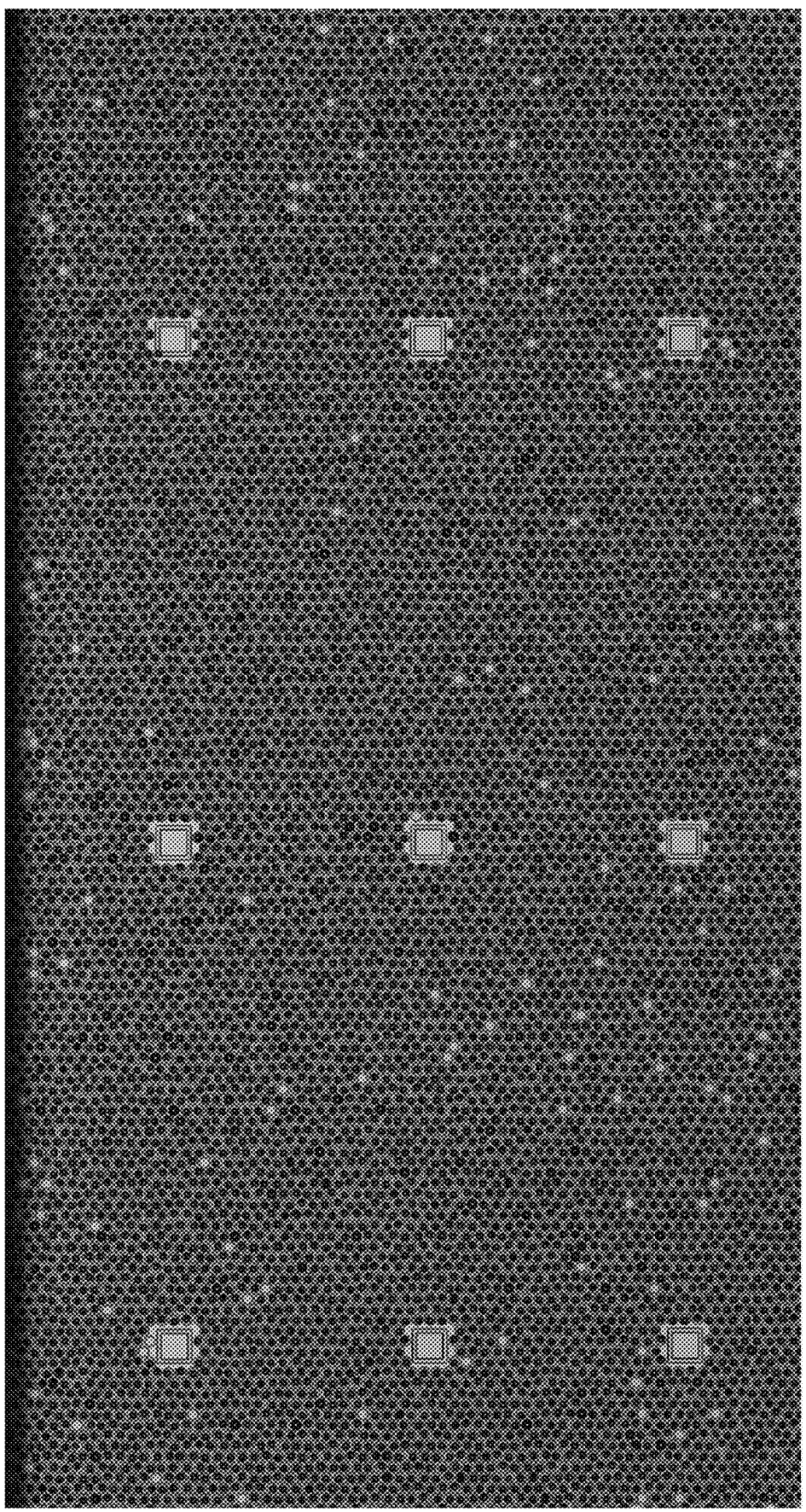
FIG. 15D2

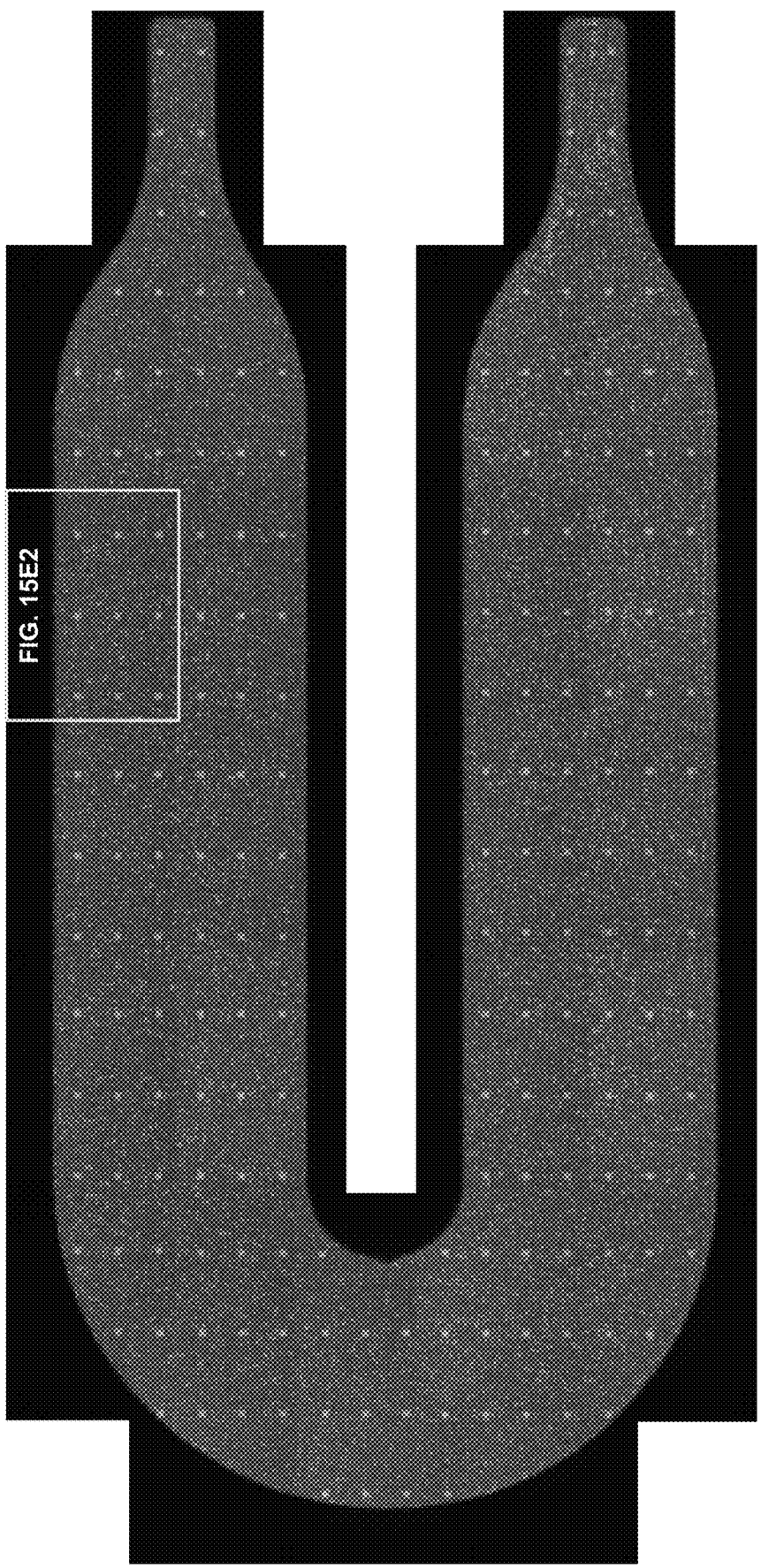
FIG. 15E1

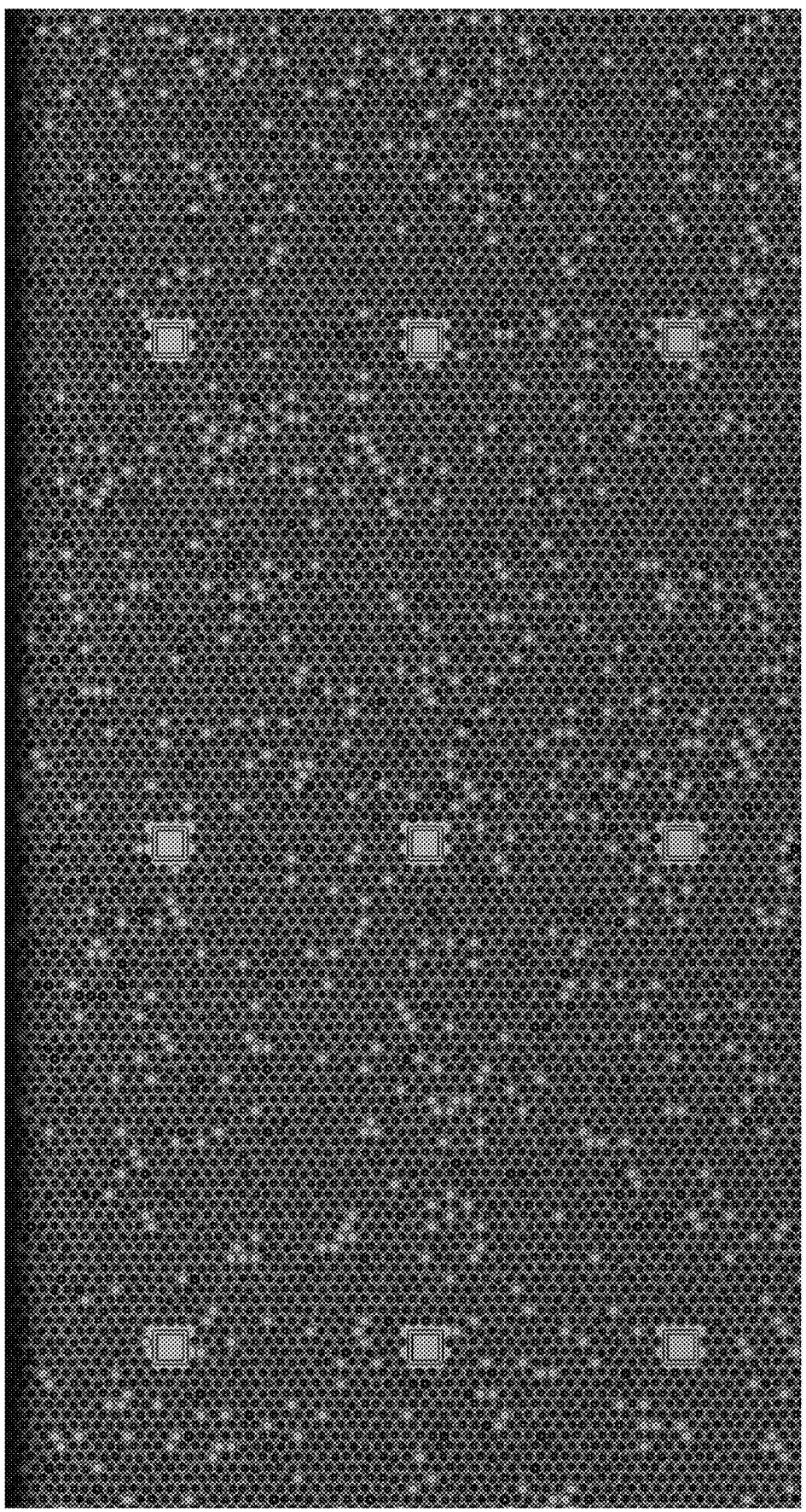
FIG. 15E2

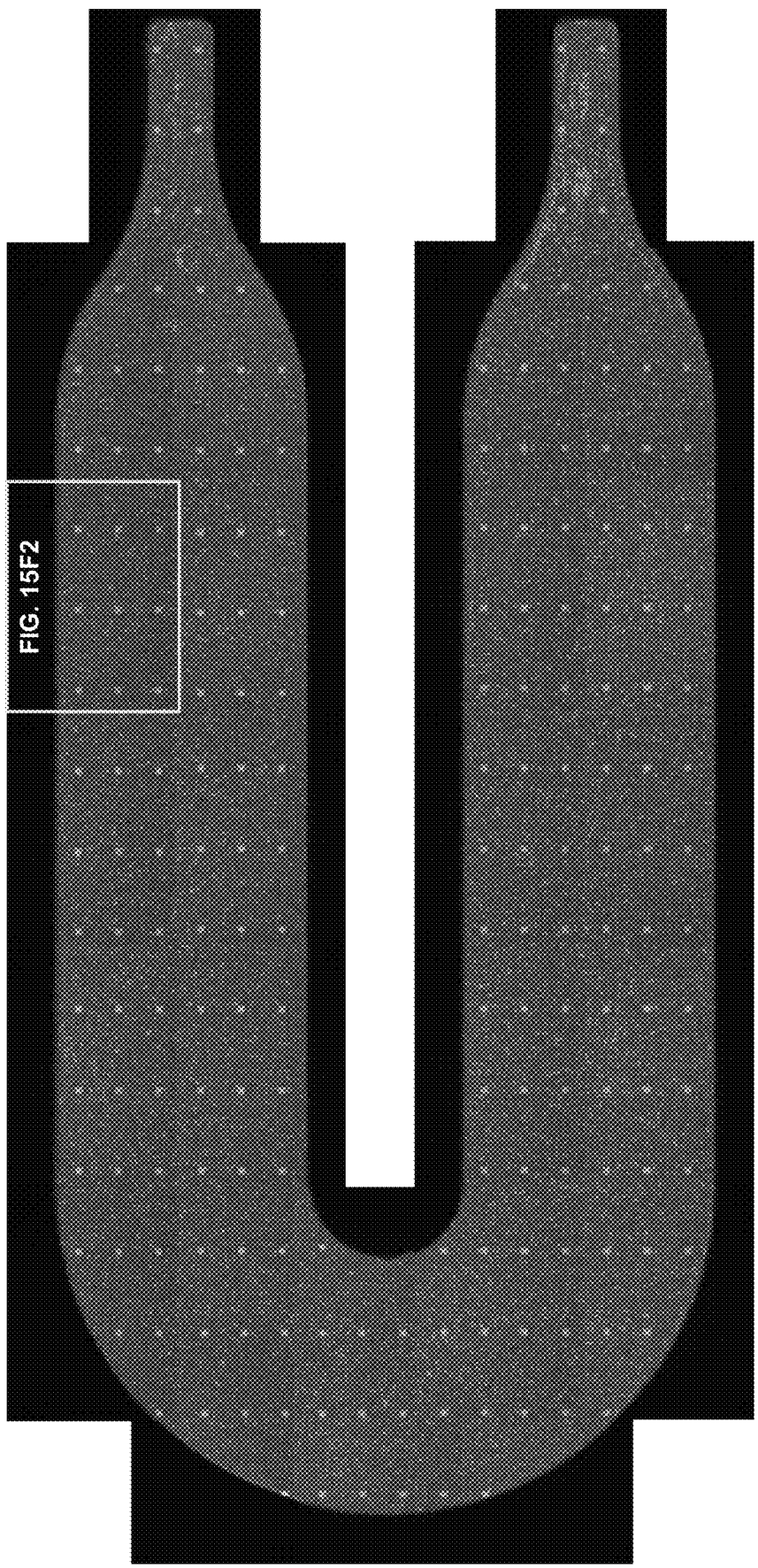
FIG. 15F1

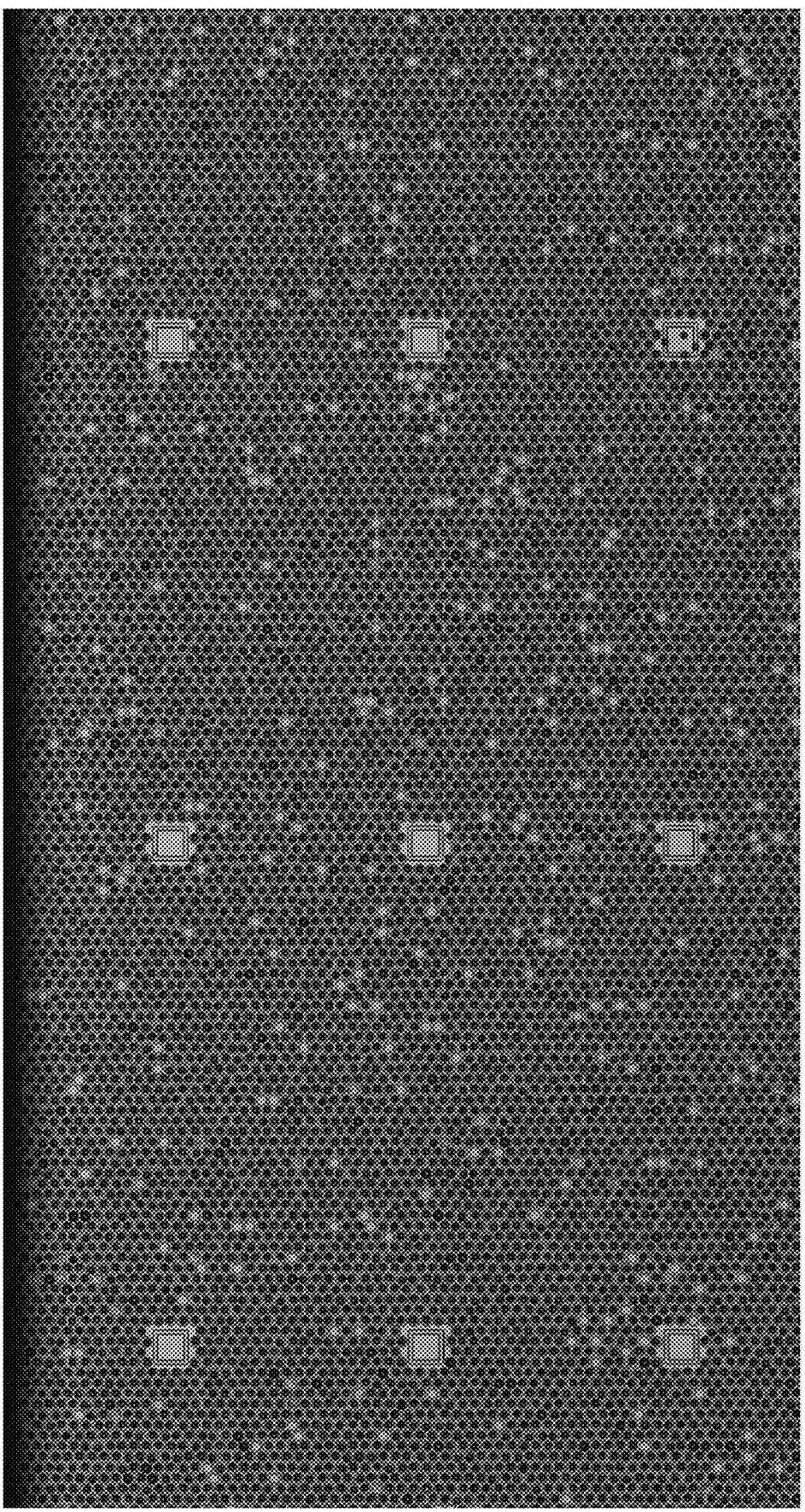
FIG. 15F2

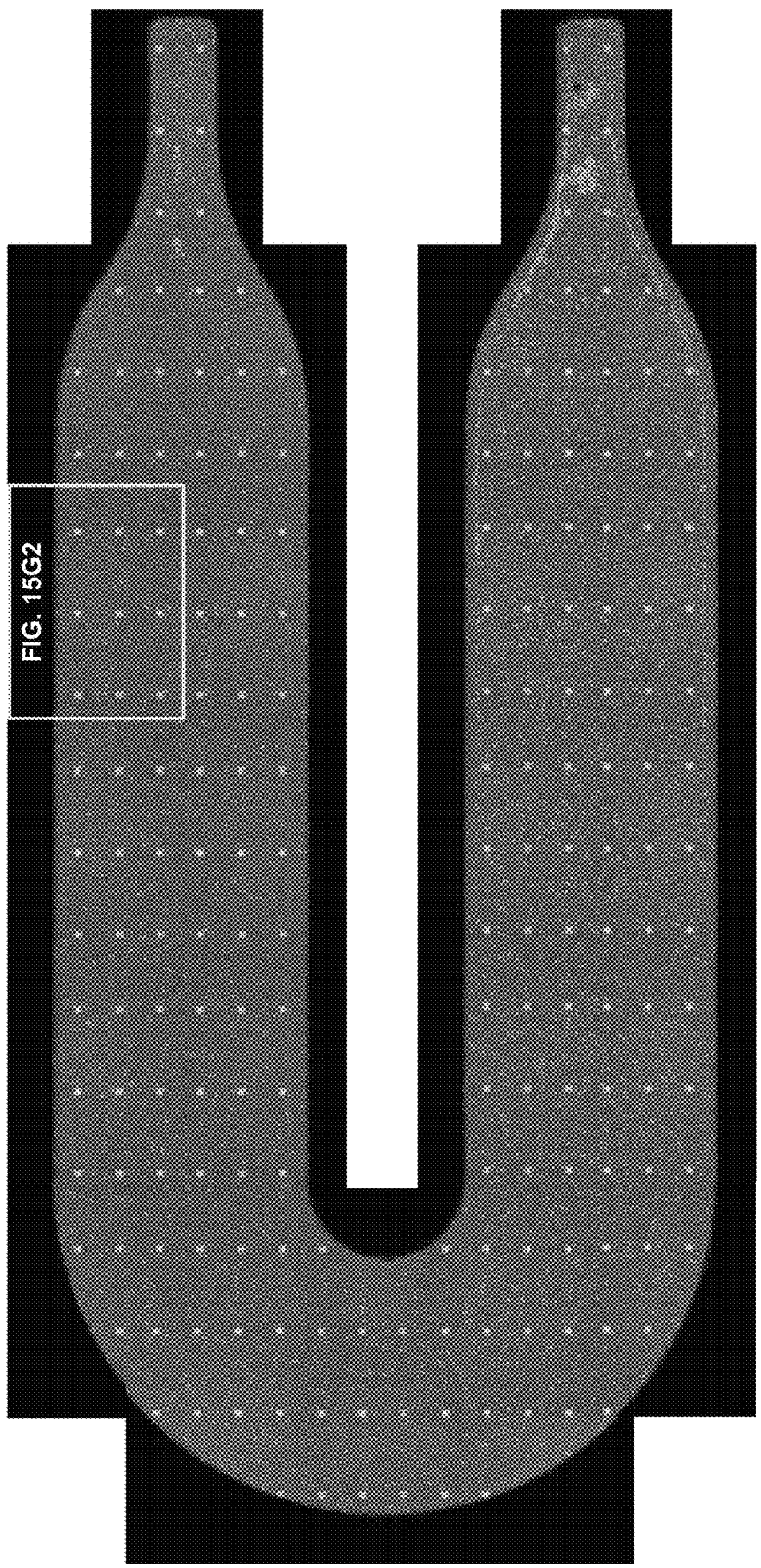
FIG. 15G1

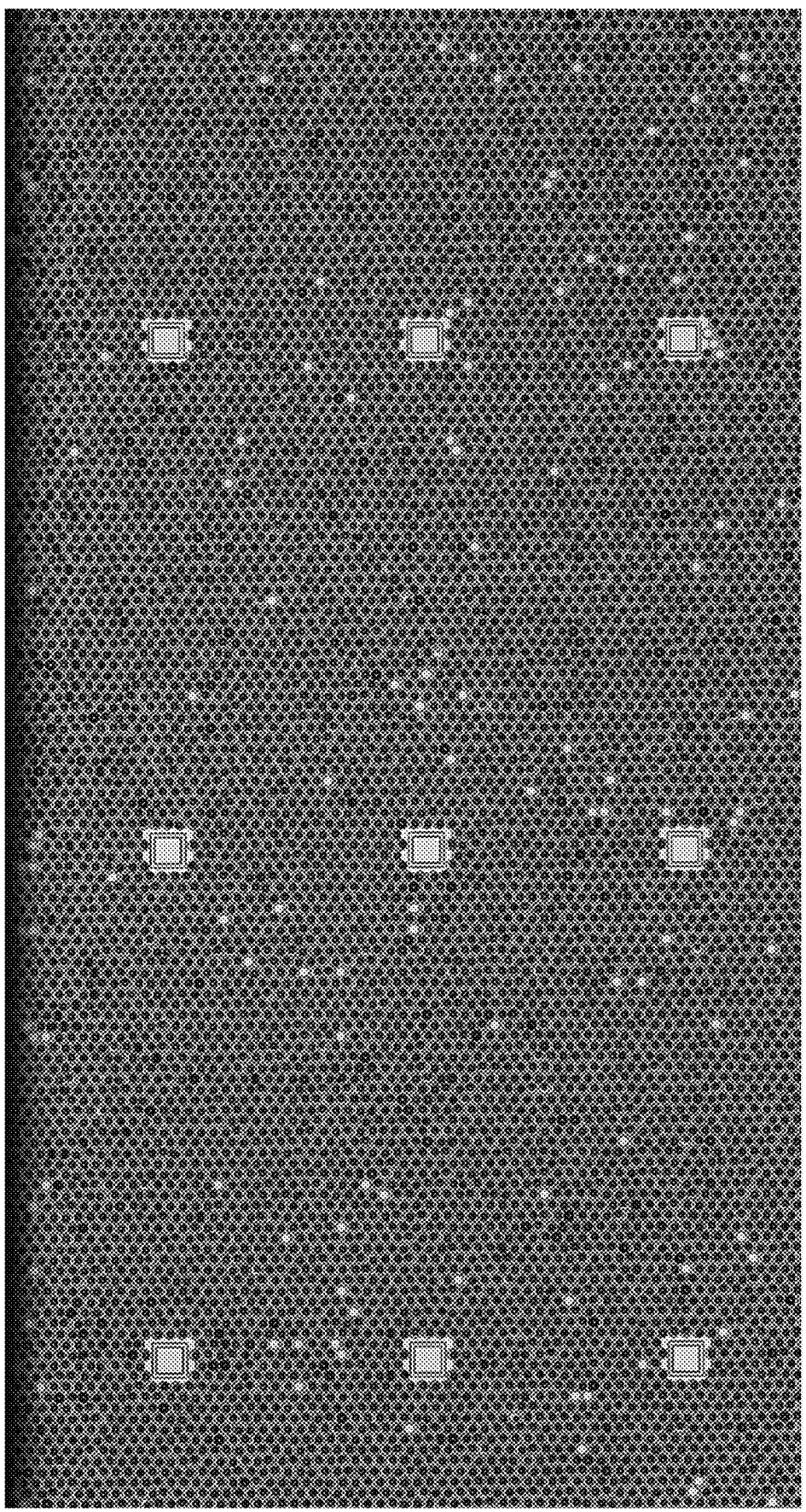
FIG. 15G2

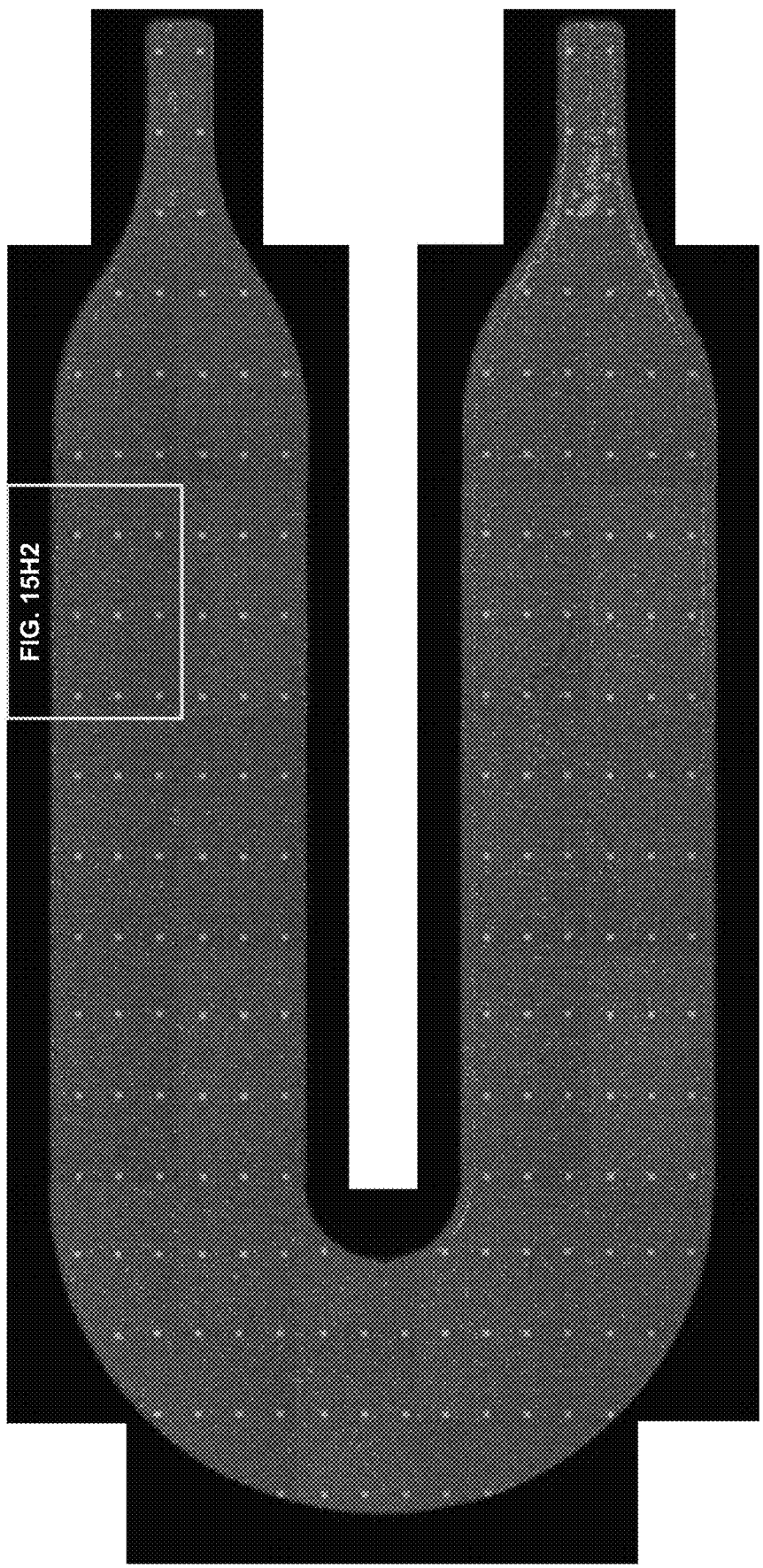
FIG. 15H1

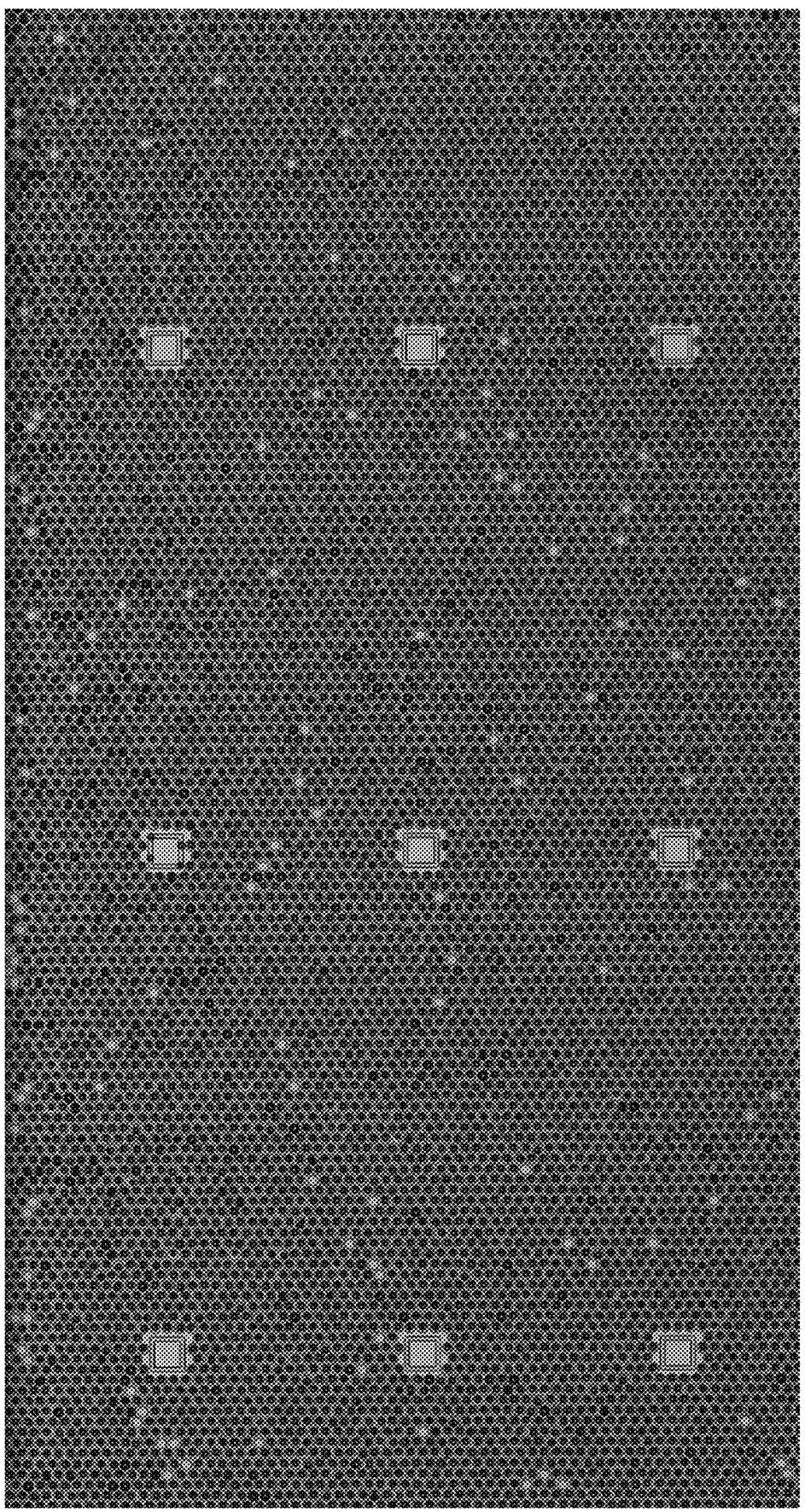
FIG. 15H2

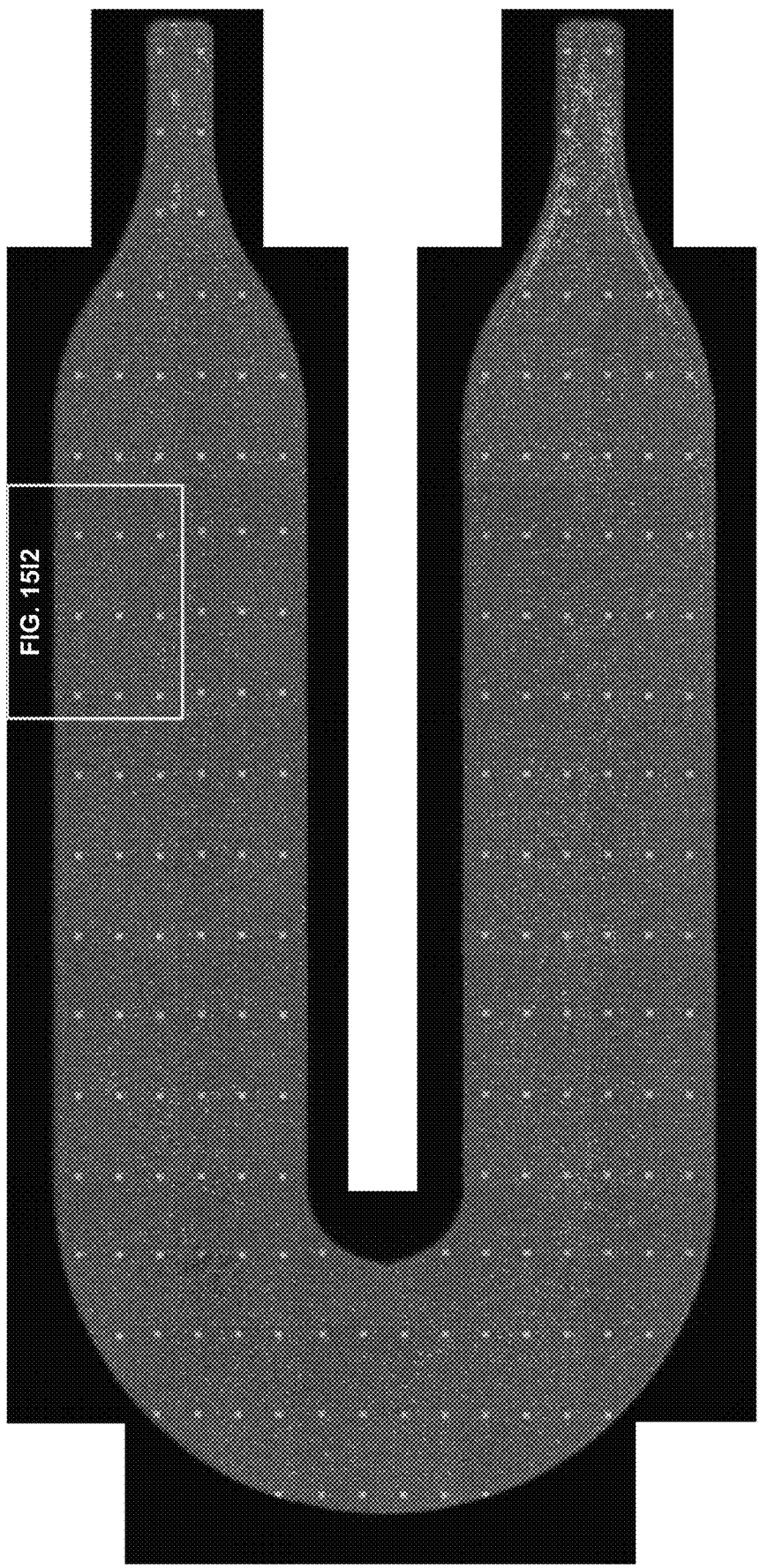
FIG. 15I1

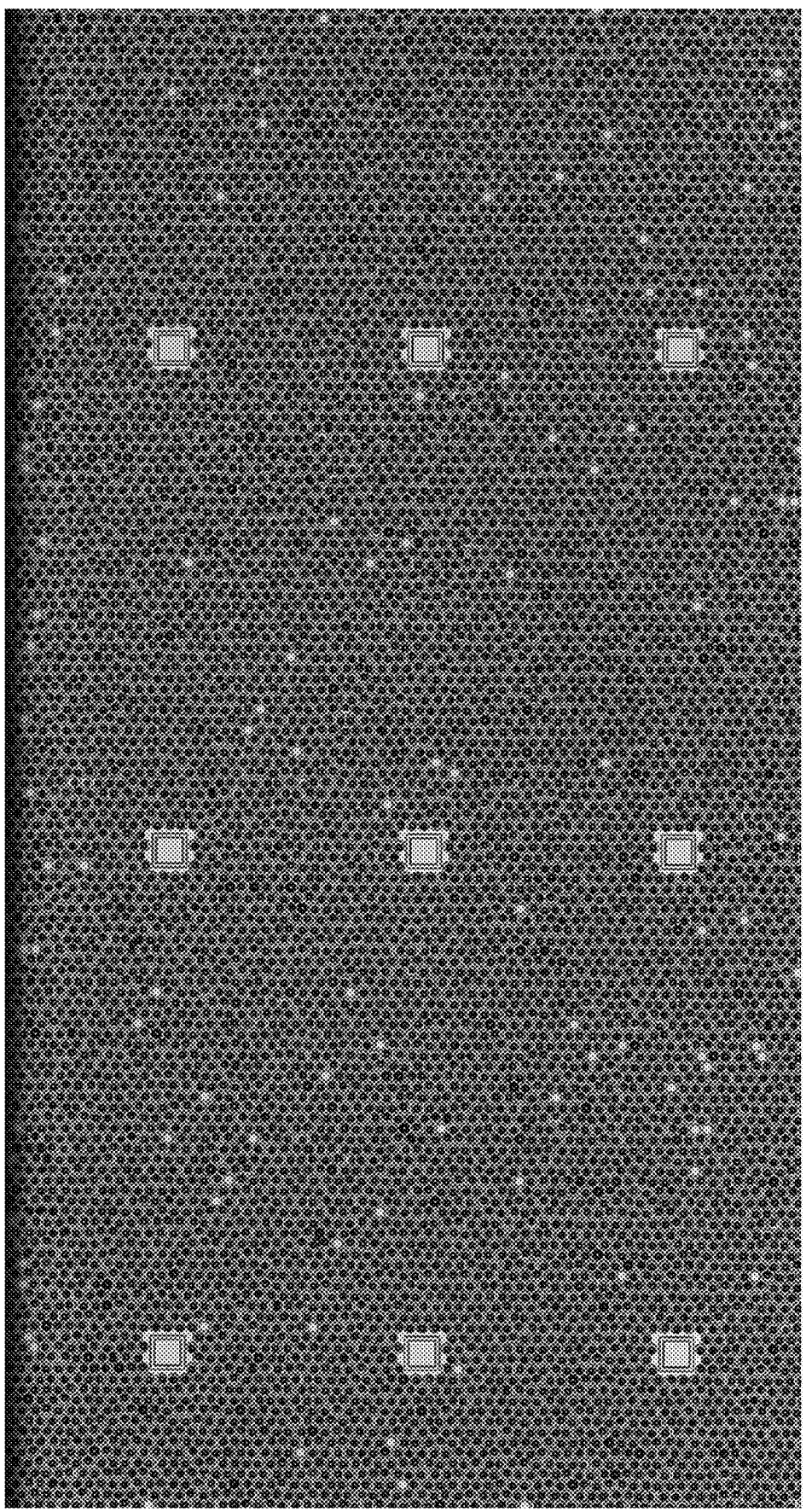
FIG. 15I2

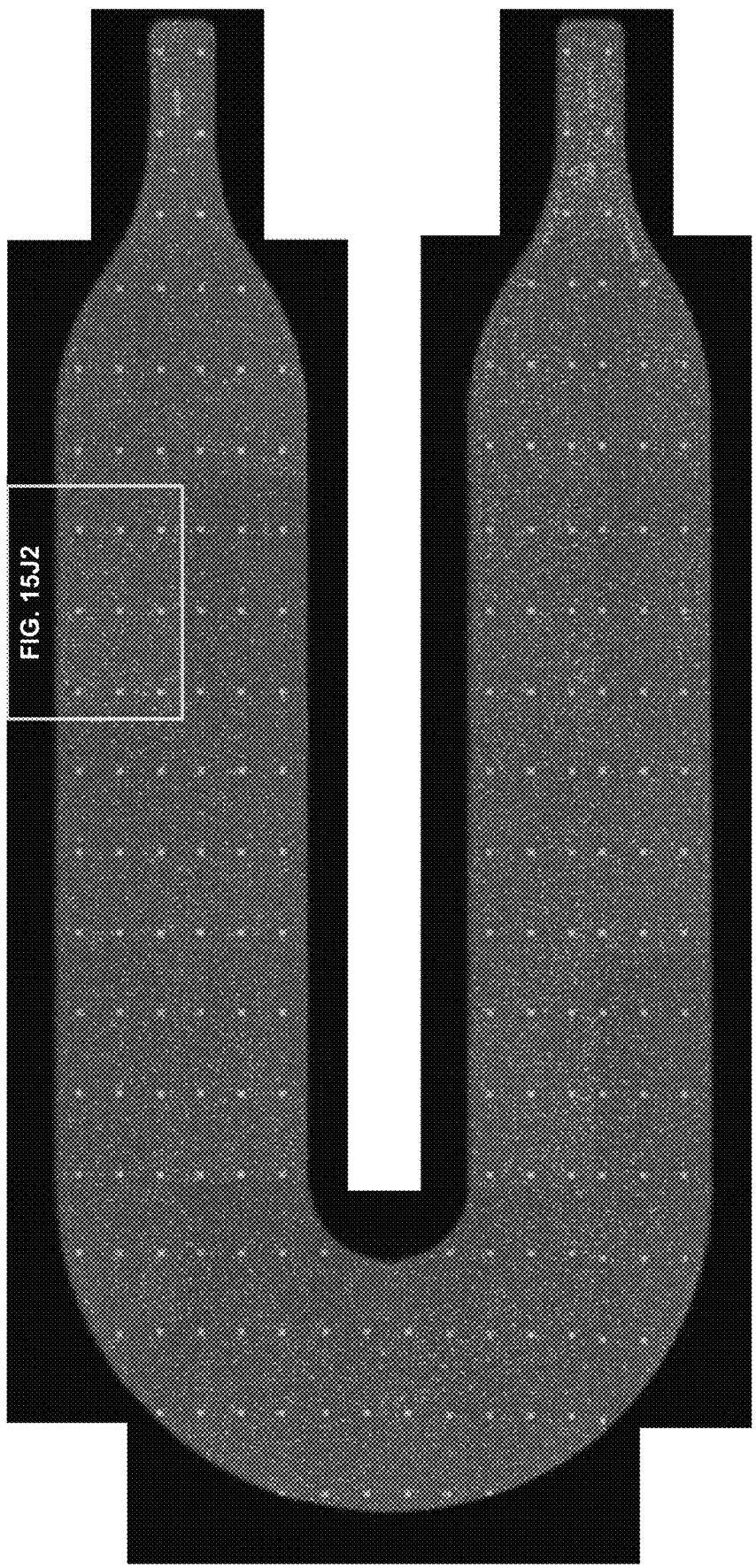
FIG. 15J1

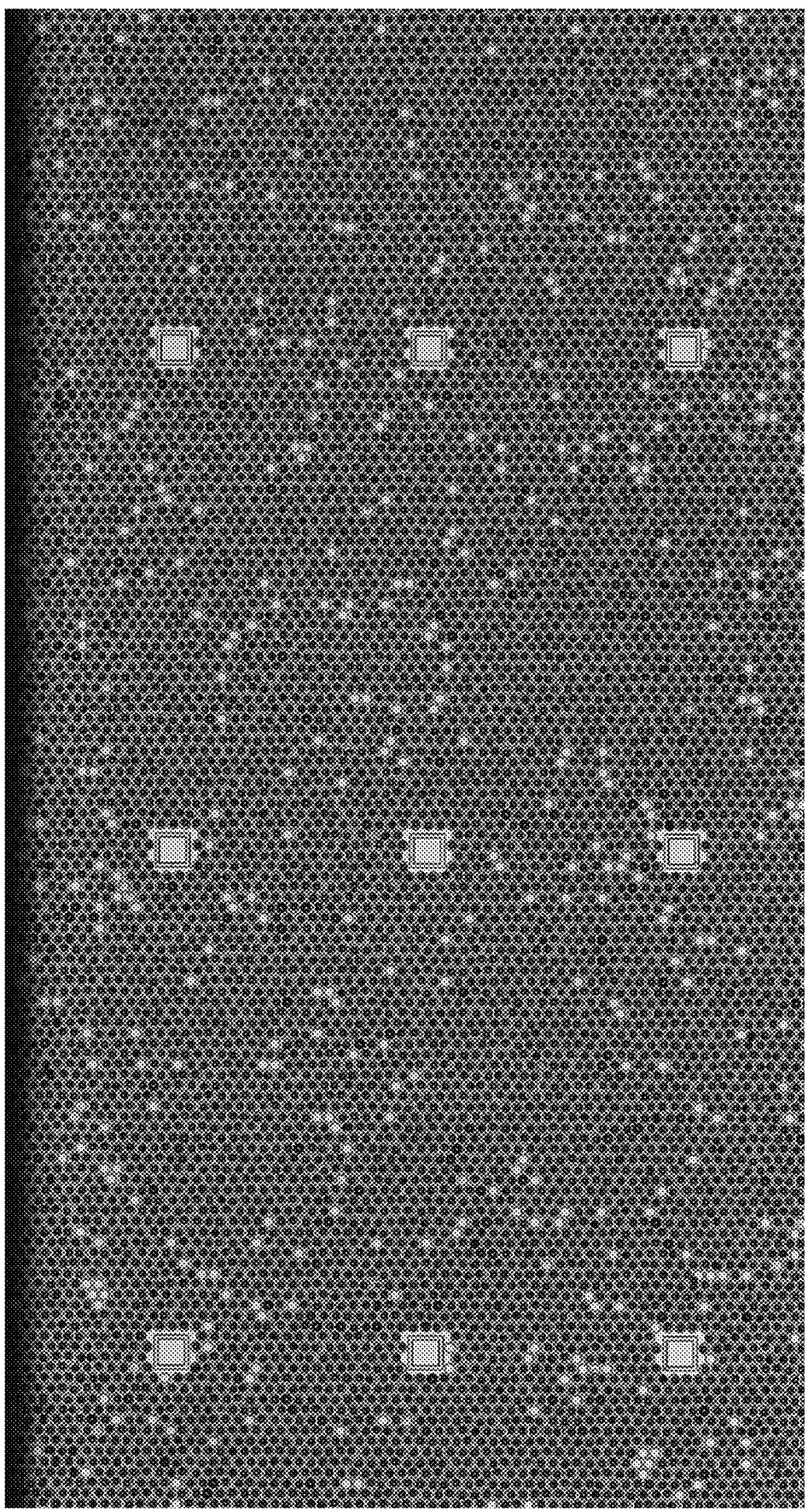
FIG. 15J2

*FIG. 16C* Quantiles

| | | |
|---|---|---|
| 100.0% | maximum | 97.161206 |
| 99.5% | | 97.158015223 |
| 97.5% | | 96.954977694 |
| 90.0% | | 96.494118706 |
| 75.0% | quartile | 95.96646987 |
| 50.0% | median | 95.212042 |
| 25.0% | quartile | 94.112848711 |
| 10.0% | | 92.522511156 |
| 2.5% | | 90.063815408 |
| 0.5% | | 85.400045063 |
| 0.0% | minimum | 85.245834253 |

*FIG. 16D* Summary Statistics

| | |
|---|---|
| Mean | 94.790576 |
| Std Dev | 1.7335477 |
| Std Err Mean | 0.1204899 |
| Upper 95% Mean | 95.028127 |
| Lower 95% Mean | 94.553024 |
| N | 207 |

HYDROPHILIC COATING OF FLUIDIC CHANNELS

RELATED APPLICATIONS

The present application claims priority under 35 U.S.C. § 119(e) to U.S. Provisional Application No. 62/446,223, filed on Jan. 13, 2017. The content of this related application is expressly incorporated herein by reference in its entirety.

BACKGROUND

Field

The present disclosure relates generally to the field of fluidic channels.

Description of the Related Art

Methods and techniques such as barcoding are useful for single cell analysis, in particular deciphering gene expression profiles to determine the states of single cells using, for example, reverse transcription, polymerase chain reaction (PCR) amplification, and next generation sequencing (NGS). The methods and techniques requires efficient loading of particles, such as barcode-bearing beads and cells onto a flowcell with a microwell array at its bottom. Such a flowcell can be used to decipher gene expression profiles of single cells by introducing single beads and single cells into microwells of the microwell array.

SUMMARY

Disclosed herein are devices for barcoding (e.g., stochastic barcoding). In some embodiments, a device comprises: a flowcell comprising a fluidic channel, an inlet port, and an outlet port, wherein the fluidic channel comprises a ceiling, a first sidewall, and a bottom, wherein the ceiling and the first sidewall form a ceiling-first sidewall edge, and wherein the bottom and the first sidewall for a bottom-first sidewall edge, wherein the contact angle of the ceiling is at least 10 degrees smaller than the contact angle of the first sidewall, wherein the bottom of the fluidic channel comprises a substrate which comprises a plurality of microwells, and wherein the inlet port and the outlet port are in fluid communication with the flowcell via the fluidic channel. The fluidic channel can comprise a second sidewall, wherein the ceiling and the second sidewall form a ceiling-second sidewall, and wherein the bottom and the second sidewall for a bottom-second sidewall.

In some embodiments, the fluidic channel has a non-circular cross section or an approximately rectangular cross section. The fluidic channel has a width of at least 2 mm, about 4 mm, or about 7 mm. The fluidic channel can be at least 0.8 mm in height, about 1.2 mm in height.

In some embodiments, the substrate can form the bottom of the fluidic channel, or the substrate can be on the bottom of the fluidic channel. In some embodiments, the substrate comprises silicon, fused-silica, glass, a polymer, a metal, an elastomer, polydimethylsiloxane, agarose, a hydrogel, or a combination thereof.

In some embodiments, the flowcell comprises silicon, fused-silica, glass, polydimethylsiloxane (PDMS), polymethylmethacrylate (PMMA) polycarbonate (PC), polypropylene (PP), polyethylene (PE), high density polyethylene (HOPE), polyimide, cyclic olefin polymers (COP), cyclic olefin copolymers (COO), polyethylene terephthalate (PET), epoxy resin, metal, or a combination thereof. The cyclic olefin polymers (COP) can comprise Zeonor® 1020E or Zeonor® 10608.

In some embodiments, the ceiling is hydrophilic. The contact angle of the ceiling corresponds to an average of contact angles of a plurality of locations on the ceiling. In some embodiments, the contact angle of the ceiling is 0-80 degrees, 0-60 degrees, or at most 10 degrees. The contact angle of the ceiling can be at least 30 degrees or at least 50 degrees smaller than the contact angle of the first sidewall.

In some embodiments, the contact angle of the first sidewall corresponds to an average of contact angles of a plurality of locations on the first sidewall. The contact angle of the first sidewall can be about 88 degrees. In some embodiments, the contact angle of the ceiling is sufficiently smaller than the contact angle of the first sidewall to enable non-laminar flow within the fluidic channel. In some embodiments, the first sidewall has a positive draft angle of 1-15 degrees.

In some embodiments, the non-laminar flow within the fluidic channel enables agitation of a particle on the surface of the substrate by a flow within the fluidic channel. A speed of the flow at a boundary between the flow and the bottom can be non-zero. The relative flow velocity of a flow across a cross section of the fluidic channel can be constant or approximately constant. The non-laminar flow can be plug flow.

In some embodiments, the non-laminar flow can be approximately plug flow. The plug flow can be approximately horizontal plug flow. The horizontal plug flow can be capillary aided horizontal plug flow. In some embodiments, the plug flow may not depend on buoyancy of a gas such as air, $CO_2$, or $N_2$. The plug flow may not depend on tilting of the device. The plug flow can be at a buffer-gas interface.

In some embodiments, the ceiling comprises a hydrophilic coating. The hydrophilic coating can be a superhydrophilic coating. The hydrophilic coating can comprise polyethylene glycol (PEG), poly-Hema, pluronic acid F68, pluronic acid F108, pluronic acid F127, polysorbate 20, silicon dioxide ($SiO_2$), silicon nitride, or any combination thereof. The hydrophilic coating has a contact angle of 0-80 degrees, 0-60 degrees, or at most 23 degrees. The ceiling can be coated with the hydrophilic coating by sputtering, thermal growth, adsorption, covalent binding, or any combination thereof. In some embodiments, the hydrophilic coating is offset from the edge formed by the ceiling and first sidewall by, for example, 100-1000 micrometers or 1%-25% of the width of the ceiling.

In some embodiments, the device comprises a plurality of particles residing in the plurality of microwells of the substrate, and wherein at least 25% of the plurality of microwells each contains a single particle. In some embodiments, at least 50% or 75% of the plurality of microwells each contains a single particle. The particle can comprise a bead or a cell. The bead can comprise a plurality of barcodes (e.g., stochastic barcodes). Each of the plurality of barcodes can comprise a molecular label selected from a group comprising at least 100 or 1000 molecular labels with unique sequences. Different barcodes of the plurality of barcodes can have the same cell label. The plurality of microwells can comprise at least 100 microwells, for example, 1000-5000000 microwells.

In some embodiments, a microwell of the plurality of microwells has a volume of 1 femtoliter-1 microliter, or 1 picoliter-1 nanoliter. The microwell of the plurality of microwells can have a non-circular cross section in a plane of the substrate, and the non-circular cross section in the plane of the substrate can be square or hexagonal. The microwell of the plurality of microwells can be 25-100 micrometers in depth, such as 50 micrometers in depth. The microwell of the plurality of microwells can have a width of 25-100 micrometers, such as 50 micrometers. An aspect ratio of the width of the microwell to the depth of the microwell can be 0.1-2. In some embodiments, a dimension of the microwell of the plurality of microwells allows the microwell to contain at most one bead. A ratio of the width of the microwell to a diameter of the at most one bead can be 1.2-1.8. In some embodiments, a percentage of the plurality of microwells containing a single bead is at least 90%.

In some embodiments, the microwell of the plurality of microwells comprises a coating of polyethylene glycol (PEG), poly-Hema, pluronic acid F68, pluronic acid F108, pluronic acid F127, polysorbate 20, silicon dioxide ($SiO_2$), silicon nitride, or a combination thereof. The microwell of the plurality of microwells can comprise a plasma-treated surface.

In some embodiments, the inlet port and the outlet port are capable of directing a flow of a fluid through the fluidic channel, thereby contacting the microwells with the fluid. In some embodiments, the device comprises a pipette tip interface for loading or removing a cell sample, an assay reagent, a bead suspension, waste from the device, or a combination thereof. The device can comprise the cell sample, the assay reagent, the bead suspension, or a combination thereof.

Disclosed herein are methods for sample loading. In some embodiments, a method comprises: (a) providing a device that comprises: a flowcell comprising a fluidic channel, an inlet port, and an outlet port, wherein the fluidic channel comprises a ceiling, a first sidewall, and a bottom, wherein the ceiling and the first sidewall form a ceiling-first sidewall edge, and wherein the bottom and the first sidewall for a bottom-first sidewall edge, wherein the contact angle of the ceiling is at least 10 degrees smaller than the contact angle of the first sidewall, wherein the bottom comprises a substrate which comprises a plurality of microwells, and wherein the inlet port and the outlet port are in fluid communication with the flowcell via the fluidic channel; (b) introducing a gas such as air, $CO_2$, or $N_2$ into the fluidic channel via the inlet port; and (c) introducing a first sample comprising a first plurality of particles into the fluidic channel via the inlet port, whereby at least 25% of the plurality of microwells each contains a single particle of the first plurality of particles. In some embodiments, at least 50% or 75% of the plurality of microwells each contains a single particle of the first plurality of particles. The fluidic channel can comprise a second sidewall, wherein the ceiling and the second sidewall form a ceiling-second sidewall, and wherein the bottom and the second sidewall for a bottom-second sidewall.

In some embodiments, the method can comprise (d) introducing a gas such as air, $CO_2$, or $N_2$ into the fluidic channel via the inlet port; and (e) introducing a second sample into the fluidic channel via the inlet port after introducing the first sample into the fluidic channel, wherein the second sample comprises a second plurality of particles, and whereby at least 25% of the plurality of microwells each contains a single particle of the second plurality of particles. In some embodiments, at least 50% or 75% of the plurality of microwells each contains a single particle of the second plurality of particles.

In some embodiments, after introducing the second sample into the fluidic channel via the inlet port in (e), at least 25% or 50% of the plurality of microwells each contains a single particle of the first plurality of particles and a single particle of the second plurality of particles.

The first plurality of particles can comprise a plurality of beads, and a bead of the plurality of beads can comprise a plurality of barcodes (e.g. stochastic barcodes). The second plurality of particles comprises a plurality of cells. The first plurality of particles comprises a plurality of cells. The second plurality of particles can comprise a plurality of beads, and wherein a bead of the plurality of beads comprises a plurality of barcodes (e.g., stochastic barcodes).

In some embodiments, the plurality of cells of the first plurality of particles or the plurality of cells of the second plurality of particles comprises stem cells, cancer cells, blood cells, peripheral blood mononuclear cells, circulating tumor cells, breast cancer cells, cells at a cell cycle phase of desire, or a combination thereof. The first sample or the second sample comprises a biological sample, a clinical sample, an environmental sample, or a combination thereof. The first sample or the second sample can comprise one or more of a biological fluid, tissue and cell from a patient. The first sample or the second sample comprises blood, urine, cerebrospinal fluid, pleural fluid, amniotic fluid, semen, saliva, bone marrow, a biopsy sample, or a combination thereof.

In some embodiments, introducing the gas into the fluidic channel via the inlet port in (b) comprises injecting the gas into the fluidic channel via the inlet port. Introducing the first sample into the fluidic channel via the inlet port can comprise injecting the first sample into the fluidic channel via the inlet port. Introducing the gas into the fluidic channel via the inlet port in (d) can comprises injecting the gas into the fluidic channel via the inlet port.

In some embodiments, the method comprises: prior to introducing the gas or another gas into the fluidic channel via the inlet port in (d), introducing a first buffer into the fluidic channel via the inlet port to remove the first plurality of particles that are on the bottom and are not contained in any of the plurality of microwells. The method can comprise: after introducing the second sample into the fluidic channel via the inlet port in (e), introducing a second buffer into the fluidic channel via the inlet port to remove the second plurality of particles that are on the bottom and are not contained in any of the plurality of microwells.

In some embodiments, the fluidic channel has a non-circular cross section or an approximately rectangular cross section. The fluidic channel can have a width of at least 2 mm, about 7 mm, or about 4 mm. The fluidic channel can be at least 0.8 mm in height, about 1.2 mm in height.

In some embodiments, the substrate can form the bottom of the fluidic channel, or the substrate can be on the bottom of the fluidic channel. In some embodiments, the substrate comprises silicon, fused-silica, glass, a polymer, a metal, an elastomer, polydimethylsiloxane, agarose, a hydrogel, or a combination thereof.

In some embodiments, the flowcell comprises silicon, fused-silica, glass, polydimethylsiloxane (PDMS), polymethylmethacrylate (PMMA), polycarbonate (PC), polypropylene (PP), polyethylene (PE), high density polyethylene (HOPE), polyimide, cyclic olefin polymers (COP), cyclic olefin copolymers (COO), polyethylene terephthalate (PET), epoxy resin, metal, or a combination thereof. The cyclic olefin polymers (COP) can comprise Zeonor® 1020R or Zeonor® 1060R.

In some embodiments, the ceiling is hydrophilic. The contact angle of the ceiling corresponds to an average of contact angles of a plurality of locations on the ceiling. In some embodiments, the contact angle of the ceiling is 0-80 degrees, 0-60 degrees, or at most 10 degrees. The contact angle of the ceiling can be at least 30 degrees or at least 50 degrees smaller than the contact angle of the first sidewall.

In some embodiments, the contact angle of the first sidewall corresponds to an average of contact angles of a plurality of locations on the first sidewall. The contact angle of the first sidewall can be about 88 degrees. In some embodiments, the contact angle of the ceiling is sufficiently smaller than the contact angle of the first sidewall to enable non-laminar flow within the fluidic channel. In some embodiments, the first sidewall has a positive draft angle of 1-15 degrees.

In some embodiments, the non-laminar flow within the fluidic channel enables agitation of a particle on the surface of the substrate by a flow within the fluidic channel. A speed of the flow at a boundary between the flow and the bottom can be non-zero. The relative flow velocity of a flow across a cross section of the fluidic channel can be constant or approximately constant. The non-laminar flow can be plug flow.

In some embodiments, the non-laminar flow can be approximately plug flow. The plug flow can be approximately horizontal plug flow. The horizontal plug flow can be a capillary aided horizontal plug flow. In some embodiments, the plug flow may not depend on buoyancy of the gas. The plug flow may not depend on tilting of the device. The plug flow can be at a buffer-gas interface.

In some embodiments, the ceiling comprises a hydrophilic coating. The hydrophilic coating can be a superhydrophilic coating. The hydrophilic coating can comprise polyethylene glycol (PEG), poly-Hema, pluronic acid F68, pluronic acid F108, pluronic acid F127, polysorbate 20, silicon dioxide ($SiO_2$), silicon nitride, or any combination thereof. The hydrophilic coating has a contact angle of 0-80 degrees, 0-60 degrees, or at most 23 degrees. The ceiling can be coated with the hydrophilic coating by sputtering, thermal growth, adsorption, covalent binding, or any combination thereof. In some embodiments, the hydrophilic coating is offset from the edge formed by the ceiling and first sidewall by, for example, 100-1000 micrometers or 1%-25% of the width of the ceiling.

In some embodiments, the substrate comprises a plurality of particles, and wherein at least 25% of the plurality of microwells each contains a single particle. At least 50% or 75% of the plurality of microwells each contains a single particle. The particle can comprise a bead or a cell. The bead can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof. The bead can comprise a plurality of barcodes (e.g., stochastic barcodes). Each of the plurality of barcodes can comprise a molecular label selected from a group comprising at least 100 or 1000 molecular labels with unique sequences. Different barcodes of the plurality of barcodes can have the same cell label. The plurality of microwells can comprise at least 100 microwells, for example, 1000-5000000 microwells.

In some embodiments, a microwell of the plurality of microwells has a volume of 1 femtoliter-1 microliter, or 1 picoliter-1 nanoliter. The microwell of the plurality of microwells can have a non-circular cross section in a plane of the substrate, and the non-circular cross section in the plane of the substrate can be square or hexagonal. The microwell of the plurality of microwells can be 25-100 micrometers in depth, such as 50 micrometers in depth. The microwell of the plurality of microwells can have a width of 25-100 micrometers, such as 50 micrometers. An aspect ratio of the width of the microwell to the depth of the microwell can be 0.1-2. In some embodiments, a dimension of the microwell of the plurality of microwells allows the microwell to contain at most one bead. A ratio of the width of the microwell to a diameter of the at most one bead can be 1.2-1.8. In some embodiments, a percentage of the plurality of microwells containing a single bead is at least 90%.

In some embodiments, the microwell of the plurality of microwells comprises a coating of polyethylene glycol (PEG), poly-Hema, pluronic acid F68, pluronic acid F108, pluronic acid F127, polysorbate 20, silicon dioxide ($SiO_2$), silicon nitride, or a combination thereof. The microwell of the plurality of microwells can comprise a plasma-treated surface.

In some embodiments, the inlet port and the outlet port are capable of directing a flow of a fluid through the fluidic channel, thereby contacting the microwells with the fluid. In some embodiments, the device comprises a pipette tip interface for loading or removing a cell sample, an assay reagent, a bead suspension, waste from the device, or a combination thereof. The device can comprise the cell sample, the assay reagent, the bead suspension, or a combination thereof.

BRIEF DESCRIPTION OF THE DRAWINGS

FIGS. 9A-9H are schematic illustrations of cross-sectional views of non-limiting exemplary fluidic channels with coated fluidic channel ceiling, sidewalls, and/or bottom.

FIG. 11A shows an image of a microwell array. The microwell array was located at the bottom of a fluidic channel of a flowcell. The ceiling and sidewalls of the fluidic channel of the flowcell had hydrophilic coatings of silicon dioxide on their surfaces. The fluidic channel bottom did not have a hydrophilic coating of silicon dioxide. The regions of the microwell array labeled 1 and 9 correspond to the regions closer to the inlet and the outlet of the flowcell respectively. FIGS. 11B-11C are images showing that the percentages of the microwells of the microwell array with bead doublets were similar at the center and the boundary of the fluidic channel for the microwell array region 1 (which was closer to the inlet of the flowcell). FIGS. 11D-11E are images showing that the percentage of the microwells of the microwell array with bead doublets was lower at the center compared to the boundary of the fluidic channel for the microwell array region 9 (which was closer to the outlet of the flowcell). FIGS. 11F-11I are plots showing the percentages of the microwells of the microwell array with no bead, single beads, or bead doublets along the flow direction.

FIGS. 12B and 12C are enlarged images of a boundary portion and a center portion of the fluidic channel, respectively, of FIG. 12A.

FIGS. 13A1-13C2 are images of a microwell array with a hydrophilic coating only at the fluidic channel ceiling (FIGS. 13A1-13A2), only at the central portions of the fluidic channel ceiling (FIGS. 13B1-13B2 and 13C1-13C2), showing further reductions in bead aggregations at the flowcell boundaries.

FIGS. 14A-14G show that minimal bead aggregation at the flowcell boundaries (FIG. 14C) and little variation in bead loading uniformity or consistency were achieved (FIGS. 14B-G) with a hydrophilic coating of silicon dioxide at the central portion of the fluidic channel ceiling which are offset from the edges formed by the fluidic channel ceiling and sidewalls. FIG. 14A is an image of a microwell array of a flowcell of a U-shaped cartridge for one loading experiment. FIGS. 14B-14C are enlarged images of portions of FIG. 14A showing that the percentages of the microwells of the microwell array with bead doublets were similar at the center and the boundary of the fluidic channel for the microwell array. FIGS. 14D-14G are plots for two loading experiments showing no edge effect with respect to the percentages of the microwells of the microwell array with no bead, single beads, or bead doublets along the flow direction.

FIGS. 15A1-15J2 each is an image of a microwell array, or a portion thereof, with a hydrophilic coating of silicon dioxide at the central portion of the fluidic channel ceiling, showing good loading efficiency, minimal bead aggregation at the flowcell boundaries, and little variation in bead loading uniformity or consistency. Each of FIGS. 15A2, 15B2, 15C2, 15D2, 15E2, 15F2, 15G2, 15H2, 15I2, 15J2 is an enlarged image of a portion of FIGS. 15A1, 15B1, 15C1, 15D1, 15E1, 15F1, 15G1, 15H1, 15I1, 15J1, respectively.

FIGS. 16A-16D show that having a hydrophilic coating at the central portion of the fluidic channel ceiling with offsets from the edges formed by the fluidic channel ceiling and sidewalls can improve loading efficiency.

DETAILED DESCRIPTION

Figure 1:
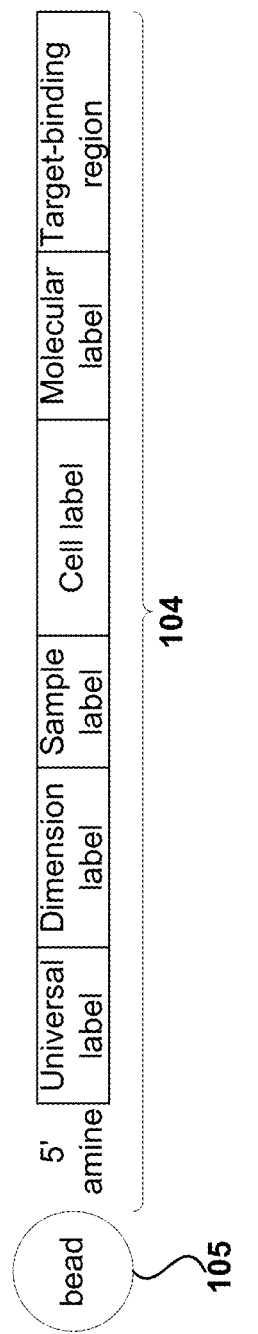
FIG. 1 illustrates a non-limiting exemplary stochastic barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Methods and systems for barcoding are disclosed. In some embodiments, a device comprises: a flowcell comprising a fluidic channel, an inlet port, and an outlet port, wherein the fluidic channel comprises a ceiling, a first sidewall, and a bottom, wherein the contact angle of the ceiling is at least 10 degrees smaller than the contact angle of the first sidewall, wherein the bottom of the fluidic channel comprises a substrate which comprises a plurality of microwells, and wherein the inlet port and the outlet port are in fluid communication with the flowcell via the fluidic channel. The fluidic channel can comprise a second sidewall. In some embodiments, the hydrophilic coating is offset from the edge formed by the ceiling and first sidewall by, for example, 100-1000 micrometers or 1%-25% of the width of the ceiling. Such a device can be used to create plug flow across the width of the flowcell chamber. Plug flow can enable efficient loading and retrieval of particles such as beads and cells into and from microwells of a microwell array at the bottom of the flowcell chamber.

A superhydrophilic coating or treatment of the top wall (also referred to as ceiling, fluidic channel ceiling, or fluidic channel ceiling) within the fluidic channel of a flowcell can be used to introduce gas plugs and buffer plugs to a flowcell with horizontal non-tilting workflow (i.e., without tilting the flowcell). The superhydrophilic coating provides capillary aided flow for a uniform fluid front of the gas and buffer plug without the use of buoyancy to achieve gas displacement by buffer or to achieve buffer displacement by the gas. Thus, the requirement to utilize buoyancy to displace the gas with buffer or to displace buffer with the gas, may be eliminated. In turn, the requirement of non-horizontal titling workflow of the flow-cell may be eliminated. In some embodiments, structured hydrophilic and hydrophobic coatings can be used on a fluidic channel ceiling or a fluidic channel ceiling to tailor the profile of a gas-buffer fluid front in a flowcell. The selective coating (also referred to as functionalization) of the fluidic channel boundary (also referred to as the flowcell boundary) influences the direction of capillary flow within specific portions of the flowcell to control the profile of the gas-buffer fluid front profile. Capillary aided flow can be utilized for horizontal operation of a flowcell with gas-buffer plug flow in order to avoid breakdown of the buffer and gas plugs. Additionally, plug flow can be utilized to achieve high flow velocities at the flowcell boundaries. One purpose for this may be to flush away excess beads on the surface of a microwell array within the flowcell.

Disclosed herein are methods for sample loading. In some embodiments, a method comprises: (a) providing a device that comprises: a flowcell comprising a fluidic channel, an inlet port, and an outlet port, wherein the fluidic channel comprises a fluidic channel ceiling, a first sidewall, and a bottom wherein the contact angle of the fluidic channel ceiling is at least 10 degrees smaller than the contact angle of the first sidewall, wherein the bottom comprises a substrate which comprises a plurality of microwells, wherein the plurality of microwells comprises at least 100 microwells, and wherein the inlet port and the outlet port are in fluid communication with the flowcell via the fluidic channel; (b) introducing a gas into the fluidic channel via the inlet port; and (c) introducing a first sample into the fluidic channel via the inlet port, wherein the first sample comprises a first plurality of particles, and wherein, after introducing the sample into the fluidic channel via the inlet port, at least 25% of the plurality of microwells each contains a single particle of the first plurality of particles. In some embodiments, at least 50% or 75% of the plurality of microwells each contains a single particle of the first plurality of particles. The fluidic channel can comprise a second sidewall.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead."

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example.

As used herein, the term "barcode" can refer to a polynucleotide sequence comprising labels. A barcode can be a polynucleotide sequence that can be used for barcoding. Barcodes, such as stochastic barcodes, can be used to quantify targets within a sample. Barcodes can be used to control for errors which may occur after a label is associated with a target. For example, a barcode can be used to assess amplification or sequencing errors. A barcode associated with a target can be called a barcode-target or barcode-tag-target.

As used herein, the term "gene-specific barcode" can refer to a polynucleotide sequence comprising labels and a target-binding region that is gene-specific.

As used herein, the term "barcoding" can refer to the random labeling (e.g., stochastic barcoding) of nucleic acids. Barcoding can utilize a recursive Poisson strategy to associate and quantify labels associated with targets. As used herein, the term "barcoding" can be used interchangeably with "gene-specific barcoding."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins. In some embodiments, targets are lipids.

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* LI.LtrB intron reverse transcriptase, the *Thermosynechococcus elongates* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

Disclosed herein are methods and system for detecting and/or correcting errors occurred during PCR and/or sequencing. The types of errors can vary, for example, include but not limited to, substitution errors (one or more bases) and non-substitution errors. Amongst the substitution errors, one-base substitution errors can occur much more frequently than those further than one-base apart. The methods and systems can be used, for example, to provide accurate counting of molecular targets by stochastic barcoding.

Barcodes

Barcoding, such as stochastic barcoding, has been described in, for example, US20150299784, WO2015031691, and Fu et al, Proc Natl Acad Sci U.S.A. 2011 May 31; 108(22):9026-31, the content of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The stochastic barcodes can be from a "non-depleting reservoirs," a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequence (e.g., a molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20 or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was stochastically barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, or 10 or more times. The dimension label can be reversibly activatable, for example, at least 1, 2, 3, 4, 5, 6, 7, 8, 9, or 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., bead), but different for different solid supports (e.g., beads). In some embodiments, at least 60%, 70%, 80%, 85%, 90%, 95%, 97%, 99% or 100% of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or at most, 1, 2, 3, 4, 5, 10, 15, 20, 25, 30, 35, 40, 45, 50, 100, 200, or 300 nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, or a droplet). In some embodiments, multiple spatial labels are used together to encode one or more positions in space.

The spatial label can be identical for all barcodes attached to a given solid support (e.g., bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or at most, $10^2$, $10^3$, $10^4$, $10^5$, $10^6$, $10^7$, $10^8$, or $10^9$, unique barcode sequences. The unique molecular label sequences can be attached to a given solid support (e.g., bead).

A barcode can be, or be about, 1, 2, 3, 4, 5, 10, 15, 20, 25, 30, 35, 40, 45, 50, or a number or a range between any two of these values, nucleotides in length. A barcode can be at least, or at most, 1, 2, 3, 4, 5, 10, 15, 20, 25, 30, 35, 40, 45, 50, 100, 200, or 300 nucleotides in length.

Molecular Labels

A stochastic barcode can comprise one or more molecular labels. Molecular labels can include barcode sequences. In some embodiments, a molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region).

In some embodiments, a diverse set of molecular labels are attached to a given solid support (e.g., bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. Stochastic barcodes with the unique molecular label sequences can be attached to a given solid support (e.g., bead).

For stochastic barcoding using a plurality of stochastic barcodes, the ratio of the number of different molecular label sequences and the number of occurrence of any of the targets can be, or about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g. target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g. an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A barcode can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be stochastically labeled. The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Solid Supports

Barcodes, such as stochastic barcodes, disclosed herein can, in some embodiments, be associated with a solid support. The solid support can be, for example, a synthetic particle. In some embodiments, some or all of the barcode sequence, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer.

In some embodiments, the bead can be a polymeric bead, for example a deformable bead or a gel bead, functionalized with barcodes or stochastic barcodes (such as gel beads from 10× Genomics (San Francisco, Calif.). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
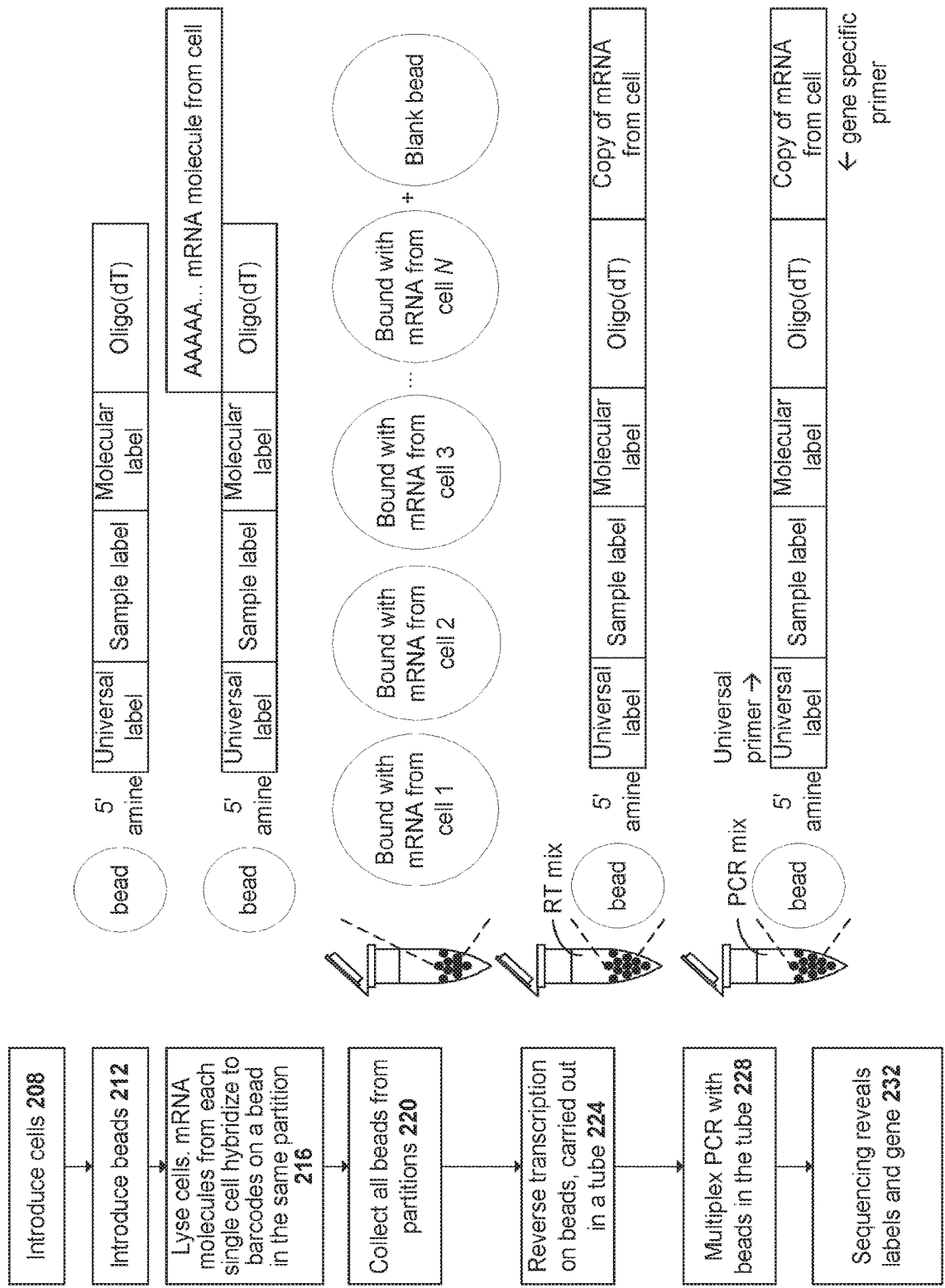
FIG. 2 shows a non-limiting exemplary workflow of stochastic barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode sequences of different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, stochastically barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized" are used interchangeably, and can refer to covalent or non-covalent means for attaching barcodes to a solid support. Any of a variety of different solid supports can be used as solid supports for attaching pre-synthesized barcodes or for in situ solid-phase synthesis of barcodes.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

The size of a particle can vary. For example, the diameter of the particle can range from 0.1 micrometer to 50 micrometer. In some embodiments, the diameters of particles can be, or be about, 0.1, 0.5, 1, 2, 3, 4, 5, 6, 7, 8, 9, 10, 20, 30, 40, 50 micrometer, or a number or a range between any two of these values.

The diameter of the particle can be related to the diameter of the wells of the substrate. In some embodiments, the diameter of the particle can be, or be about, 10%, 20%, 30%, 40%, 50%, 60%, 70%, 80%, 90%, 100%, or a number or a range between any two of these values, longer or shorter than the diameter of the well. In some embodiments, the diameter of the particle can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell.

A particle can be attached to and/or embedded in a substrate. A particle can be attached to and/or embedded in a gel, hydrogel, polymer and/or matrix. The spatial position of a particle within a substrate (e.g., gel, matrix, scaffold, or polymer) can be identified using the spatial label present on the barcode on the particle which can serve as a location address.

Examples of particles can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A particle can be associated with (e.g. impregnated with) quantum dots or fluorescent dyes to make it fluorescent in one fluorescence optical channel or multiple optical channels. A particle can be associated with iron oxide or chromium oxide to make it paramagnetic or ferromagnetic. Particles can be identifiable. For example, a particle can be imaged using a camera. A particle can have a detectable code associated with the particle. For example, a particle can comprise a barcode. A particle can change size, for example due to swelling in an organic or inorganic solution. A particle can be hydrophobic. A particle can be hydrophilic. A particle can be biocompatible.

A solid support (e.g., a particle) can be visualized. The solid support can comprise a visualizing tag (e.g., fluorescent dye). A solid support (e.g., a particle) can be etched with an identifier (e.g., a number). The identifier can be visualized through imaging the particles.

Substrates and Microwell Arrays

As used herein, a substrate can refer to a type of solid support. A substrate can refer to a solid support that can comprise stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., bead). In some embodiments, a microwell can contain a single particle (e.g., a cell or a bead). In some embodiments, a microwell can contain two different particles (e.g., a cell and a bead).

Microwell Shapes

Microwells can be fabricated in a variety of shapes. Non-limiting exemplary well geometries can include cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells can comprise a shape that combines two or more of these geometries. For example, a microwell can be partly cylindrical, with the remainder having the shape of an inverted cone. A microwell can include two side-by-side cylinders, one of larger diameter (e.g. that corresponds roughly to the diameter of the beads) than the other (e.g. that corresponds roughly to the diameter of the cells), that are connected by a vertical channel (that is, parallel to the cylinder axes) that extends the full length (depth) of the cylinders. The location of the opening of the microwell can vary. For example, the opening of the microwell can be at the upper surface of the substrate. For example, the opening of the microwell can be at the lower surface of the substrate. The shape of the close end, for example the bottom, of the microwell can vary. For example, the closed end of the microwell can be flat. For example, the closed end of the microwell can have a curved surface (e.g., convex or concave). The shape and/or size of the microwell can be determined based on the types of cells or solid supports to be trapped within the microwells. In some embodiments, a microwell can have a non-circular cross section (e.g., square or hexagonal) in a plane of the substrate.

Microwell Sizes

Microwells can be fabricated in a variety of sizes. Microwell size can be characterized, for example, in terms of the diameter and/or the depth of the microwells. The diameter of the microwell can refer to the largest circle that can be inscribed within the planar cross-section of the microwell geometry. The diameter of the microwells can, in some embodiments, range from about 1-fold to about 10-folds the diameter of the cells or solid supports to be trapped within the microwells. In some embodiments, the microwell diameter can be, or be about, 1-fold, 1.5-fold, 2-folds, 3-folds, 4-folds, 5-folds, 6-folds, 7-folds, 8-folds, 9-files, 10-folds, or a number or a range between any two of these values, the diameter of the cells or the solid supports to be trapped within the microwells. In some embodiments, the microwell diameter can be at least, or at most, 1-fold, 1.5-fold, 2-folds, 3-folds, 4-folds, 5-folds, 6-folds, 7-folds, 8-folds, 9-files, 10-folds the diameter of the cells or the solid supports to be trapped within the microwells. In some embodiments, the microwell diameter can be about 2.5-folds the diameter of the cells or solid supports to be trapped within the microwells.

The diameter of a microwell can be specified in terms of absolute dimensions. The diameter of a microwell can range from about 1 nanometer to about 1000 micrometers. In some embodiments, the microwell diameter can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter can be, or be about, 1, 2, 3, 4, 5, 6, 7, 8, 9 10, 20, 30, 40, 50, 60, 70, 80, 90, 100, 200, 300, 400, 500, 600, 700, 800, 900, 1000 micrometers, or a number or a range between any two of these values. In some embodiments, the microwell diameter can be at least, or at most 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell diameter can be about 30 micrometers.

The depth of the microwell can vary, for example, to provide efficient trapping of droplets, for example cells and solid supports, or to provide efficient exchange of assay buffers and other reagents contained within the wells. The ratio of diameter to depth (i.e. aspect ratio) can be varied such that once a cell and/or a solid support settle inside a microwell, they will not be displaced by fluid motion above the microwell. In some embodiments, the depth of the microwell can be smaller than the diameter of the bead. For example, the depth of the microwell can be, or be about, 5%, 10%, 20%, 30%, 40%, 50%, 60%, 70%, 80%, 90%, 99%, 99.9%, 100%, or a number or a range between any two of these values, of the diameter of the bead. For example, the depth of the microwell can be at least, or at most, 5%, 10%, 20%, 30%, 40%, 50%, 60%, 70%, 80%, 90%, 99%, 99.9%, 100% of the diameter of the bead. In some embodiments, synthetic particles such as beads can protrude outside of the microwells.

In some embodiments, a dimension of a microwell allows the microwell to contain at most one bead. A ratio of the width of the microwell to a diameter of the bead can vary, ranging from 1-1.9. In some embodiments, the ratio of the width of the microwell to the diameter of the bead can be, or be about, 1, 1.1, 1.2, 1.3, 1.4, 1.5, 1.6, 1.7, 1.8, 1.9, or a number or a range between any two of these values. In some embodiments, the ratio of the width of the microwell to the diameter of the bead can be at least, or at most, 1, 1.1, 1.2, 1.3, 1.4, 1.5, 1.6, 1.7, 1.8, or 1.9.

The dimensions of a microwell can vary such that the microwell has sufficient space to accommodate a solid support and a cell of various sizes without being dislodged by fluid motion above the microwell. The depth of a microwell can range from about 1-fold to about 10-folds the diameter of the cells or solid supports to be trapped within the microwells. In some embodiments, the microwell depth can be, or be about, 1-fold, 1.5-fold, 2-folds, 3-folds, 4-folds, 5-folds, 6-folds, 7-folds, 8-folds, 9-files, 10-folds, or a number or a range between any two of these values, the diameter of the cells or solid supports to be trapped within the microwells. In some embodiments, the microwell depth can be at least, or at most, 1-fold, 1.5-fold, 2-folds, 3-folds, 4-folds, 5-folds, 6-folds, 7-folds, 8-folds, 9-files, or 10-folds the diameter of the cells or solid supports to be trapped within the microwells. In some embodiments, the microwell depth can be about 2.5-folds the diameter of the cells or solid supports to be trapped within the microwells.

An aspect ratio of the width of the microwell to the depth of the microwell can vary, for example ranging from 0.1-2. In some embodiments, the aspect ratio of the width of the microwell to the depth of the microwell can be, or be about, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, or a number or a range between any two of these values. In some embodiments, the aspect ratio of the width of the microwell to the depth of the microwell can be at least, or at most, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2.

The depth of a microwell can be specified in terms of its absolute dimension. For example, the depth of a microwell can range from about 1 nanometer to about 1000 micrometers. In some embodiments, the microwell depth can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be, or be about, 1, 2, 3, 4, 5, 6, 7, 8, 9 10, 20, 30, 40, 50, 60, 70, 80, 90, 100, 200, 300, 400, 500, 600, 700, 800, 900, 1000 micrometers, or a number or a range between any two of these values. In some embodiments, the microwell depth can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers. In some embodiments, the microwell depth can be about 30 micrometers.

The volume of a microwell can vary, for example ranging from about 1 picoliter to about 1000 microliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, picoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 picoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, nanoliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nanoliters. In some embodiments, the microwell volume can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, microliters. In some embodiments, the microwell volume can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the microwell volume can be about 1 microliter.

The volume of a microwell can be characterized in terms of the variation in volume from one microwell to another. The coefficient of variation (expressed as a percentage) for microwell volume can range from about 1% to about 100%. The coefficient of variation for microwell volume can be, or be about, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. The coefficient of variation for microwell volume can be, at least or at most, 1%, 2%, 3%, 4%, 5%, 6%, 7%, 8%, 9%, 10%, 20%, 30%, 40%, 50%, 60%, 70%, 80%, 90%, or 100%. In some embodiments, the coefficient of variation of microwell volume can be about 2.5%.

The ratio of the volume of a microwell to the surface area of a bead (or to the surface area of a solid support to which stochastic barcode oligonucleotides can be attached) can vary, for example range from about 2.5 to about 1520 micrometers. In some embodiments, the ratio can be, or be about, 2.5, 5, 10, 100, 500, 750, 1000, 1520 micrometers, or a number or a range between any two of these values. In some embodiments, the ratio can be at least, or at most, 2.5, 5, 10, 100, 500, 750, 1000, or 1520 micrometers. In some embodiments, the ratio can be about 67.5 micrometers.

Microwell Arrangements

Microwells can be arranged in a one dimensional, two dimensional, or three-dimensional array. A three dimensional array can be achieved, for example, by stacking a series of two or more two dimensional arrays, for example by stacking two or more substrates comprising microwell arrays.

The pattern and spacing between microwells can vary to optimize the efficiency of trapping a single cell and a single solid support (e.g., bead) in each well, as well as to maximize the number of wells per unit area of the array. The microwells can be distributed according to a variety of random or non-random patterns. For example, they can be distributed entirely randomly across the surface of the array substrate, or they can be arranged in a square grid, rectangular grid, hexagonal grid, or the like.

The center-to-center distance or the center-to-center spacing between wells can vary from about 1 micrometer to about 1000 micrometers. In some embodiments, the center-to-center distance between wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the center-to-center distance between wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the center-to-center distance between wells can be about 4890 micrometers.

The distance or the spacing between the edges of the microwells can vary from about 1 micrometer to about 1000 micrometers. In some embodiments, the distance between the edges of the wells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the distance between the edges of the wells can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers. In some embodiments, the distance between the edges of the wells can be about 80 micrometers.

Microwell Density

A microwell array can comprise microwells at varying densities, for example ranging from 100 microwells per inch$^2$ to 1000000 microwells per inch$^2$. In some embodiments, the density of the microwell array can be, or be about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, or a number or a range between any two of these values, microwells per inch$^2$. In some embodiments, the density of the microwell array can be at least, or at most, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, or 10000000 microwells per inch$^2$. In some embodiments, the density of the microwell array can be, or be about, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values, microwells per cm$^2$. In some embodiments, the density of the microwell array can be at least, or at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 microwells per cm$^2$.

The total number of microwells on a substrate can vary based on the pattern and the spacing of the wells and the overall dimensions of the array. The number of microwells in the array can vary, for example, ranging from about 96 to about 1000000. In some embodiments, the number of microwells in the microarray can be, or be about, 96, 384, 1536, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, $10^8$, $10^9$, or a number or a range between any two of these values. In some embodiments, the number of microwells in the microarray can be at least, or at most, 96, 384, 1536, 2000, 3000, 4000, 5000, 6000, 7000, 8000, 9000, 10000, 20000, 30000, 40000, 50000, 60000, 70000, 80000, 90000, 100000 200000, 300000, 400000, 500000, 600000, 700000, 800000, 900000, 1000000, 2000000, 3000000, 4000000, 5000000, 6000000, 7000000, 8000000, 9000000, 10000000, $10^8$, $10^9$. In some embodiments, the number of microwells in the microwell array can be about 96. In some embodiments, the number of microwells can be about 150000.

Microwell Array Surface Features

A microwell array can comprise surface features between the microwells that are designed to help guide cells and solid supports into the wells and/or to prevent them from settling on the surfaces between wells. Non-limiting examples of suitable surface features include, but are not limited to, domed, ridged, or peaked surface features that encircle the wells or straddle the surface between wells.

Substrate Fabrication Techniques

A microwell can be fabricated using any of a number of fabrication techniques. Non-limiting examples of fabrication methods that can be used include bulk micromachining techniques such as photolithography and wet chemical etching, plasma etching, or deep reactive ion etching; micromolding and micro-embossing; laser micromachining; 3D printing or other direct write fabrication processes using curable materials; and similar techniques.

Microwell arrays can be fabricated from a variety of substrate materials. The choice of material can depend on the choice of fabrication technique, and vice versa. Non-limiting examples of suitable materials include fused-silica, glass, polymers (e.g. agarose, gelatin, hydrogels, polydimethylsiloxane (PDMS) elastomer, polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, thiol-ene based resins, metals or metal films (e.g. aluminum, stainless steel, copper, nickel, chromium, and titanium), and the like. A hydrophilic material can be desirable for fabrication of the microwell arrays (e.g. to enhance wettability and minimize non-specific binding of cells and other biological material). Hydrophobic materials that can be treated or coated (e.g. by oxygen plasma treatment, or grafting of a polyethylene oxide surface layer) can be used for fabrication of the microwell arrays. The use of porous, hydrophilic materials for the fabrication of the microwell array can be desirable in order to facilitate capillary wicking/venting of entrapped gas or air bubbles in the device. The microwell array can be fabricated from a single material. The microwell array can comprise two or more different materials that have been bonded together or mechanically joined.

Substrate Shapes and Sizes

A substrate can have variety of shapes and sizes. For example, the shape (or footprint) of the substrate within which microwells are fabricated can be square, rectangular, circular, or irregular in shape. The size of can be characterized by its width, length, and depth.

The width of a substrate can vary, ranging from 0.1 inch to 10 inches. In some embodiments, the width of the substrate can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the width of the substrate can be at least, or at most, 0.1, 0.2, 0.3, 0.4, 05, 0.6, 0.7, 0.8, 0.9, 1, 2, 3, 4, 5, 6, 7, 8, 9, or 10 inches. The width of the substrate can vary, ranging from 0.2 centimeter to 20 centimeters. In some embodiments, the width of the substrate can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the width of the substrate can be at least, or at most, 0.2, 0.3, 0.4, 05, 0.6, 0.7, 0.8, 0.9, 1, 2, 3, 4, 5, 6, 7, 8, 9, 10, or 20 centimeters.

The length of a substrate can vary, ranging from 0.1 inch to 10 inches. In some embodiments, the length of the substrate can be, or be about, 0.1, 0.2, 0.3, 0.4, 05, 0.6, 0.7, 0.8, 0.9, 1, 2, 3, 4, 5, 6, 7, 8, 9, 10 inches, or a number or a range between any two of these values. In some embodiments, the length of the substrate can be at least, or at most, 0.1, 0.2, 0.3, 0.4, 05, 0.6, 0.7, 0.8, 0.9, 1, 2, 3, 4, 5, 6, 7, 8, 9, or 10 inches. The length of the substrate can vary, ranging from 0.2 centimeter to 20 centimeters. In some embodiments, the length of the substrate can be, or be about, 0.2, 0.2, 0.3, 0.4, 05, 0.6, 0.7, 0.8, 0.9, 1, 2, 3, 4, 5, 6, 7, 8, 9, 10, 20 centimeters, or a number or a range between any two of these values. In some embodiments, the length of the substrate can be at least, or at most, 0.2, 0.3, 0.4, 05, 0.6, 0.7, 0.8, 0.9, 1, 2, 3, 4, 5, 6, 7, 8, 9, 10, or 20 centimeters.

In some embodiments, the footprint of a substrate, for example defined by its width and length, can be similar to that of a microtiter plate. In some embodiments, the footprint of the microwell array substrate can be similar to that of standard microscope slides. Non-limiting examples of the footprint of standard microscope slides include about 75 mm long×25 mm wide (about 3" long×about 1" wide) and about 75 mm long×50 mm wide (about 3" long×2" wide).

The thickness of the substrate within which the microwells are fabricated can range from about 0.1 mm thick to about 10 mm thick, or more. The thickness of the microwell array substrate can be, or be about, 0.1, 0.5, 1, 2, 3, 4, 5, 6, 7, 8, 9, 10 mm, or a number or a range between any two of these values. The thickness of the microwell array substrate can be at least, or at most, 10, 9, 8, 7, 6, 5, 4, 3, 2, 1, 0.5, 0.1 mm. The thickness of the microwell array substrate can be about 1 mm thick. The thickness of the microwell array substrate can be any value within these ranges, for example, the thickness of the microwell array substrate can be between about 0.2 mm and about 9.5 mm.

Microwell Array Surface Treatments

A variety of surface treatments and surface modification techniques can be used to modify the properties of microwell array surfaces. Examples include, but are not limited to, oxygen plasma treatments to render hydrophobic material surfaces more hydrophilic, the use of wet or dry etching techniques to smooth or roughen glass and silicon surfaces, adsorption or grafting of polyethylene oxide or other polymer layers, for example pluronic, or bovine serum albumin to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells can be used to covalently couple oligonucleotide probes, peptides, proteins, or other biomolecules to the walls of the microwells. The choice of surface treatment or surface modification utilized can depend on the type of surface property that is desired and/or on the type of material from which the microwell array is made.

Microwell Sealing

The openings of microwells can be sealed, for example, during cell lysis steps to prevent cross hybridization of target nucleic acid between adjacent microwells. A microwell (or array of microwells) can be sealed or capped using, for example, a flexible membrane or sheet of solid material (i.e. a plate or platten) that clamps against the surface of the microwell array substrate, or a suitable bead, where the diameter of the bead is larger than the diameter of the microwell.

A seal formed using a flexible membrane or sheet of solid material can comprise, for example, inorganic nanopore membranes (e.g., aluminum oxides), dialysis membranes, glass slides, coverslips, elastomeric films (e.g. PDMS), or hydrophilic polymer films (e.g., a polymer film coated with a thin film of agarose that has been hydrated with lysis buffer).

Solid supports (e.g., beads) used for capping the microwells can comprise any of the solid supports (e.g., beads) of the disclosure. In some embodiments, the solid supports are cross-linked dextran beads (e.g., Sephadex). Cross-linked dextran can range from about 10 micrometers to about 80 micrometers. In some embodiments, the cross-linked dextran beads used for capping can be, or be about, 10, 20, 30, 40, 50, 60, 70, 80 micrometers, or a number or a range between any two of these values. In some embodiments, the cross-linked dextran beads used for capping can be at least, or at most, 10, 20, 30, 40, 50, 60, 70, or 80 micrometers. The beads can be larger than the diameters of the microwells. In some embodiments, the beads can be, or be about, 10%, 20%, 30%, 40%, 50%, 60%, 70%, 80%, 90%, 99%, or a number or a range between any two of these values, larger than the diameter of the microwells. In some embodiments, the beads can be at least, or at most, 10%, 20%, 30%, 40%, 50%, 60%, 70%, 80%, 90%, or 99%, larger than the diameter of the microwells.

The seal or cap can allow buffer to pass into and out of the microwells, while preventing macromolecules (e.g., nucleic acids) from migrating out of the well. In some embodiments, a macromolecule of or of about 1, 2, 3, 4, 5, 6, 7, 8, 9, 10, 12, 13, 14, 15, 16, 17, 18, 19, 20, or a number or a range between any two of these values, nucleotides can be blocked from migrating into or out of the microwell by the seal or cap. In some embodiments, a macromolecule of at least, or at most, 1, 2, 3, 4, 5, 6, 7, 8, 9, 10, 12, 13, 14, 15, 16, 17, 18, 19, or 20 nucleotides can be blocked from migrating into or out of the microwell by the seal or cap.

Solid Support Manipulation

Solid supports (e.g., synthetic particles or beads) can be distributed among a substrate. Solid supports can be distributed among wells of the substrate, removed from the wells of the substrate, or otherwise transported through a device comprising one or more microwell arrays by means of centrifugation or other non-magnetic means. A microwell of a substrate can be pre-loaded with a solid support. A microwell of a substrate can hold or can hold about 1, 2, 3, 4, 5, 6, 7, 8, 9, 10 solid supports. A microwell of a substrate can hold at least, or at most, 1, 2, 3, 4, 5, 6, 7, 8, 9, 10 solid supports. In some embodiments, a microwell of a substrate can hold one solid support.

Consumables

Microwell arrays can be a consumable component of the assay system. Microwell arrays can be reusable. Microwell arrays can be configured for use as a stand-alone device for performing assays manually, or they can be configured to comprise a fixed or removable component of an instrument system that provides for full or partial automation of the assay procedure. In some embodiments of the disclosed methods, the bead-based libraries of stochastic barcodes can be deposited in the wells of the microwell array as part of the assay procedure. In some embodiments, the beads can be pre-loaded into the wells of the microwell array and provided to the user as part of, for example, a kit for performing stochastic barcoding and digital counting of nucleic acid targets.

Two Mated Microwell Arrays

In some embodiments, two mated microwell arrays can be provided, one pre-loaded with beads which are held in place by a first magnet, and the other for use by the user in loading individual cells. Following distribution of cells into the second microwell array, the two arrays can be placed face-to-face and the first magnet removed while a second magnet is used to draw the beads from the first array down into the corresponding microwells of the second array, thereby ensuring that the beads rest above the cells in the second microwell array and thus minimizing diffusional loss of target molecules following cell lysis, while maximizing efficient attachment of target molecules to the stochastic barcodes on the bead.

Substrates without Microwells

In some embodiments, a substrate does not include microwells. For example, beads can be assembled. For example, beads can be self-assembled. The beads can self-assemble into a monolayer. The monolayer can be on a flat surface of the substrate. The monolayer can be on a curved surface of the substrate. The bead monolayer can be formed by any method, such as alcohol evaporation.

Individual cells and beads can be compartmentalized using alternatives to microwells, for example, a single solid support and a single cell could be confined within a single droplet in an emulsion (e.g. in a droplet digital microfluidic system).

Cells could be confined within porous beads that themselves comprise the plurality of tethered stochastic barcodes. Individual cells and solid supports can be compartmentalized in any type of container, microcontainer, reaction chamber, reaction vessel, or the like.

Single cell, stochastic barcoding can be performed without the use of microwells. Single cell, stochastic barcoding assays can be performed without the use of any physical container. For example, stochastic barcoding without a physical container can be performed by embedding cells and beads in close proximity to each other within a polymer layer or gel layer to create a diffusional barrier between different cell/bead pairs. For example, stochastic barcoding without a physical container can be performed in situ, in vivo, on an intact solid tissue, on an intact cell, and/or subcellularly.

Methods of Barcoding

Provided herein are methods for estimating the number of distinct targets at distinct locations in a physical sample (e.g., tissue, organ, tumor, cell). The methods can comprise placing the stochastic barcodes in close proximity with the sample, lysing the sample, associating distinct targets with the stochastic barcodes, amplifying the targets and/or digitally counting the targets. The method can further comprise analyzing and/or visualizing the information obtained from the spatial labels on the stochastic barcodes. In some embodiments, the method comprises visualizing the plurality of targets in the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after stochastically barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, stochastically barcoding the plurality of targets comprises hybridizing a plurality of stochastic barcodes with a plurality of targets to create stochastically barcoded targets. Stochastically barcoding the plurality of targets can comprise generating an indexed library of the stochastically barcoded targets. Generating an indexed library of the stochastically barcoded targets can be performed with a solid support comprising the plurality of stochastic barcodes.

Contacting a Sample and Stochastic Barcode(s)

The disclosure provides for methods for contacting a sample (e.g., cells) to a substrate of the disclosure. A sample comprising, for example, a cell, organ, or tissue thin section, can be contacted to stochastic barcodes. The cells can be contacted, for example, by gravity flow wherein the cells can settle and create a monolayer. The sample can be a tissue thin section. The thin section can be placed on the substrate. The sample can be one-dimensional (e.g., form a planar surface). The sample (e.g., cells) can be spread across the substrate, for example, by growing/culturing the cells on the substrate.

When stochastic barcodes are in close proximity to targets, the targets can hybridize to the stochastic barcode. The stochastic barcodes can be contacted at a non-depletable ratio such that each distinct target can associate with a distinct stochastic barcode of the disclosure. To ensure efficient association between the target and the stochastic barcode, the targets can be crosslinked to the stochastic barcode.

Cell Lysis

Following the distribution of cells and stochastic barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SOS, Li dodecyl sulfate, Triton™ X-100, Tween®-20, or NP-40), an organic solvent (e.g. methanol or acetone), or digestive enzymes (e.g. proteinase K, pepsin, or trypsin), or any combination thereof. To increase the association of a target and a stochastic barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 NA or more Tris HCL. A lysis buffer can comprise about 0.1 M Tris HCl. The pH of the lysis buffer can be at least about 1, 2, 3, 4, 5, 6, 7, 8, 9, or 10 or more. The pH of the lysis buffer can be at most about 1, 2, 3, 4, 5, 6, 7, 8, 9, or 10 or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, Triton™ X, Tween®, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7% or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1 M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Stochastic Barcodes to Target Nucleic Acid Molecules

Following lysis of the cells and release of nucleic acid molecules therefrom, the nucleic acid molecules can randomly associate with the stochastic barcodes of the co-localized solid support. Association can comprise hybridization of a stochastic barcode's target recognition region to a complementary portion of the target nucleic acid molecule (e.g., oligo(dT) of the stochastic barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of stochastic barcoding illustrated in FIG. 2, at 216, mRNA molecules can hybridize to stochastic barcodes on beads. For example, single-stranded nucleotide fragments can hybridize to the target-binding regions of stochastic barcodes.

Attachment can further comprise ligation of a stochastic barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The stochastic barcode can then be ligated to any nucleic acid molecule comprising a sequence complementary to the restriction site overhang. A ligase (e.g., T4 DNA ligase) can be used to join the two fragments.

For example, in a non-limiting example of stochastic barcoding illustrated in FIG. 2, at 220, the labeled targets from a plurality of cells (or a plurality of samples) (e.g., target-barcode molecules) can be subsequently pooled, for example, into a tube. The labeled targets can be pooled by, for example, retrieving the stochastic barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for methods to create a stochastic target-barcode conjugate using reverse transcription (e.g., in 224 of FIG. 2). The stochastic target-barcode conjugate can comprise the stochastic barcode and a complementary sequence of all or a portion of the target nucleic acid (i.e. a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular and/or molecular label. The amplification reactions can comprise amplifying at least a portion of a sample tag, a cell label, a spatial label, a molecular label, a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a molecular label.

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a stochastically labeled-amplicon. The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a molecular label. The stochastically labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of stochastically labeled targets. The one or more primers can anneal to the 3' end or 5' end of the plurality of stochastically labeled targets. The one or more primers can anneal to an internal region of the plurality of stochastically labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of stochastically labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a molecular label, a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total stochastically labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and molecular label on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, stochastically barcoding the plurality of targets in the sample further comprises generating an indexed library of the stochastically barcoded fragments. The molecular labels of different stochastic barcodes can be different from one another. Generating an indexed library of the stochastically barcoded targets includes generating a plurality of indexed polynucleotides from the plurality of targets in the sample. For example, for an indexed library of the stochastically barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the stochastically barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the stochastically barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at 232 of FIG. 2.

Figure 3:
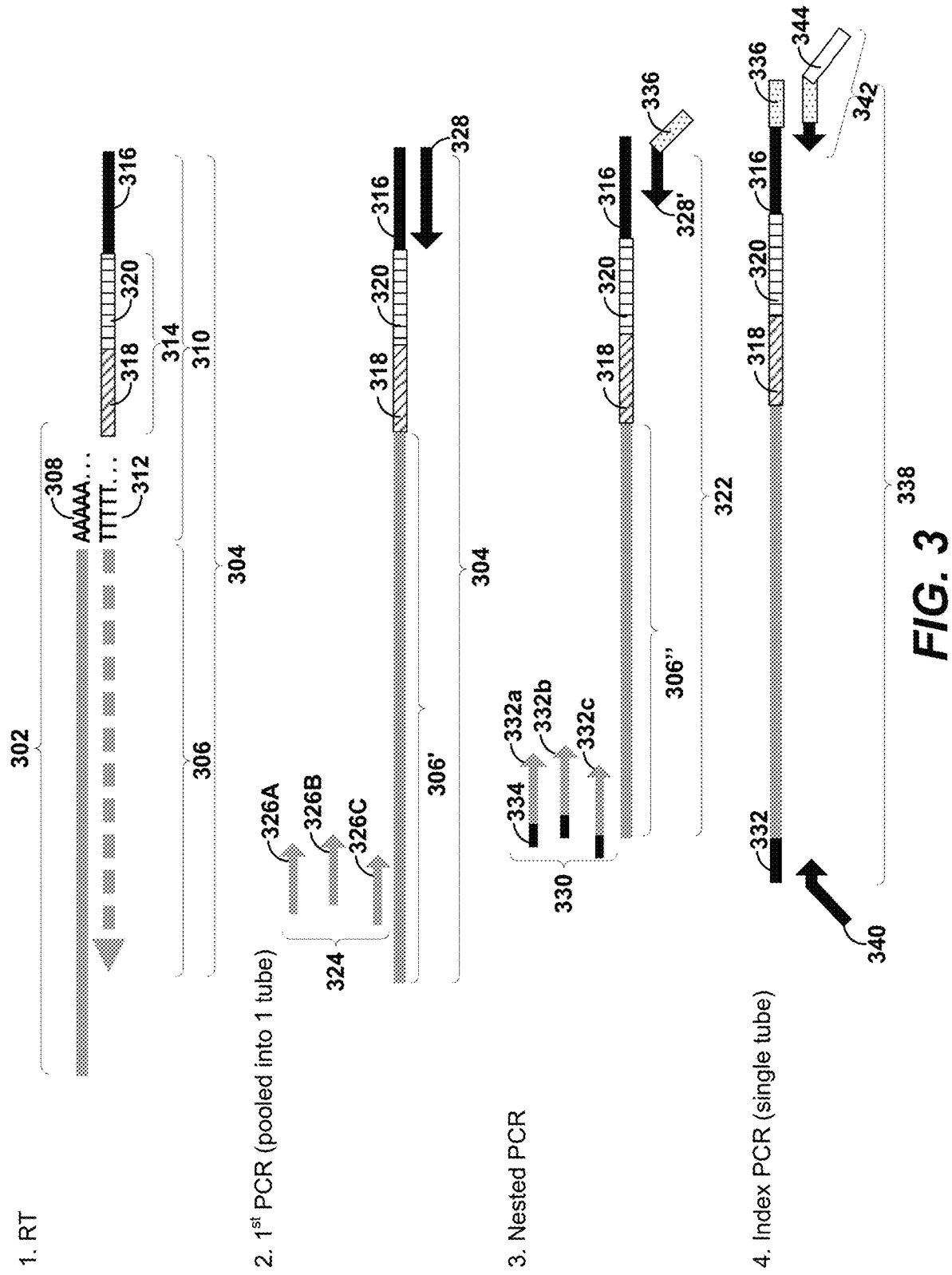
FIG. 3 is a schematic illustration showing a non-limiting exemplary process for generating an indexed library of the stochastically barcoded targets from a plurality of targets.

FIG. 3 is a schematic illustration showing a non-limiting exemplary process of generating an indexed library of the stochastically barcoded targets, for example mRNAs. As shown in step 1, the reverse transcription process can encode each mRNA molecule with a unique molecular label, a cell label, and a universal PCR site. In particular, RNA molecules 302 can be reverse transcribed to produce labeled cDNA molecules 304, including a cDNA region 306, by the stochastic hybridization of a set of molecular identifier labels 310 to the poly(A) tail region 308 of the RNA molecules 302. Each of the molecular identifier labels 310 can comprise a target-binding region, for example a poly (dT) region 312, a label region 314, and a universal PCR region 316.

In some embodiments, the cell label can include 3 to 20 nucleotides. In some embodiments, the molecular label can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a molecular label 318 and a cell label 320. In some embodiments, the label region 314 can include one or more of a universal label, a dimension label, and a cell label. The molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of molecular identifier labels 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, molecular identifier labels 310. And the set of molecular identifier labels 310 can, for example, each contain a unique label region 314. The labeled cDNA molecules 304 can be purified to remove excess molecular identifier labels 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise $1^{st}$ PCR primer pool 324 of custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the 2$^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of molecular identifier labels 318 can be sequenced in one sequencing reaction using next generation sequencing (NGS).

Sequencing

In some embodiments, estimating the number of different stochastically barcoded targets can comprise determining the sequences of the labeled targets, the spatial label, the molecular label, the sample label, the cell label, or any product thereof (e.g. labeled-amplicons, or labeled-cDNA molecules). An amplified target can be subjected to sequencing. Determining the sequence of the stochastically barcoded target or any product thereof can comprise conducting a sequencing reaction to determine the sequence of at least a portion of a sample label, a spatial label, a cell label, a molecular label, at least a portion of the stochastically labeled target, a complement thereof, a reverse complement thereof, or any combination thereof.

Determination of the sequence of a stochastically barcoded target (e.g. amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the stochastically barcoded target or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the stochastically barcoded target or any product thereof can be determined by electron microscopy or a chemical-sensitive field effect transistor (chemFET) array.

High-throughput sequencing methods, such as cyclic array sequencing using platforms such as Roche 454™, lumina Solexa®, ABI-SOLID™, ION Torrent®, Complete Genomics, Pacific Bioscience, Helicos, or the Polonator platform, can be utilized. In some embodiment, sequencing can comprise MiSeq sequencing. In some embodiment, sequencing can comprise HiSeq sequencing.

The stochastically labeled targets can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the stochastically barcoded targets comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly(T) tail by capturing the mRNAs from the sample.

Determining the sequences of the spatial labels and the molecular labels of the plurality of the stochastic barcodes can include sequencing 0.00001%, 0.0001%, 0.001%, 0.01%, 0.1%, 1%, 2%, 3%, 4%, 5%, 6%, 7%, 8%, 9%, 10%, 20%, 30%, 40%, 50%, 60%, 70%, 80%, 90%, 99%, 100%, or a number or a range between any two of these values, of the plurality of stochastic barcodes. Determining the sequences of the labels of the plurality of stochastic barcodes, for example the sample labels, the spatial labels, and the molecular labels, can include sequencing 1, 10, 20, 30, 40, 50, 60, 70, 80, 90, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or a number or a range between any two of these values, of the plurality of stochastic barcodes. Sequencing some or all of the plurality of stochastic barcodes can include generating sequences with read lengths of, of about, of at least, or of at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, of nucleotides or bases.

Sequencing can comprise sequencing at least or at least about 10, 20, 30, 40, 50, 60, 70, 80, 90, 100 or more nucleotides or base pairs of the stochastically barcoded targets. For example, sequencing can comprise generating sequencing data with sequences with read lengths of 50, 75, or 100, or more nucleotides by performing polymerase chain reaction (PCR) amplification on the plurality of stochastically barcoded targets. Sequencing can comprise sequencing at least or at least about 200, 300, 400, 500, 600, 700, 800, 900, 1,000 or more nucleotides or base pairs of the stochastically barcoded targets. Sequencing can comprise sequencing at least or at least about 1500, 2000, 3000, 4000, 5000, 6000, 7000, 8000, 9000, or 10000 or more nucleotides or base pairs of the stochastically barcoded targets.

Sequencing can comprise at least about 200, 300, 400, 500, 600, 700, 800, 900, 1,000 or more sequencing reads per run. In some embodiments, sequencing comprises sequencing at least or at least about 1500, 2000, 3000, 4000, 5000, 6000, 7000, 8000, 9000, or 10000 or more sequencing reads per run. Sequencing can comprise less than or equal to about 1,600,000,000 sequencing reads per run. Sequencing can comprise less than or equal to about 200,000,000 reads per run.

Samples

In some embodiments, the plurality of targets can be comprised in one or more samples. A sample can comprise one or more cells, or nucleic acids from one or more cells. A sample can be a single cell or nucleic acids from a single cell. The one or more cells can be of one or more cell types. At least one of the one or more cell types can be brain cell, heart cell, cancer cell, circulating tumor cell, organ cell, epithelial cell, metastatic cell, benign cell, primary cell, circulatory cell, or any combination thereof.

A sample for use in the method of the disclosure can comprise one or more cells. A sample can refer to one or more cells. In some embodiments, the plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some embodiments, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma. The sample can include a tissue, a cell monolayer, fixed cells, a tissue section, or any combination thereof. The sample can include a biological sample, a clinical sample, an environmental sample, a biological fluid, a tissue, or a cell from a subject. The sample can be obtained from a human, a mammal, a dog, a rat, a mouse, a fish, a fly, a worm, a plant, a fungus, a bacterium, a virus, a vertebrate, or an invertebrate.

In some embodiments, the cells are cells that have been infected with virus and contain viral oligonucleotides. In some embodiments, the viral infection can be caused by a virus such as single-stranded (+ strand or "sense") DNA viruses (e.g. parvoviruses), or double-stranded RNA viruses (e.g. reoviruses). In some embodiments, the cells are bacteria. These can include either gram-positive or gram-negative bacteria. In some embodiments, the cells are fungi. In some embodiments, the cells are protozoans or other parasites.

As used herein, the term "cell" can refer to one or more cells. In some embodiments, the cells are normal cells, for example, human cells in different stages of development, or human cells from different organs or tissue types. In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Devices

Disclosed herein are devices for stochastic barcoding. In some embodiments, a device comprises: a flowcell comprising a fluidic channel, an inlet port, and an outlet port, wherein the fluidic channel comprises a ceiling, a fluidic channel sidewall, and a bottom. This other fluidic channel sidewall forms an edge with the ceiling and another edge with the bottom. The contact angle of the ceiling can be at least 10 degrees smaller than the contact angle of the fluidic channel sidewall. The bottom of the fluidic channel comprises a substrate which comprises a plurality of microwells. The inlet port and the outlet port are in fluid communication with the flowcell via the fluidic channel. The fluidic channel can comprise another fluidic channel sidewall. This other fluidic channel sidewall forms an edge with the ceiling and another edge with the bottom.

Flowcells

The microwell array substrate can be packaged within a flowcell that provides for convenient interfacing with the rest of the fluid handling system and facilitates the exchange of fluids, e.g. cell and solid support suspensions, lysis buffers, rinse buffers, etc., that are delivered to the microwell array and/or emulsion droplet. Design features can include: (i) one or more inlet ports for introducing cell samples, solid support suspensions, or other assay reagents, (ii) one or more microwell array chambers designed to provide for efficient (e.g., uniform) filling and fluid-exchange while minimizing back eddies or dead zones, and (iii) one or more outlet ports for delivery of fluids to a sample collection point or a waste reservoir.

The design of the flowcell can include a plurality of microarray chambers that interface with a plurality of microwell arrays such that one or more different cell samples can be processed in parallel. The design of the flowcell can further include features for creating consistent (e.g., uniform) flow velocity profiles, i.e. "plug flow", across the width of the array chamber to provide for more efficient (e.g., uniform) delivery of cells and beads to the microwells, for example, by using a porous barrier located near the chamber inlet and upstream of the microwell array as a "flow diffuser", or by dividing each array chamber into several subsections that collectively cover the same total array area, but through which the divided inlet fluid stream flows in parallel. In some embodiments, the flowcell can enclose or incorporate more than one microwell array substrate. In some embodiments, the integrated microwell array/flowcell assembly can constitute a fixed component of the system. In some embodiments, the microwell array/flowcell assembly can be removable from the instrument.

In general, the dimensions of fluidic channel(s) and the array chamber(s) in flowcell designs will be optimized to (i) provide efficient (e.g., uniform) delivery of cells and beads to the microwell array, and (ii) to minimize sample and reagent consumption. The width of a fluidic channel can be different in different implementations, for example, ranging from 0.1 mm to 100 mm. In some embodiments, the width can be, or be about, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100 mm, or a number or a range between any two of these values. In some embodiments, the width can be at least, or at most, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or 100 mm.

The height of a fluidic channel can be different in different implementations, for example, ranging from 0.1 mm to 100 mm. In some embodiments, the height can be, or be about, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10 mm, or a number or a range between any two of these values. In some embodiments, the height can be at least, or at most, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, or 10 mm.

Flowcells can be fabricated using a variety of techniques and materials known to those of skill in the art. In general, a flowcell can be fabricated as a separate part and subsequently either mechanically clamped or permanently bonded to the microwell array substrate. Examples of suitable fabrication techniques include conventional machining, CNC machining, injection molding, 3D printing, alignment and lamination of one or more layers of laser or die-cut polymer films, or any of a number of microfabrication techniques such as photolithography and wet chemical etching, dry etching, deep reactive ion etching, or laser micromachining.

Once the flowcell part has been fabricated it can be attached to the microwell array substrate mechanically, e.g. by clamping it against the microwell array substrate (with or without the use of a gasket), or it can be bonded directly to the microwell array substrate using any of a variety of techniques (depending on the choice of materials used) known to those of skill in the art, for example, through the use of anodic bonding, thermal bonding, or any of a variety of adhesives or adhesive films, including epoxy-based, acrylic-based, silicone-based, UV curable, polyurethane-based, or cyanoacrylate-based adhesives. In some embodiments, the substrate can form the fluidic channel bottom of the fluidic channel, or the substrate can be on the fluidic channel bottom of the fluidic channel. In some embodiments, the substrate comprises silicon, fused-silica, glass, a polymer, a metal, an elastomer, polydimethylsiloxane, agarose, a hydrogel, or a combination thereof.

Flowcells can be fabricated using a variety of materials known to those of skill in the art, hi general, the choice of material used will depend on the choice of fabrication technique used, and vice versa. Examples of suitable materials include, but are not limited to, silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, metals (e.g. aluminum, stainless steel, copper, nickel, chromium, and titanium), a non-stick material such as teflon (PTFE), or a combination of these materials. The cyclic olefin polymers (COP) can comprise Zeonor® 1020R or Zeonor® 1060R.

Plug Flow

In some embodiments, the design of the flow cell may further include features for creating consistent (e.g., uniform) flow velocity profiles, i.e. "plug flow", across the width of the microwell chamber to provide for more efficient (e.g. uniform) delivery of cells and beads to the microwells, for example, by using a porous barrier located near the chamber inlet and upstream of the microwells as a "flow diffuser", or by dividing each microwell chamber into several subsections that collectively cover the same total array area, but through which the divided inlet fluid stream flows in parallel. Plug flow can be used (1) to provide efficient (e.g. uniform) cell and bead loading in the flowcell; (2) to eliminate flow-through of beads and cell buffers that are loaded to the flowcell, which increases the cell and bead capture efficiency of the flowcell; and/or (3) to enable agitation of small particles at the micro-well surface, which may eliminate bead doublets.

Figure 4B:
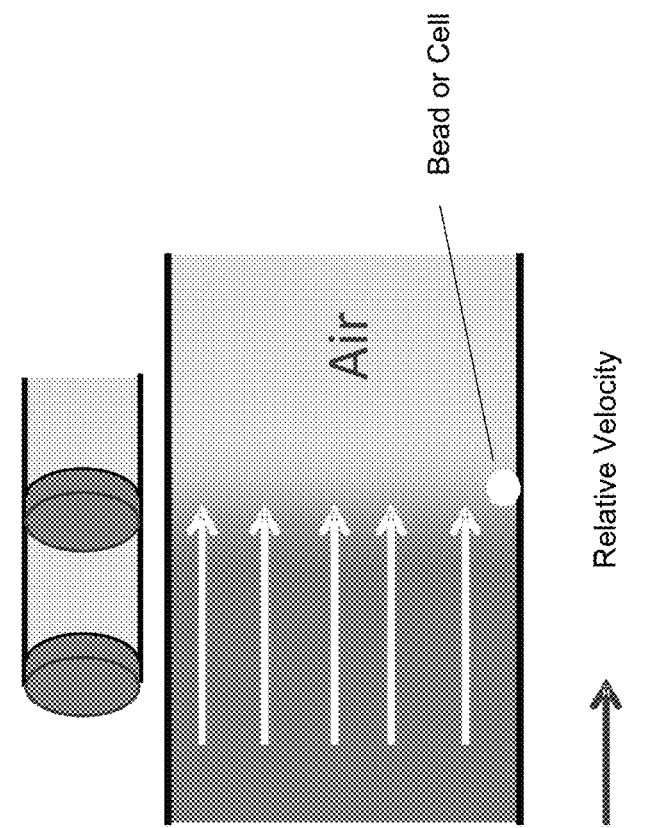
FIGS. 4A-4B are schematic illustrations showing relative velocity profiles of laminar flow and plug flow along the direction of the flow.
Figure 4A:
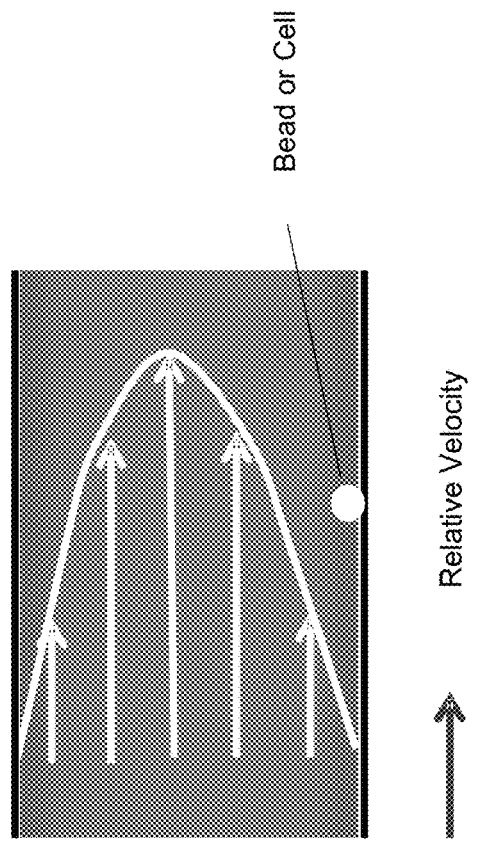

FIG. 4A is a schematic illustration showing the relative velocity profile of laminar flow along the direction of the flow. For laminar flow, the relative velocity profile can be parabolic. The maximum flow velocity occurs at, or close to, the center of the fluidic channel. The flow velocity can be low or approach zero at the fluidic channel boundaries (also referred to as the flowcell boundaries), the boundaries between the flow and surfaces of the fluidic channel such as the fluidic channel bottom and sidewalls. The low flow velocity at the fluidic channel boundaries may result in low or minimal agitation of beads or cells at the surface of the microwell array or the substrate comprising the microwells.

FIG. 4B is a schematic illustration showing the relative velocity profile of non-laminar flow, such as plug flow, along the direction of the flow. In some embodiments, with plug flow, the relative flow velocity can be constant across the cross-section of the fluidic channel. Plug flow can enable agitation of beads or cells at the surface of the microwell array or the substrate comprising the microwells. With such agitation of beads or cells, each microwell can include one bead and/or one cell. However, non-uniform displacement of a gas such as air, $CO_2$, or $N_2$ at the fluidic channel boundaries can result in non-uniform plug flow, with relative flow velocity approaching zero at the fluidic channel boundaries.

Figure 5A:
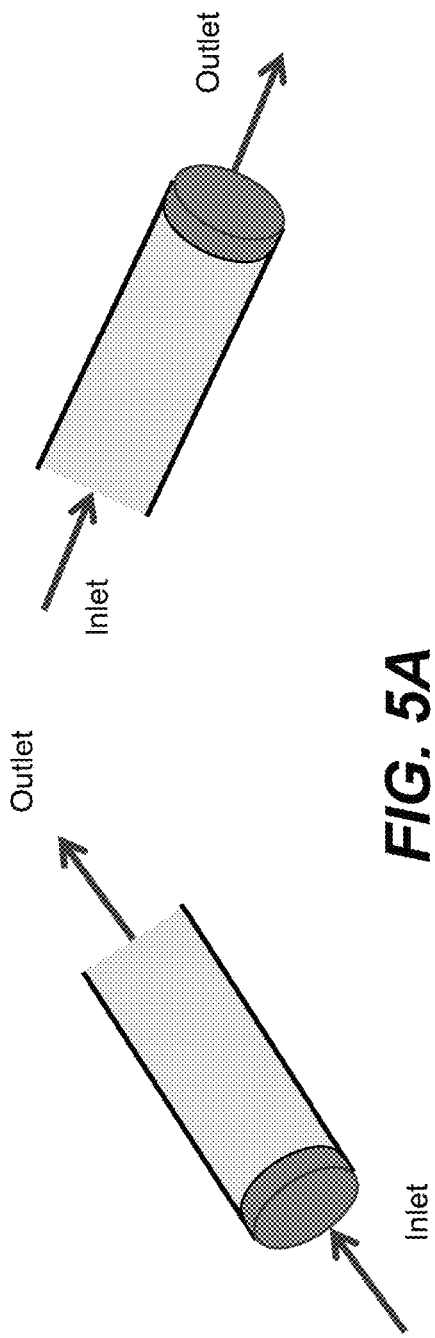
FIGS. 5A-5B show schematic illustrations of using buoyancy for gas-buffer plug flow and using capillary aided flow for horizontal plug flow.

A hydrophilic coating or superhydrophilic coating or treatment of the top wall (also referred to as ceiling, fluidic channel ceiling, or fluidic channel ceiling) within the fluidic channel of a flowcell can be used to introduce gas plugs and buffer plugs to a flowcell with horizontal non-tilting workflow (i.e., without tilting the flowcell). The superhydrophilic coating provides capillary aided flow for a uniform fluid front of the gas and buffer plug without the use of buoyancy to achieve gas displacement by buffer or to achieve buffer displacement by the gas. FIG. 5A shows a schematic illustration of using buoyancy for gas-buffer plug flow. Buoyancy can be used to achieve gas-buffer plug flow and other forms of plug flow, such as oil-water plug flow, in which the plug mass density is different from the bulk solution. Displacement of the gas with buffer requires upward tilt of the flowcell. Displacement of buffer with the gas requires downward tilt of the flowcell. Thus, a horizontal workflow may not be possible when buoyancy is used for gas-buffer plug flow. One requirement for achieving plug flow is that the liquid or gas does not mix with the buffer that is being displaced from the flowcell.

Figure 5B:

FIG. 5B shows a schematic illustration of using capillary aided flow for horizontal plug flow. A hydrophilic or superhydrophilic surface can facilitate a uniform meniscus and movement of the fluid front at the buffer-gas interface, thus avoiding breakdown of the plug within the flowcell without the use of buoyancy. The use of hydrophilic or superhydrophilic coatings can enable plug flow within a flowcell with a horizontal workflow. With hydrophilic or superhydrophilic coatings, the speed of the flow at the boundaries between the flow and the fluidic channel bottom can be non-zero. The relative flow velocity across the cross section of the fluidic channel can be constant or approximately constant. In some embodiments, the plug flow can be approximately horizontal plug flow. The horizontal plug flow can be capillary aided horizontal plug flow. In some embodiments, the plug flow may not depend on buoyancy of the gas. The plug flow may not depend on tilting of the device. The plug flow can be at a buffer-gas interface or other forms of plug flow, such as oil-water plug flow.

Coating Offset

Figure 6A:
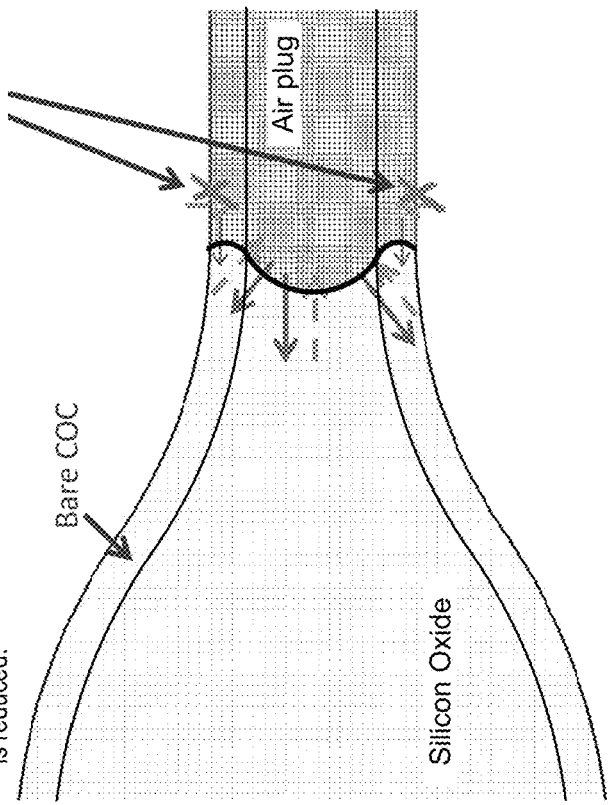
FIGS. 6A-6B are schematic illustrations showing directions of capillary flow and pressure-driven flow when the entire fluidic channel ceiling is coated with a hydrophilic coating or when the fluidic channel ceiling, except the edge of the fluidic channel ceiling, is coated with a hydrophilic coating.

FIG. 6A is a schematic illustration showing directions of capillary flow and pressure-driven flow when the entire fluidic channel ceiling is coated with a hydrophilic coating.

The entire ceiling of a flowcell is functionalized or coated with a hydrophilic coating. A gas plug, such as an air plug, can be injected into a flowcell filled with aqueous buffer. The profile of the gas-buffer fluid front is driven by capillary flow and pressure driven flow, where the capillary flow is opposite in direction to the pressure driven flow of the gas plug. The profile of the gas-buffer interface can be circular, and the expansion of the gas plug near the fluidic channel boundaries may be orthogonal to the fluidic channel boundaries.

Figure 6B:
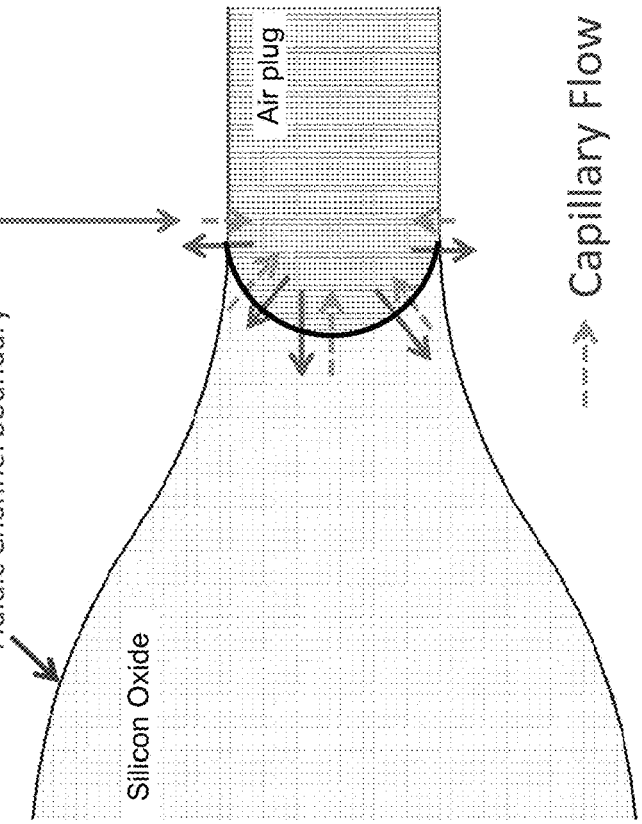

In some embodiments, hydrophilic and hydrophobic coatings can be used on a fluidic channel ceiling or a fluidic channel ceiling to tailor the profile of a gas-buffer fluid front in a flowcell. The selective coating (also referred to herein as functionalization) of the fluidic channel boundaries (also referred to herein as the flowcell boundaries) influences the direction of capillary flow within specific portions of the flowcell to control the profile of the gas-buffer fluid front profile. FIG. 6B is a schematic illustration showing directions of capillary flow and pressure-driven flow when the fluidic channel ceiling, except the edge of the fluidic channel ceiling, is coated with a hydrophilic coating. In some embodiments, the hydrophilic coating is offset from the fluidic channel boundaries (one or more edges formed by the fluidic channel ceiling and the sidewalls). The offset results in the fluidic channel ceiling at the fluidic channel boundaries not coated with a hydrophilic coating (also referred to as functionalized with a hydrophobic material). The remainder of the fluidic channel ceiling can be functionalized with a hydrophilic or a superhydrophilic material. As a result of the hydrophobic property of the fluidic channel ceiling at the edge of the fluidic channel ceiling, the capillary flow may be reduced or reversed in this region. As a result, the profile of the gas-buffer interface is modified, and the expansion of the gas plug near the fluidic channel boundaries may be no longer orthogonal to the edge.

The buffers used can be different in different implementations. In some embodiments, the buffer can be hydrophilic. For buffer-gas plug flow, the edge of the ceiling can be functionalized with a hydrophobic coating and the remainder can be functionalized with a hydrophilic coating. In some embodiments, the buffer can be hydrophobic rather than hydrophilic. For buffer-gas plug flow, the edge of the ceiling can be functionalized with a hydrophilic coating and the remainder can be functionalized with a hydrophobic coating. Other flowcell boundaries, for example the sidewalls or the bottom, can be similarly functionalized.

Particle Loading in Microwells

In some embodiments, a fluidic channel comprises a substrate on its bottom. The substrate can comprise a microwell array with a plurality of microwells. In some embodiments, a microwell can contain one particle (e.g., a cell or a bead). The percentage of microwells of a microwell array with one single particle can vary, for example, ranging from 25% to 90%. In some embodiments, the percentage of the microwells of the microwell array with a single particle (e.g., a single cell or a single bead) can be, or be about, 25%, 30%, 35%, 40%, 45%, 50%, 55%, 60%, 65%, 70%, 75%, 80%, 85%, 90%, 99%, or more of the microwells of the microwell array can comprise a single cell and a synthetic particle. In some embodiments, the percentage of the microwells of the microwell array with a single particle (e.g., a single cell or a single bead) can be at least, or at most, 25%, 30%, 35%, 40%, 45%, 50%, 55%, 60%, 65%, 70%, 75%, 80%, 85%, 90%, or 99%.

A microwell can contain two different types of particles (e.g., a cell and a bead). The percentage of microwells of a microwell array with one particle of each of two different types of particles can vary, for example, ranging from 25% to 90%. In some embodiments, the percentage of the microwells of the microwell array with one particle of each of two different types of particles (e.g., a single cell and a single bead) can be, or be about, 25%, 30%, 35%, 40%, 45%, 50%, 55%, 60%, 65%, 70%, 75%, 80%, 85%, 90%, 99%, or more of the microwells of the microwell array can comprise a single cell and a synthetic particle. In some embodiments, the percentage of the microwells of the microwell array with one particle of each of two different types of particles (e.g., a single cell or a single bead) can be at least, or at most, 25%, 30%, 35%, 40%, 45%, 50%, 55%, 60%, 65%, 70%, 75%, 80%, 85%, 90%, or 99%.

In some embodiments, a microwell of the plurality of microwells comprises a coating. The coating can comprise, or be, polyethylene glycol (PEG), poly-Hema, pluronic acid F68, pluronic acid F108, pluronic acid F127, polysorbate 20, silicon dioxide ($SiO_2$), silicon nitride, or a combination thereof. In some embodiments, a microwell of the plurality of microwells can comprise a plasma-treated surface.

Cartridges

In some embodiments, the microwell array and the flowcell, can be packaged within a consumable cartridge that provides for convenient interfacing with the rest of the fluid handling system. The flowcell can facilitate the exchange of fluids, e.g. cell and bead suspensions, lysis buffers, rinse buffers, etc., that are delivered to the microwells. In some embodiments, the flow cell may be designed to facilitate efficient (e.g., uniform) distribution of cells and beads across the plurality of microwells. Design features may include: (i) one or more inlet ports for introducing cell samples, bead suspensions, or other assay reagents, (ii) one or more microwell chambers designed to provide for efficient (e.g., uniform) filling and efficient fluid-exchange while minimizing back eddies or dead zones, and (iii) one or more outlet ports for delivery of fluids to a sample collection point or a waste reservoir. In some embodiments, the design of the flow cell may include a plurality of microwell chambers that interface with a plurality of microwell arrays on a single substrate, or with a plurality of microwell array substrates, such that one or more different cell samples may be processed in parallel. In some embodiments, the design of the flow cell, e.g. the layout of the fluid channels and chambers, may be adjusted so that different patterns of microwells (i.e. configurable microarray patterns) are accessed by fluids in a given design.

Figure 7A:
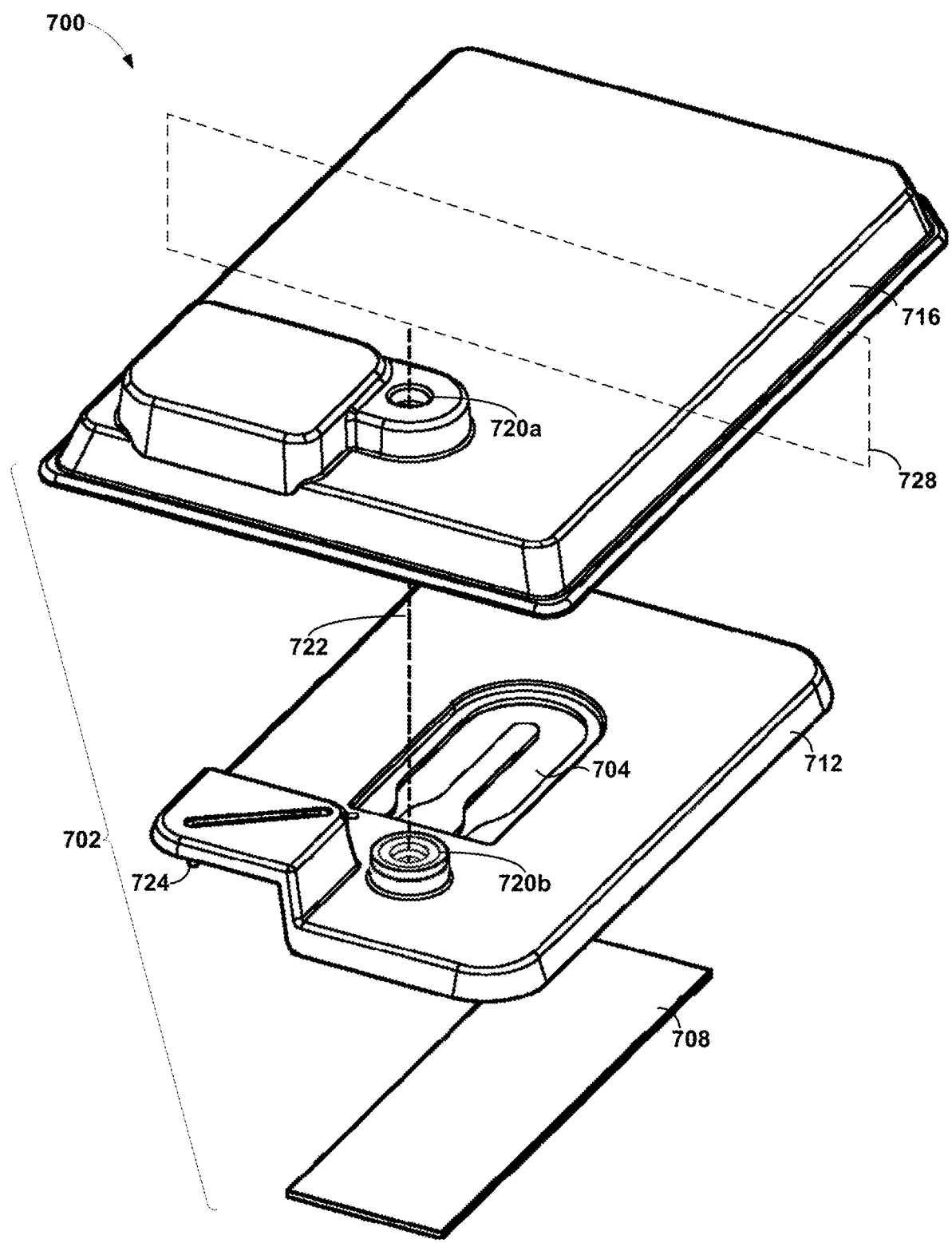
FIG. 7A shows an exploded view of an exemplary cartridge for barcoding.

In some embodiments, the flowcell can be part of the cartridge. FIG. 7A shows an exploded view of an exemplary cartridge 700 for stochastic barcoding. The cartridge 700 can include a flowcell 702 with a fluidic channel 704 formed by a microwell array substrate 708, a fluid channel layer 712, and a cover plate 716. The number of layers forming the flowcell 700 can be different in different implementations, ranging from 1 to 20. In some embodiments, the number of layers forming the flowcell 700 can be, or be about, 1, 2, 3, 4, 5, 6, 7, 8, 9, 10, 11, 12, 13, 14, 15, 16, 17, 18, 19, 20, or a number or a range between any two of these values. In some embodiments, the number of layers forming the flowcell 700 can be at least, or at most, 1, 2, 3, 4, 5, 6, 7, 8, 9, 10, 11, 12, 13, 14, 15, 16, 17, 18, 19, 20. FIG. 7A shows that the cartridge 700 includes one inlet port, formed by inlet port components 720a and 720b on the cover plate 716 and the fluidic channel layer 712 respectively. The inlet port components 720a and 720b can be coaxial along the axis 722. The cartridge 700 includes one outlet port 724 on the fluidic channel layer 712. The locations of the outlet port can be different in different implementations. In some embodiments, the outlet port can be on the cover plate 716. In some embodiments the outlet port can be formed by outlet port components on the cover plate 716 and the fluidic channel layer 712.

The cartridge 700 or the flowcell 702 can include (i) one or more inlet ports for creating fluid connections with the instrument or manually introducing cell samples, bead suspensions, or other assay reagents into the cartridge. The flowcell can include one or more of (ii) one or more bypass channels, i.e. for self-metering of cell samples and bead suspensions, to avoid overfilling or back flow, (iii) one or more integrated microwell array/flowcell assemblies, or one or more chambers within which the microarray substrate(s) are positioned, (iv) integrated miniature pumps or other fluid actuation mechanisms for controlling fluid flow through the device, (v) integrated miniature valves (or other containment mechanisms) for compartmentalizing pre-loaded reagents (for example, bead suspensions) or controlling fluid flow through the device, (vi) one or more vents for providing an escape path for trapped gas, (vii) one or more sample and reagent waste reservoirs, (viii) one or more outlet ports for creating fluid connections with the instrument or providing a processed sample collection point. (ix) mechanical interface features for reproducibly positioning the removable, consumable cartridge with respect to the instrument system, and for providing access so that external magnets can be brought into close proximity with the microwell array, (x) integrated temperature control components or a thermal interface for providing good thermal contact with the instrument system, (xi) optical interface features, e.g. a transparent window, for use in optical interrogation of the microwell array, or any combination thereof.

Figure 7B:
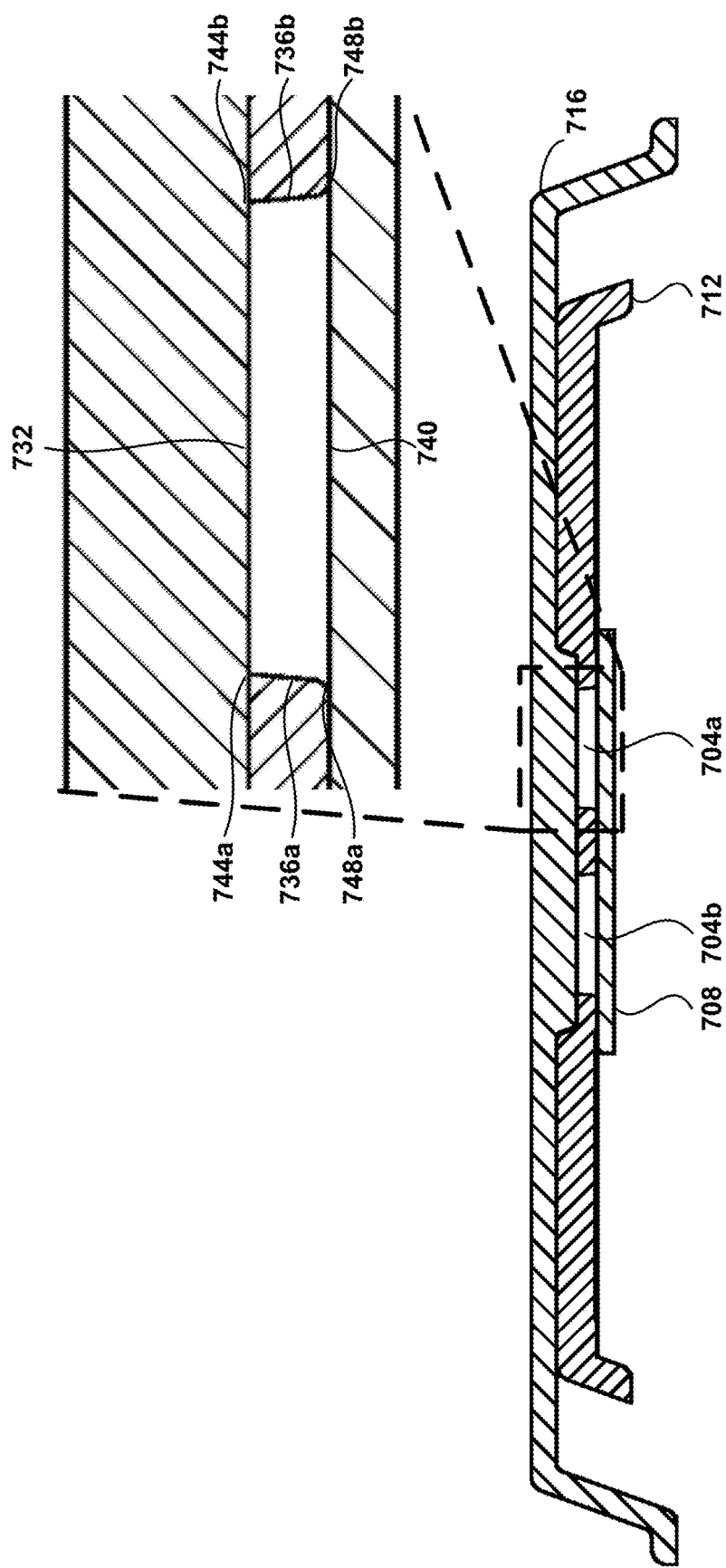
FIG. 7B shows a cross-sectional view of the exemplary cartridge shown in FIG. 7A.

FIG. 7B shows a cross-sectional view of the exemplary cartridge 700 taken along the plane 728 in FIG. 7A. FIG. 7B shows two fluidic channel sections 704a and 704b of the fluidic channel 704. The fluidic channel section 704a comprises a fluidic channel ceiling 732, two fluidic channel sidewalls 736a and 736b (also referred to as a first sidewall 736a and a second sidewall 736b), and a fluidic channel bottom 740. The fluidic channel ceiling 732 and the fluidic channel sidewall 736a form an edge 744a (also referred to as a ceiling-first sidewall edge). The fluidic channel ceiling 732 and the fluidic channel sidewall 736b form another edge 744b (also referred to as a ceiling-second sidewall edge). The fluidic channel sidewalls 736a and 736b can have positive draft angles with respect to the fluidic channel ceiling 732, for example, ranging from 1-15 degrees. In some embodiments, the draft angle of the fluidic channel sidewall 736a or 736b with respect to the fluidic channel ceiling 732 can be, or be about, 1, 2, 3, 4, 5, 6, 7, 8, 9, 10, 11, 12, 13, 14, 15 degrees, or a number or a range between any two of these values. In some embodiments, the draft angle of the fluidic channel sidewall 736a or 736b with respect to the fluidic channel ceiling 732 can be at least, or at most, 1, 2, 3, 4, 5, 6, 7, 8, 9, 10, 11, 12, 13, 14, or 15 degrees.

The fluidic channel bottom 740 and the fluidic channel sidewall 736a form an edge 748a (also referred to as a bottom-first sidewall edge). The fluidic channel bottom 740 and the fluidic channel sidewall 736b form another edge 748b (also referred to as a bottom-second sidewall edge). The fluidic channel sidewalls 736a and 736b can have negative draft angles with respect to the fluidic channel bottom 740, for example, ranging from −1 to −15 degrees. In some embodiments, the draft angle of the fluidic channel sidewall 736a or 736b with respect to the fluidic channel bottom 740 can be, or be about, −1, −2, −3, −4, −5, −6, −7, −8, −9, −10, −11, −12, −13, −14, −15 degrees, or a number or a range between any two of these values. In some embodiments, the draft angle of the fluidic channel sidewall 736a or 736b with respect to the fluidic channel bottom 740 can be at least, or at most, −1, −2, −3, −4, −5, −6, −7, −8, −9, −10, −11, −12, −13, −14, or −15 degrees.

The cartridge can be designed to process more than one sample in parallel. The cartridge can further comprise one or more removable sample collection chamber(s) that are suitable for interfacing with stand-alone PCR thermal cyclers or sequencing instruments. The cartridge itself can be suitable for interfacing with stand-alone PCR thermal cyclers or sequencing instruments. The term "cartridge" as used in this disclosure can be meant to include any assembly of parts which contains the sample and beads during performance of the assay.

The cartridge can further comprise components that are designed to create physical or chemical barriers that prevent diffusion of (or increase path lengths and diffusion times for) large molecules in order to minimize cross-contamination between microwells. Examples of such barriers can include, but are not limited to, a pattern of serpentine channels used for delivery of cells and solid supports (e.g., beads) to the microwell array, a retractable platen or deformable membrane that is pressed into contact with the surface of the microwell array substrate during lysis or incubation steps, the use of larger beads, e.g. Sephadex beads as described previously, to block the openings of the microwells, or the release of an immiscible, hydrophobic fluid from a reservoir within the cartridge during lysis or incubation steps, to effectively separate and compartmentalize each microwell in the array.

Cartridges can be fabricated using a variety of techniques and materials known to those of skill in the art. In general, the cartridges will be fabricated as a series of separate component parts and subsequently assembled using any of a number of mechanical assemblies or bonding techniques. Examples of suitable fabrication techniques include, but are not limited to, conventional machining, CNC machining, injection molding, thermoforming, and 3D printing. Once the cartridge components have been fabricated they can be mechanically assembled using screws, clips, and the like, or permanently bonded using any of a variety of techniques (depending on the choice of materials used), for example, through the use of thermal bonding/welding or any of a variety of adhesives or adhesive films, including epoxy-based, acrylic-based, silicone-based, UV curable, polyurethane-based, or cyanoacrylate-based adhesives.

Cartridge components can be fabricated using any of a number of suitable materials, including but not limited to silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, non-stick materials such as teflon (PTFE), metals (e.g. aluminum, stainless steel, copper, nickel, chromium, and titanium), or any combination thereof.

The inlet and outlet features of the cartridge can be designed to provide convenient and leak-proof fluid connections with the instrument, or can serve as open reservoirs for manual pipetting of samples and reagents into or out of the cartridge. Examples of convenient mechanical designs for the inlet and outlet port connectors can include, but are not limited to, threaded connectors, Luer lock connectors, Luer slip or "slip tip" connectors, press fit connectors, and the like. The inlet and outlet ports of the cartridge can further comprise caps, spring-loaded covers or closures, or polymer membranes that can be opened or punctured when the cartridge is positioned in the instrument, and which serve to prevent contamination of internal cartridge surfaces during storage or which prevent fluids from spilling when the cartridge is removed from the instrument. The one or more outlet ports of the cartridge can further comprise a removable sample collection chamber that is suitable for interfacing with stand-alone PCR thermal cyclers or sequencing instruments.

In some embodiments, the inlet port and the outlet port can be capable of directing a flow of a fluid through the fluidic channel, thereby contacting the microwells with the fluid. In some embodiments, the device comprises a pipette tip interface for loading or removing a cell sample, an assay reagent, a bead suspension, waste from the device, or a combination thereof. The device can comprise the cell sample, the assay reagent, the bead suspension, or a combination thereof.

The cartridge can include integrated miniature pumps or other fluid actuation mechanisms for control of fluid flow through the device. Examples of suitable miniature pumps or fluid actuation mechanisms can include, but are not limited to, electromechanically- or pneumatically-actuated miniature syringe or plunger mechanisms, membrane diaphragm pumps actuated pneumatically or by an external piston, pneumatically-actuated reagent pouches or bladders, or electro-osmotic pumps.

The cartridge can include miniature valves for compartmentalizing pre-loaded reagents or controlling fluid flow through the device. Examples of suitable miniature valves can include, but are not limited to, one-shot "valves" fabricated using wax or polymer plugs that can be melted or dissolved, or polymer membranes that can be punctured; pinch valves constructed using a deformable membrane and pneumatic, magnetic, electromagnetic, or electromechanical (solenoid) actuation, one-way valves constructed using deformable membrane flaps, and miniature gate valves.

The cartridge can include vents for providing an escape path for trapped air or gas such as $CO_2$ or $N_2$. Vents can be constructed according to a variety of techniques, for example, using a porous plug of polydimethylsiloxane (PDMS) or other hydrophobic material that allows for capillary wicking of air or gas but blocks penetration by water.

The mechanical interface features of the cartridge can provide for easily removable but highly precise and repeatable positioning of the cartridge relative to the instrument system. Suitable mechanical interface features can include, but are not limited to, alignment pins, alignment guides, mechanical stops, and the like. The mechanical design features can include relief features for bringing external apparatus, e.g. magnets or optical components, into close proximity with the microwell array chamber.

The cartridge can include temperature control components or thermal interface features for mating to external temperature control modules. Examples of suitable temperature control elements can include, but are not limited to, resistive heating elements, miniature infrared-emitting light sources, Peltier heating or cooling devices, heat sinks, thermistors, thermocouples, and the like. Thermal interface features can be fabricated from materials that are good thermal conductors (e.g. copper, gold, silver, etc.) and can comprise one or more flat surfaces capable of making good thermal contact with external heating blocks or cooling blocks.

The cartridge can include optical interface features for use in optical imaging or spectroscopic interrogation of the microwell array. The cartridge can include an optically transparent window, e.g. the microwell substrate itself or the side of the flowcell or microarray chamber that is opposite the microwell array, fabricated from a material that meets the spectral requirements for the imaging or spectroscopic technique used to probe the microwell array. Examples of suitable optical window materials can include, but are not limited to, glass, fused-silica, polymethylmethacrylate (PMMA), polycarbonate (PC), cyclic olefin polymers (COP), or cyclic olefin copolymers (COC).

Fluidic Channel

Figure 8:
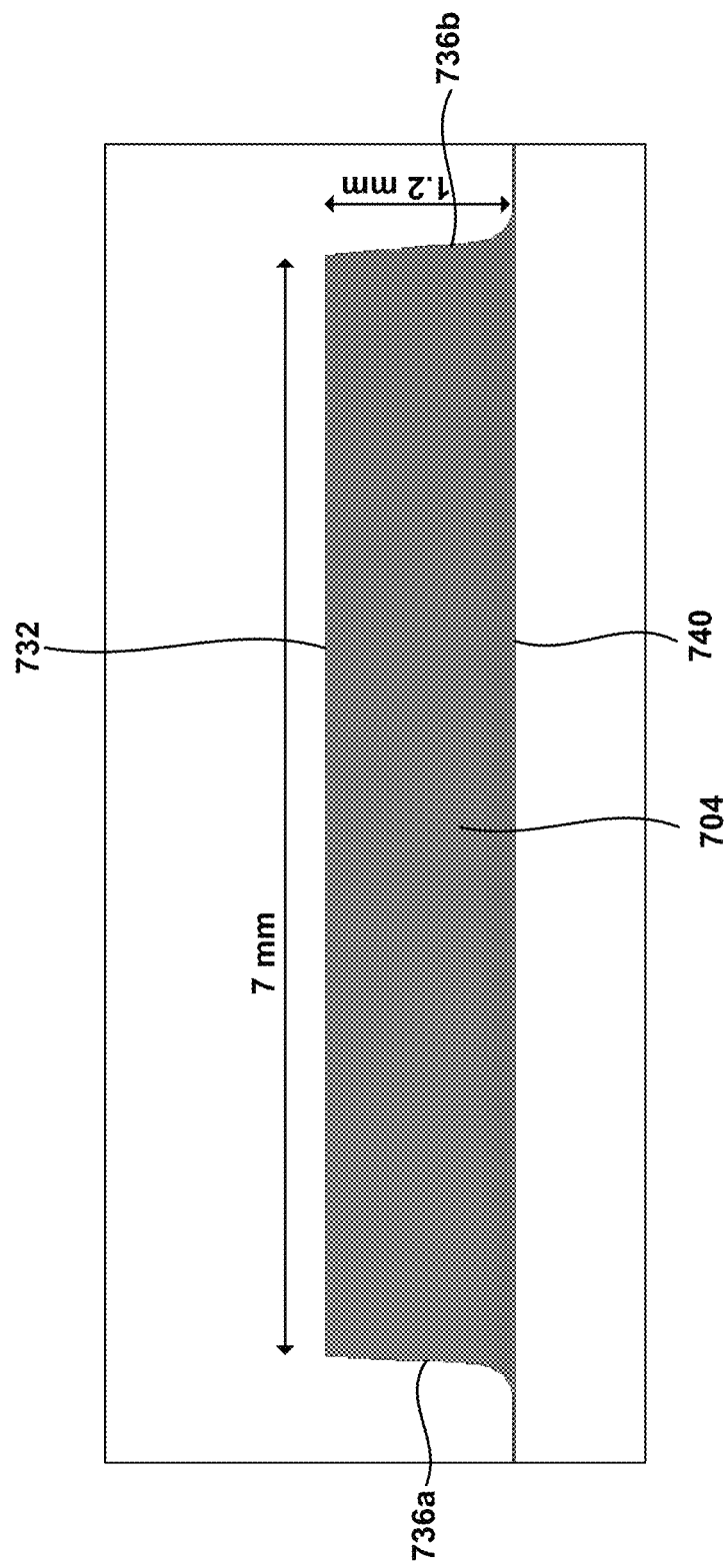
FIG. 8 shows a cross-sectional view of an exemplary channel of a cartridge for barcoding as shown in FIG. 7B.

FIG. 8 shows a cross-sectional view of an exemplary fluidic channel 704 of a cartridge 700 for stochastic barcoding. The fluidic channel 704 comprises a fluidic channel ceiling 732, two fluidic channel sidewalls 736a and 736b, and a fluidic channel bottom 740. The fluidic channel ceiling 732 and the fluidic channel sidewall 736a form an edge. The fluidic channel ceiling 732 and the fluidic channel sidewall 736b form another edge. The fluidic channel sidewalls 736a and 736b have positive draft angles, for example, ranging from 1-15 degrees. The width and the height of the fluidic channel 704 shown in FIG. 8 can be 7 mm and 1.2 mm respectively.

The width of the fluidic channel 704 can be different in different implementations, for example, ranging from 1 mm to 20 mm. In some embodiments, the width of the fluidic channel 704 can be, or be about, 1, 2, 3, 4, 5, 6, 7, 8, 9, 10, 11, 12, 13, 14, 15, 16, 17, 18, 19, 20 mm, or a number or a range between any two of these values. In some embodiments, the width of the fluidic channel 704 can be at least, or at most, 1, 2, 3, 4, 5, 6, 7, 8, 9, 10, 11, 12, 13, 14, 15, 16, 17, 18, 19, or 20 mm. A larger width, for example 7 mm, can increase the flowcell area of a given flowcell length.

The height of the fluidic channel 704 can be different in different implementations, for example, ranging from 0.1 mm to 2 mm. In some embodiments, the height of the fluidic channel 704 can be, or be about, 0.1, 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, 0.20 mm, or a number or a range between any two of these values. In some embodiments, the height of the fluidic channel 704 can be at least, or at most, 0.1, 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, or 0.20 mm.

Fluidic Channel Ceiling and Sidewall Properties

As described herein, in some embodiments, the contact angle of the fluidic channel ceiling can be smaller than the contact angle of a fluidic channel side wall by, for example, 10 degrees. In some embodiments, the fluidic channel ceiling is hydrophilic. The degree of hydrophilicity of the fluidic channel ceiling can be represented by the contact angle of the fluidic channel ceiling. In some embodiments, the contact angle of the fluidic channel ceiling corresponds to an average of contact angles of a plurality of locations on the fluidic channel ceiling. The contact angle of the fluidic channel ceiling can be different in different implementations, for example, ranging from 0 to 90 degrees. In some embodiments, the contact angle of the fluidic channel ceiling can be, or be about, 0, 1, 2, 3, 4, 5, 6, 7, 8, 9, 10, 20, 30, 40, 50, 60, 70, 80, 90 degrees, or a number or a range between any two of these values. In some embodiments, the contact angle of the fluidic channel ceiling can be at least, or at most, 0, 1, 2, 3, 4, 5, 6, 7, 8, 9, 10, 20, 30, 40, 50, 60, 70, 80, or 90 degrees.

The contact angle of the fluidic channel ceiling can be smaller than the contact angle of the fluidic channel sidewall. The difference between the contact angle of the fluidic channel ceiling and the contact angle of the fluidic channel sidewall can be different in different implementations. In some embodiments, the difference can be, or be about, 10, 20, 30, 40, 50, 60, 70, 80, 90 degrees, or a number or a range between any two of these values. In some embodiments, the difference can be at least, or at most, 10, 20, 30, 40, 50, 60, 70, 80, or 90 degrees.

The degree of hydrophilicity of the fluidic channel sidewall can be represented by the contact angle of the fluidic channel sidewall. In some embodiments, the contact angle of the fluidic channel sidewall corresponds to an average of contact angles of a plurality of locations on the fluidic channel sidewall. The contact angle of the fluidic channel sidewall can be different in different implementations. In some embodiments, the contact angle of the fluidic channel sidewall can be, or be about, 10, 20, 30, 40, 50, 60, 70, 80, 88, 90 degrees, or a number or a range between any two of these values. In some embodiments, the contact angle of the fluidic channel sidewall can be at least, or at most, 10, 20, 30, 40, 50, 60, 70, 80, 88, or 90 degrees. In some embodiments, the fluidic channel sidewall has a positive draft angle of 1-15 degrees.

In some embodiments, the contact angle of the fluidic channel ceiling is sufficiently smaller (e.g., 10, 20, 30, 40, 50, 60, 70, 80, or more degrees) than the contact angle of the fluidic channel sidewall to enable non-laminar flow within the fluidic channel. In some embodiments, the non-laminar flow within the fluidic channel enables agitation of a particle on the surface of the substrate by a flow within the fluidic channel. A speed of the flow at a boundary between the flow and the fluidic channel bottom can be non-zero. The relative flow velocity of a flow across a cross section of the fluidic channel can be constant or approximately constant. The non-laminar flow can be plug flow.

In some embodiments, the non-laminar flow can be approximately plug flow. The plug flow can be approximately horizontal plug flow. The horizontal plug flow can be capillary aided horizontal plug flow. In some embodiments, the plug flow may not depend on buoyancy of the gas. The plug flow may not depend on tilting of the device. The plug flow can be at a buffer-gas interface.

Each of FIGS. 9A-9H is a schematic illustration of a cross-sectional view of a non-limiting exemplary fluidic channel 704 with the fluidic channel ceiling 732, sidewalls 736a, 736b, and/or bottom 740 comprising a coating. The fluidic channel 704 comprises a fluidic channel ceiling 732, two fluidic channel sidewalls 736a and 736b, and a fluidic channel bottom 740. The fluidic channel ceiling 732 and the fluidic channel sidewall 736a form an edge 744a. The fluidic channel bottom 740 and the fluidic channel sidewall 736a form an edge 748a. The fluidic channel bottom 740 and the fluidic channel sidewall 736b form another edge 748b. The fluidic channel ceiling 732 and the fluidic channel sidewall 736b form another edge 744b. The fluidic channel sidewalls 736a and 736b may have zero or positive draft angles, for example, ranging from 1-15 degrees.

In some embodiments, the fluidic channel ceiling 732 comprises a hydrophilic coating 752. For example, the hydrophilic coating 752 can be a superhydrophilic coating. The hydrophilic coating 752 can comprise polyethylene glycol (PEG), poly-Hema, pluronic acid F68, pluronic acid F108, pluronic acid F127, polysorbate 20, silicon dioxide ($SiO_2$), silicon nitride, or any combination thereof. The contact angle of the hydrophilic coating 752 can be different in different implementations. In some embodiments, the contact angle of the hydrophilic coating 752 can be, or be about, 0, 1, 2, 3, 4, 5, 6, 7, 8, 9, 10, 20, 23, 30, 40, 50, 60, 70, 80, 90 degrees, or a number or a range between any two of these values. In some embodiments, the contact angle of the hydrophilic coating 752 can be at least, or at most, 0, 1, 2, 3, 4, 5, 6, 7, 8, 9, 10, 20, 23, 30, 40, 50, 60, 70, 80, or 90 degrees. The ceiling 732 can be coated with the hydrophilic coating by sputtering, thermal growth, adsorption, covalent binding (e.g., by incubating the fluidic channel ceiling 732 or the surface of the fluidic channel ceiling 732 in a liquid with the coating material dissolved therein), or any combination thereof.

In some embodiments, the hydrophilic coating 752 can have an offset 754a, 754b from the edge 744a, 744b formed by the fluidic channel ceiling 732 and fluidic channel sidewall 744a, 744b. For example, the hydrophilic coating 753 can be offset from one of the edges 744a, 744b such that the central portion of the fluidic channel ceiling 732 comprises the hydrophilic coating 753 while the non-central portions of the fluidic channel ceiling 732 does not comprise the hydrophilic coating. As another example, the hydrophilic coating 753 can be offset from both edges 744a, 744b. The offset 754a, 754b can be different in different implementations, for example, ranging from 1 micrometer to 4000 micrometers. In some embodiments, the offset 744a, 744b can be, or be about, 1, 2, 3, 4, 5, 6 7, 8, 9, 10, 20, 30, 40, 50, 60, 70, 80, 90, 100, 200, 300, 400, 500, 600, 700, 800, 900, 1000, 2000, 3000, 4000 micrometers, or a number or a range between any two of these values. In some embodiments, the offset 744a, 744b can be at least, or at most, 1, 2, 3, 4, 5, 6 7, 8, 9, 10, 20, 30, 40, 50, 60, 70, 80, 90, 100, 200, 300, 400, 500, 600, 700, 800, 900, 1000, 2000, 3000, or 4000 micrometers. The offset 744a, 744b can be different in different implementations, for example, ranging from 1% to 25% of the width of the fluidic channel ceiling 732. In some embodiments, the offset 744a, 744b can be, or be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or a number or a range between any two of these values, of the width of the fluidic channel ceiling 732. In some embodiments, the offset 744a, 744b can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% of the fluidic channel ceiling 732.

Figure 9A:
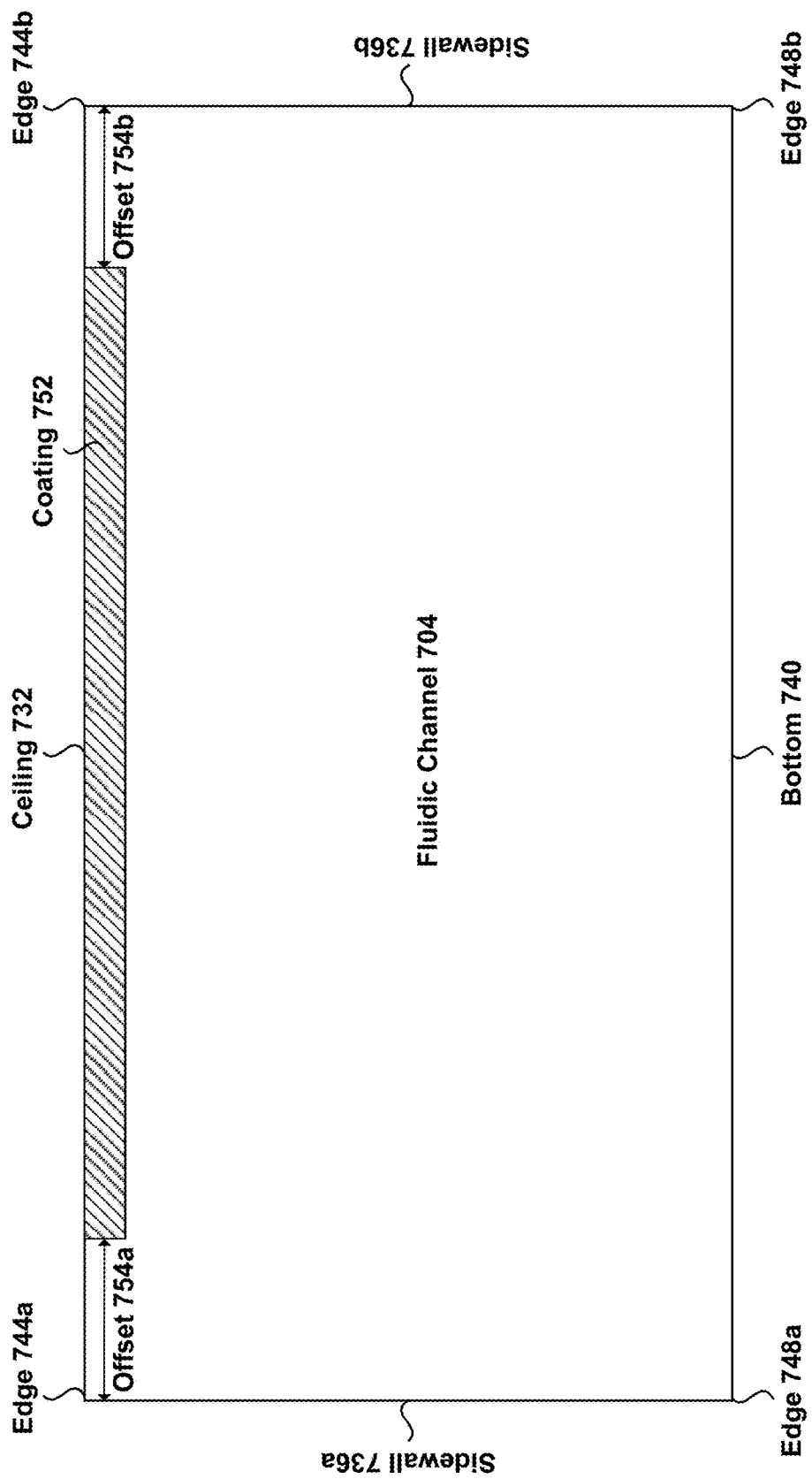
Figure 9F:
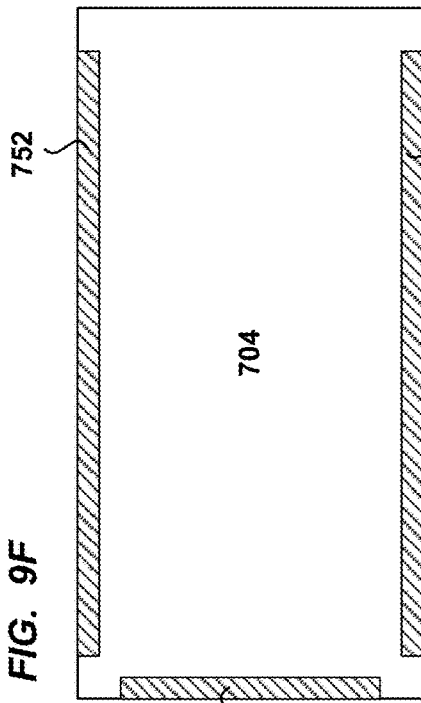
Figure 9H:
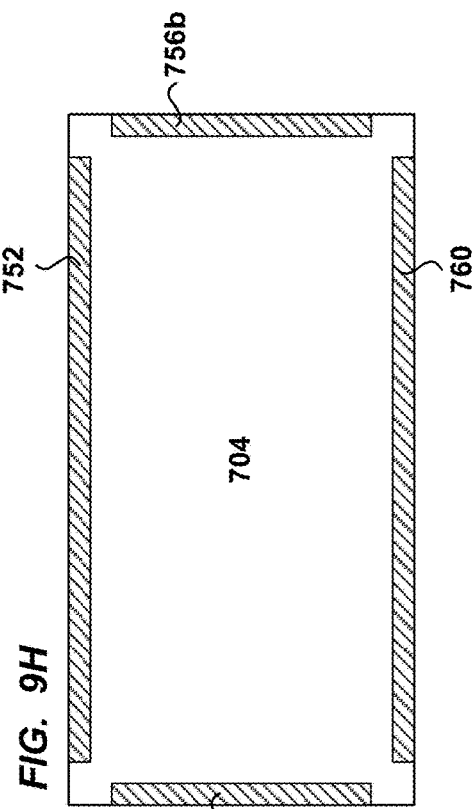
Figure 9E:
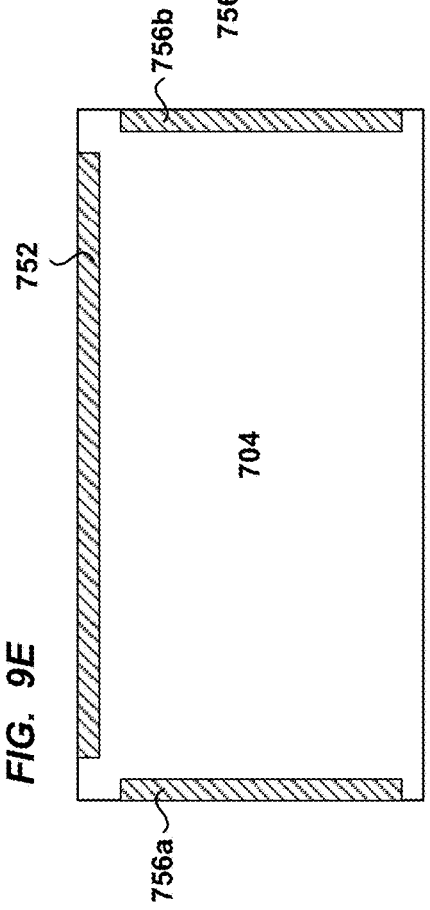
Figure 9G:
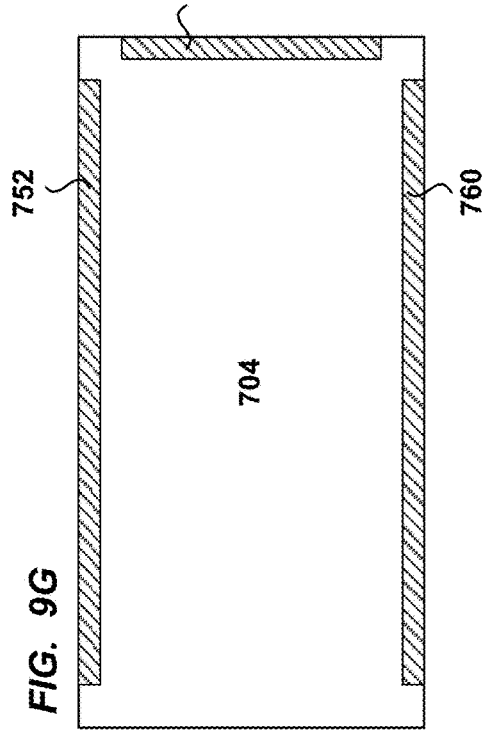

In some embodiments, the fluidic channel ceiling 732 and one more surface of the fluidic channel 704 comprises a coating, such as a hydrophilic coating. FIGS. 9B-9D illustrate that the sidewall 756a (FIG. 9 B), 756b (FIG. 9C), or the bottom 760 (FIG. 9D) comprising a coating 756a, 756b, 760. In some embodiments, the fluidic channel ceiling 732 and two more surfaces of the fluidic channel 704 comprises a coating, such as a hydrophilic coating (FIGS. 9E-9G). In some embodiments, the fluidic channel ceiling 732 and three more surfaces of the fluidic channel comprising a coating, such as a hydrophilic coating (FIG. 9H). The coatings 752, 756a, 756b, 760 can be the same or different. For example, the coatings 752, 756a, 756b, 760 can be different hydrophilic coatings. As another example, the coating 752 on the fluidic channel ceiling 732 can be a hydrophilic coating, and the coatings 756a, 756b, 760 on the fluidic channel sidewalls 736a, 736b and the bottom 740 can be a hydrophilic coating or a hydrophobic coating. Although FIGS. 9A-9H show that all the coatings 752, 756a, 756b, 760 are offset from the edges 744a, 744b, 748a, 748b, such offsets are for illustration only and are not intended to be limiting. The number of the coatings 752, 756a, 756b, 760 that are offset from the edges 744a, 744b, 748a, 748b can be different in different implementations, such as 0, 1, 2, 3, or 4. Each coating 752, 756a, 756b, 760 can be offset from one or more edges 744a, 744b, 748a, 748b.

EXAMPLES

Some aspects of the embodiments discussed above are disclosed in further detail in the following examples, which are not in any way intended to limit the scope of the present disclosure.

Example 1

Bead Aggregations at the Fluidic Channel Boundaries when the Ceiling and Sidewalls of the Fluidic Channel had No Hydrophilic Coating This example demonstrates that having a small difference in the contact angles between the ceiling and sidewalls of a fluidic channel can result in bead aggregations at the fluidic channel boundaries.

Figure 10A:
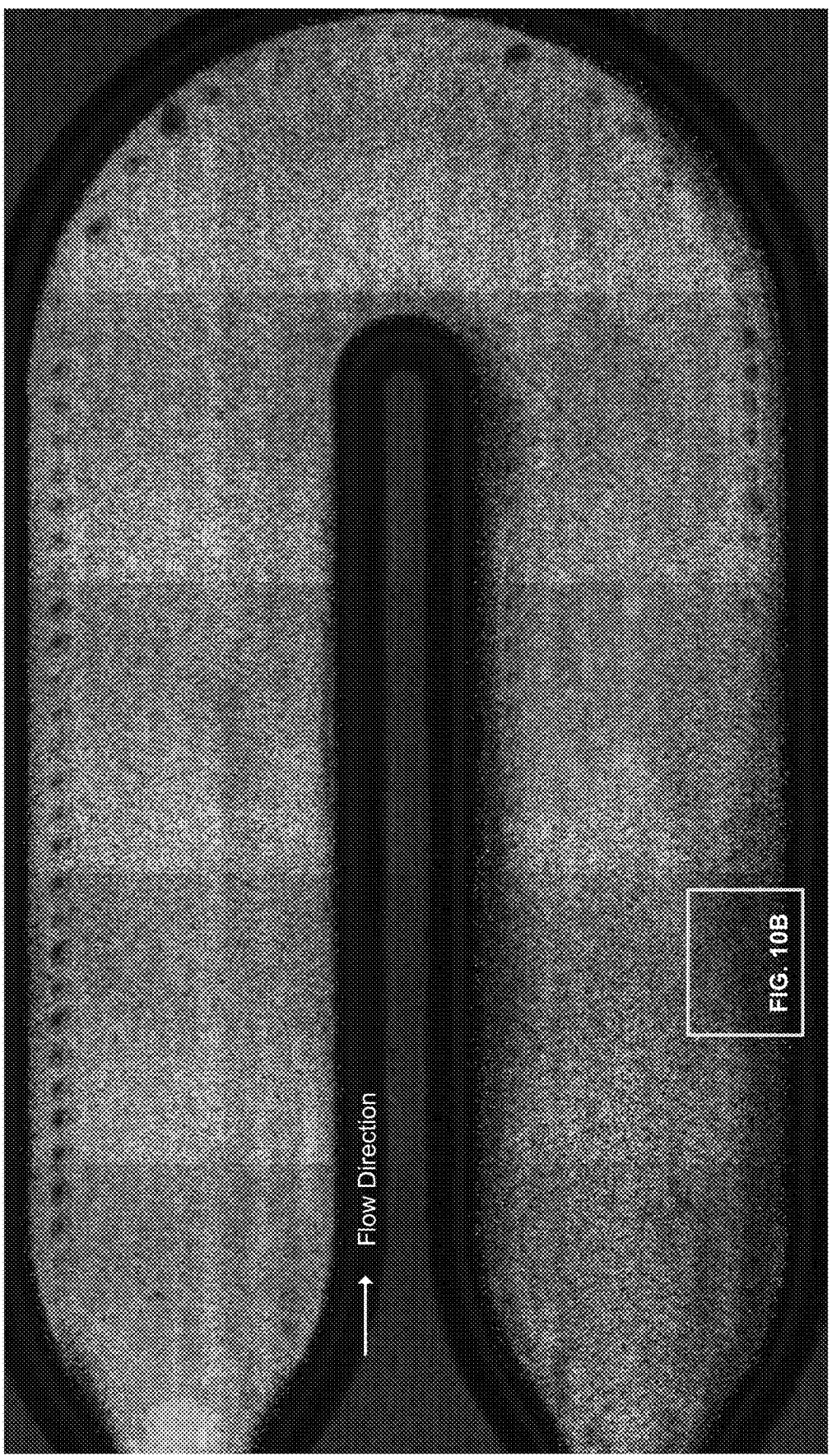
FIGS. 10A-10B are images of a microwell array showing substantial bead aggregations at the fluidic channel boundaries. The microwell array was at the bottom of a fluidic channel in a flowcell. The bottom of the fluidic channel of the flowcell had a hydrophilic coating of silicon dioxide, but neither of the ceiling and sidewalls of the fluidic channel of the flowcell had hydrophilic coating of silicon dioxide. Bead aggregations were substantial at the fluidic channel boundaries.
Figure 10B:
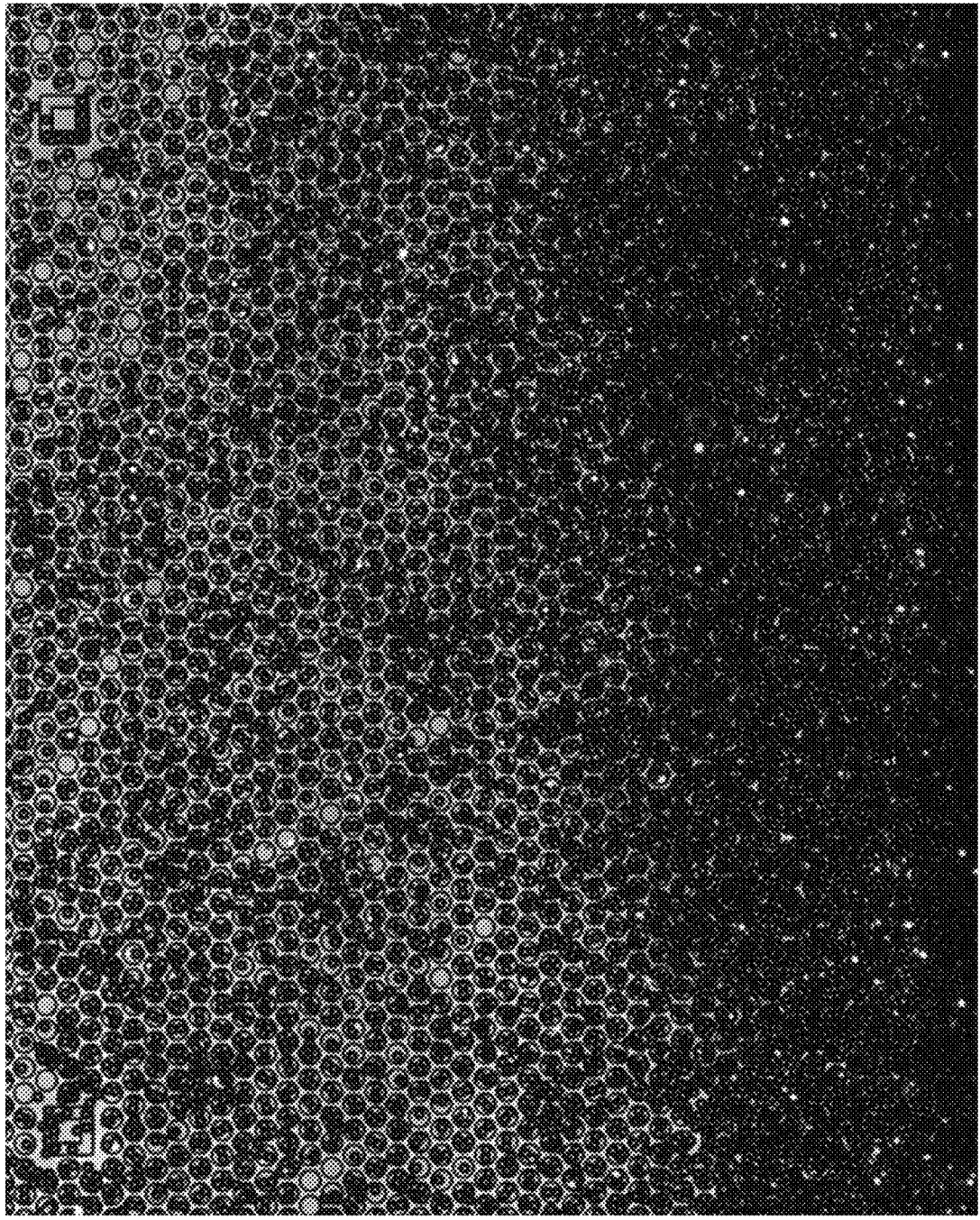

FIGS. 10A-10B are images of a microwell array showing substantial bead aggregations at the fluidic channel boundaries. The microwell array was at the bottom of a flowcell. The fluidic channel of the flowcell was 7 mm in width. The ceiling and sidewalls of the fluidic channel of the flowcell had no hydrophilic coating of silicon dioxide. Bead aggregations were substantial at the fluidic channel boundaries because of incomplete gas displacement. The non-uniform fluid front also resulted in high bead losses at the flowcell center, and resulted in patchy coverage of beads throughout the microwell array.

Altogether, these data demonstrate that having a small difference in the contact angles between the ceiling and sidewalls of a fluidic channel can result in incomplete gas displacement, which can in turn result in substantial beads aggregations at the fluidic channel boundaries.

Example 2

Hydrophilic Coatings on the Ceiling and Sidewalls of the Flowcell Channel

This example demonstrates that having hydrophilic coatings on the ceiling and sidewalls of a flowcell channel can result in some reductions of bead aggregations at the fluidic channel boundaries with a horizontal non-tilting workflow, even though the differences in the contact angles between the ceiling and the sidewalls of the flowcell channel are smaller.

FIG. 11A shows an image of a microwell array. The microwell array is at the bottom of a flowcell. The fluidic channel of the flowcell is 4 mm in width. The ceiling and sidewalls of the fluidic channel of the flowcell has hydrophilic coatings on their surfaces. The regions of the microwell array labeled 1 and 9 correspond to the regions closer to the inlet and the outlet of the flowcell respectively. Having hydrophilic coatings on the ceiling and sidewall resulted in some incomplete gas displacement near the fluidic channel boundaries with a horizontal non-tilting workflow.

FIGS. 11B-11C are images showing that the percentages of the microwells of the microwell array with bead doublets were similar at the center and the boundary of the fluidic channel for the microwell array region 1 (which was closer to the inlet of the flowcell). FIGS. 11D-11E are images showing that the percentage of the microwells of the microwell array with bead doublets was lower at the center compared to the boundary of the fluidic channel for the microwell array region 9 (which was closer to the outlet of the flowcell).

FIGS. 11F-11I are plots showing the percentages of the microwells of the microwell array with no bead, single beads, or bead doublets along the flow direction. Having hydrophilic coatings on the ceiling and sidewalls of the fluidic channel resulted in some incomplete gas displacement near the fluidic channel boundaries with a horizontal non-tilting workflow. The effect of the incomplete gas displacement was more apparent at the fluidic channel boundaries towards the end of the fluidic channel, closer to region 9.

Altogether, these data demonstrate that some reductions in bead aggregations at the flowcell boundaries can be achieved without tilting the flowcell if the ceiling and sidewalls of the flowcell channel have small contact angles (for example, if the ceiling and sidewalls of the flowcell channel comprise a hydrophilic coating), even though the differences in the contact angles between the ceiling and the sidewalls of the flowcell channel are small. Thus, the flowcell can be used with a horizontal non-tilting workflow. However, the effect of incomplete gas displacement near the fluidic channel boundaries was more apparent at the fluidic channel boundaries towards the end of the fluidic channel.

Example 3

Further Reductions of Bead Aggregations at the Flowcell Boundaries

This example demonstrates that further reductions of bead aggregations at the flowcell boundaries can be achieved if the contact angle of the fluidic channel ceiling is smaller than the contact angles of flowcell sidewalls.

Figure 12A:
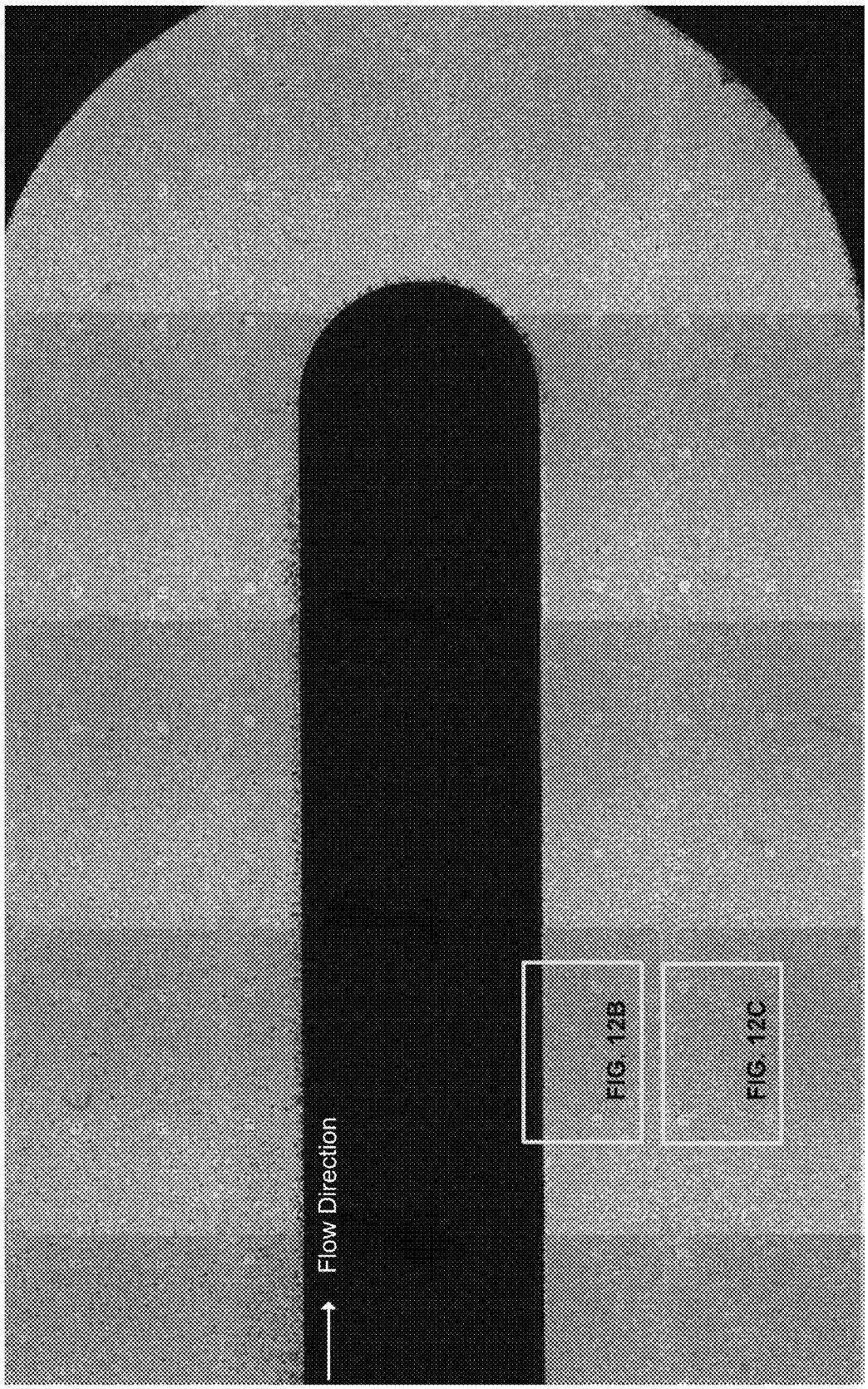
FIGS. 12A-12C are images of a microwell array showing that bead aggregations were significantly reduced at flowcell boundaries. The microwell array is at the bottom of a flowcell. The ceiling, but not sidewalls and bottom, of the fluidic channel of the flowcell had a hydrophilic coating. Bead aggregations were significantly reduced at the flowcell boundaries. Little spatial variation of bead loading uniformity or consistency was observed.
Figure 12B:
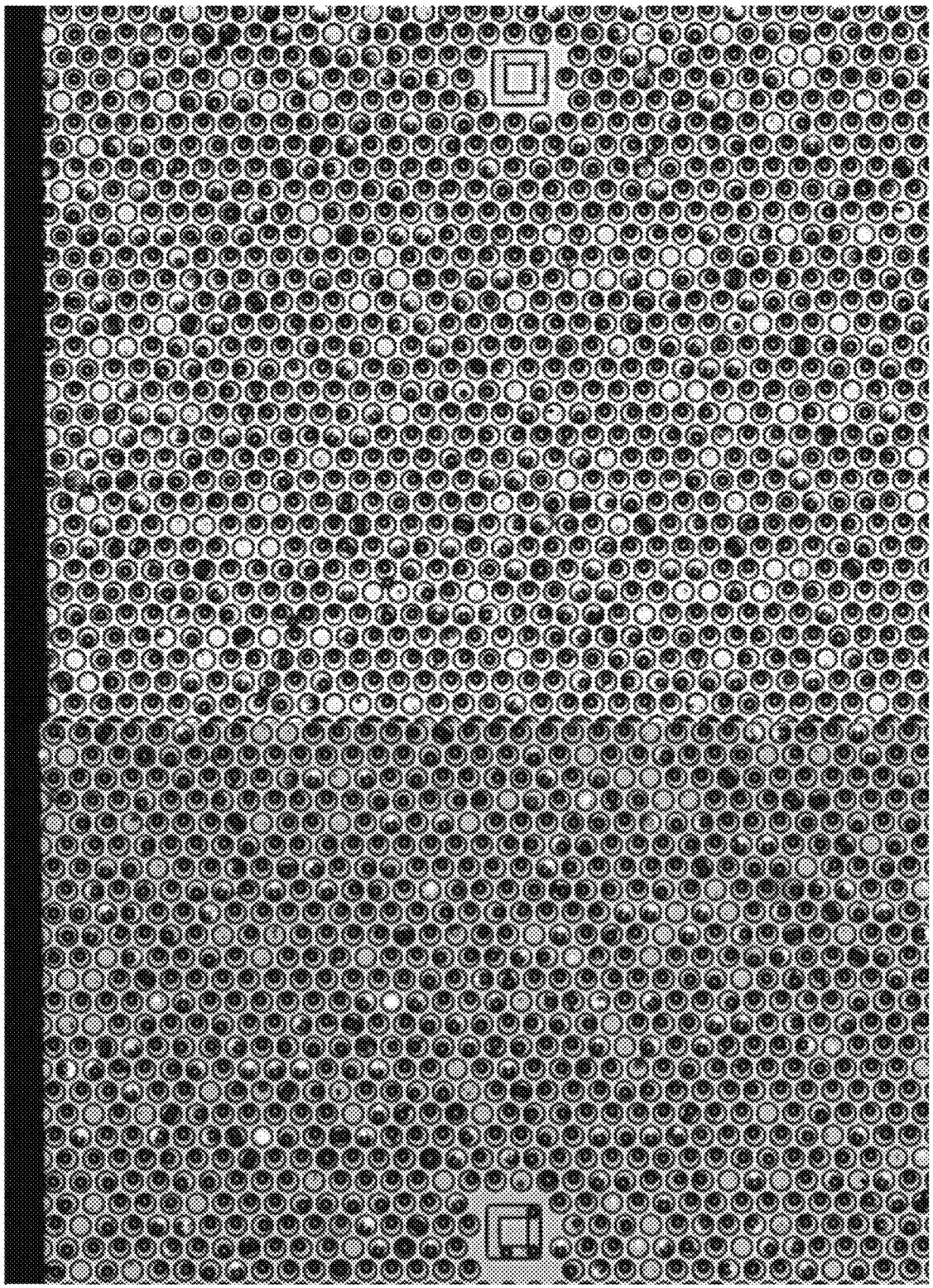
Figure 12C:
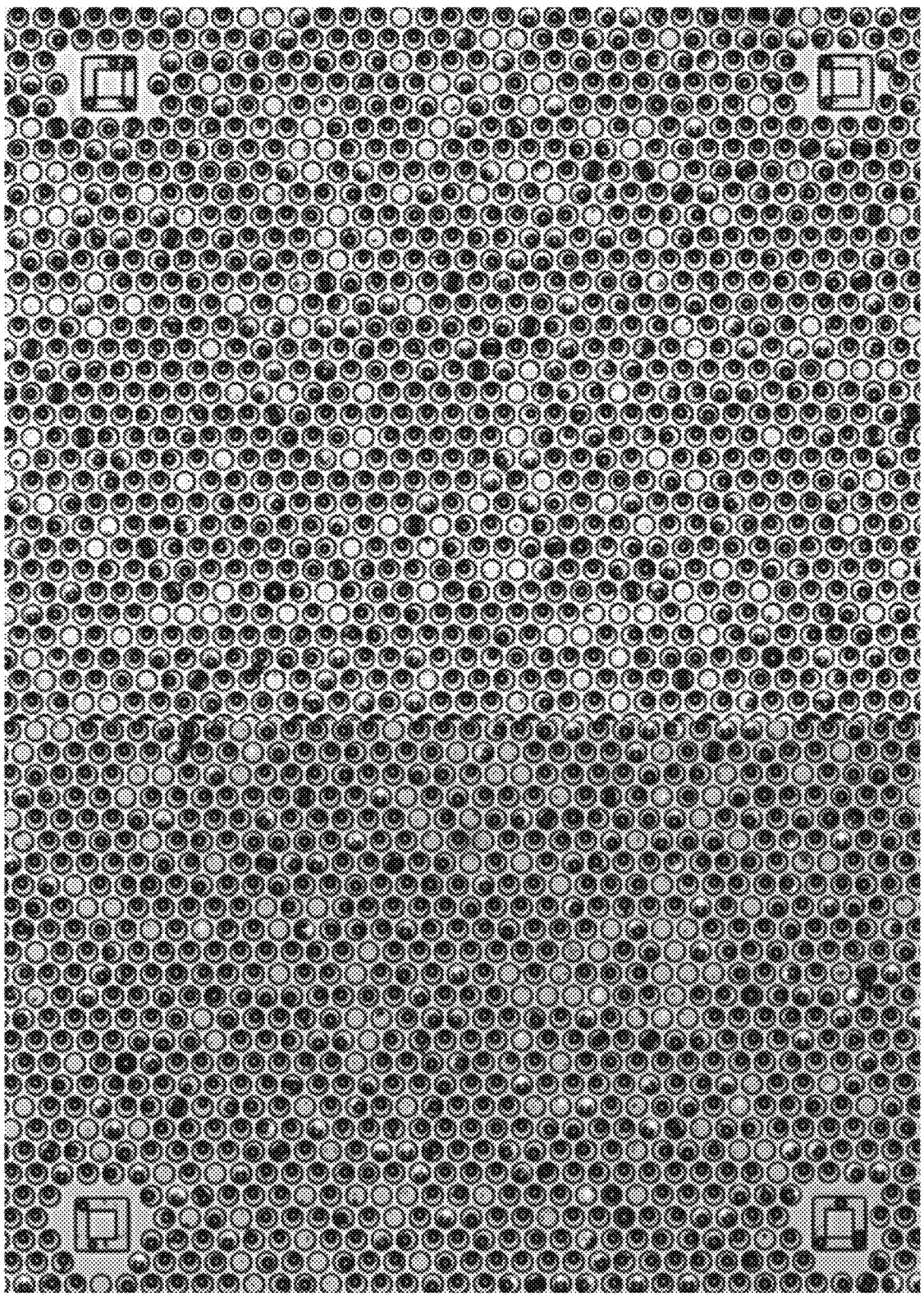

FIGS. 12A-12C are images of a microwell array showing that bead aggregations were significantly reduced at flowcell boundaries. The microwell array was at the bottom of a flowcell. The fluidic channel of the flowcell was 7 mm in width. The 7 mm width (compared to a 4 mm width) can increase the flowcell area of a given flowcell length. The ceiling, and not sidewalls, of the fluidic channel of the flowcell had a hydrophilic coating. Bead aggregations were further reduced at flowcell boundaries. Little spatial variation of bead loading uniformity or consistency was observed. Thus, the requirement to utilize buoyancy to displace gas with buffer or to displace buffer with gas, may be eliminated. In turn, the requirement of non-horizontal titling workflow of the flow-cell may be eliminated.

Altogether, these data demonstrate that further reductions of bead aggregations at the flowcell boundaries can be achieved without tilting the flowcell if the contact angle of the fluidic channel ceiling is smaller than the contact angles of the flowcell sidewalls (for example, if there is a hydrophilic coating on the ceiling, and not the sidewalls, of the flowcell channel). Thus, the flowcell can be used with a horizontal non-tilting workflow.

Example 4

Other Treatments of Fluidic Channel Surfaces

This example demonstrates properties of other treatments of fluidic channel surfaces.

Plasma treated cyclic olefin copolymers (COC) had good wetting characteristics, similar to those of $SiO_2$ coating. However, plasma treatment resulted in adhesion of beads to the surface, impacting ability to retrieve beads from the flowcell. Shelf-life for plasma treatment can variable and can require storage of flowcells in dry conditions. Selective plasma treatment through masking was non-trivial.

In comparison, PEG grafting to COC can provide a highly inert surface for reduced non-specific adsorption of oligonucleotides, cells, or beads. However, PEG grafting to COC was non-trivial.

Another surface treatment tested for coating the microwell substrate with $SiO_2$. Such coating resulted in good wetting characteristics and provided self-wetting of the microwells. However, the plug flow behavior changed. And agitation at the microwell surface was reduced, resulting in increased bead doublet density. Bead retrieval from the substrate was also negatively impacted.

All together, these data demonstrate that $SiO_2$ coating on the fluidic channel ceiling was advantageous for improved cell loading, bead loading, and bead retrieval compared to plasmas treatment, PEG grafting, and microwell surface $SiO_2$ coating.

Example 5

Further Reductions of Bead Aggregations at the Fluidic Channel Boundaries

This example demonstrates having the contact angle of the central portions of the fluidic channel ceiling being smaller than the contact angles of the non-central portions of the fluidic channel ceiling and the flowcell sidewalls can result in further reductions of bead aggregations at the flowcell boundaries.

FIGS. 13A1-13C2 are images of microwell arrays with a hydrophilic coating of silicon dioxide at the fluidic channel ceiling (FIGS. 13A1-13A2) or at the central portions of the fluidic channel ceiling (FIGS. 13B1-13C2), showing further reductions in bead aggregations at flowcell boundaries. The fluidic channels in FIGS. 13A1-13C2 were 7 mm in width. FIGS. 13A1-13A2 are images of a microwell array in a flowcell with a hydrophilic coating at the fluidic channel ceiling. Some bead aggregations were observed at the fluidic channel boundary. FIG. 13A1 shows that the orthogonal expansion of the fluid front, at the flowcell edges, resulted in ineffective washing of the beads near the flowcell edge.

To effectively flush away excess beads, the profile of the gas/buffer fluid front should have a component that is parallel rather than orthogonal to the flowcell edges. FIGS. 13B1-13C2 are images of microwell arrays in flowcells with hydrophilic coatings at the central portions of the fluidic channel ceilings that are offset from the fluidic channel boundaries by 500 micrometer and 1000 micrometer respectively. FIGS. 13B1-13C2 show the offsets at the fluidic channel ceiling improved the ability to flush away excess beads.

Altogether, these data demonstrate further reductions of bead aggregations at the flowcell boundaries can be achieved if the contact angle of the central portions of the fluidic channel ceiling is smaller than the contact angles of the non-central portions of the fluidic channel ceiling and the flowcell sidewalls (for example, by coating the central portions of the fluidic channel ceiling). Thus, the flowcell can be used with a horizontal non-tilting workflow.

Example 6

Consistent High Loading Efficiency

This example demonstrates consistent high loading efficiency when the contact angle of the central portion of the fluidic channel ceiling of a flowcell is smaller than the contact angles of the non-central portions of the fluidic channel ceiling and the flowcell sidewalls.

Figure 14A:
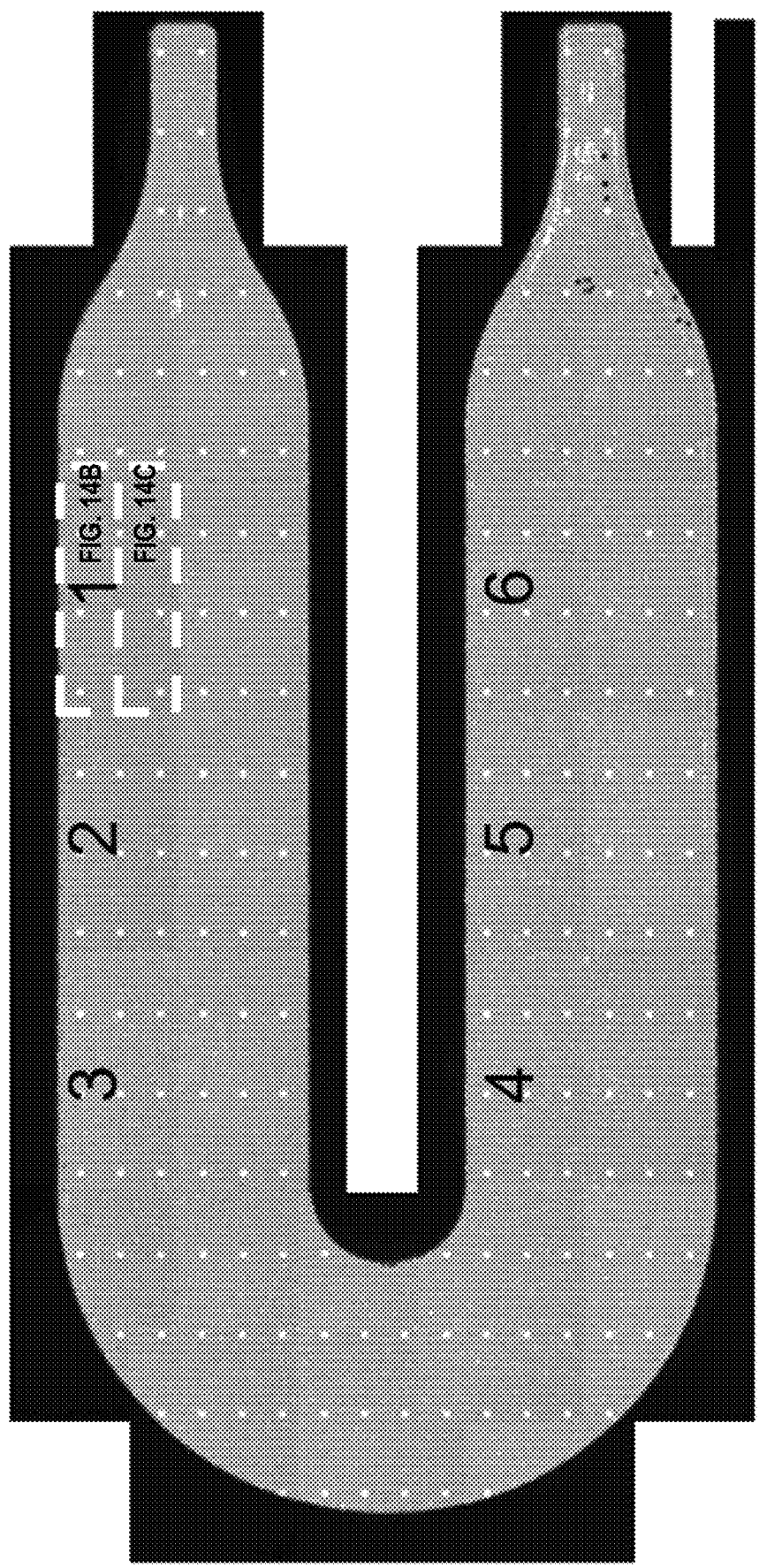

For each loading experiment, beads were loaded onto a microwell array of a U-shaped flowcell of a cartridge (FIG. 14A), and excess beads were washed away. The fluidic channel of the flowcell was 7 mm in width. To effectively flush away excess beads, the profile of the gas/buffer fluid front had a component that was parallel rather than orthogonal to the flowcell edges, which was achieved by the fluidic channel ceiling having a hydrophilic coating of silicon dioxide. The fluidic channel sidewalls and the fluidic channel bottom did not have a hydrophilic coating of silicon dioxide. Thus the contact angle of the central portion of the fluidic channel ceiling of a flowcell is smaller than the contact angles of the non-central portions of the fluidic channel ceiling and the flowcell sidewalls. The hydrophilic coating on the fluidic channel ceiling was offset from the edges form by the fluidic channel ceiling and fluidic channel sidewalls. Loading experiments were repeated 207 times.

Figure 14B:
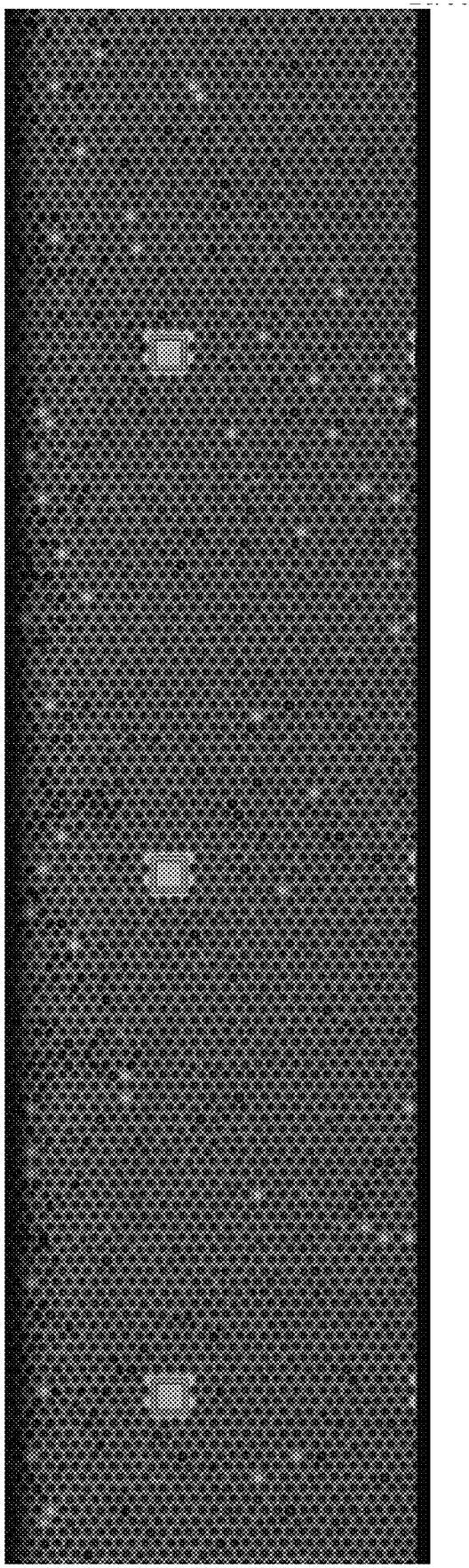
Figure 14C:
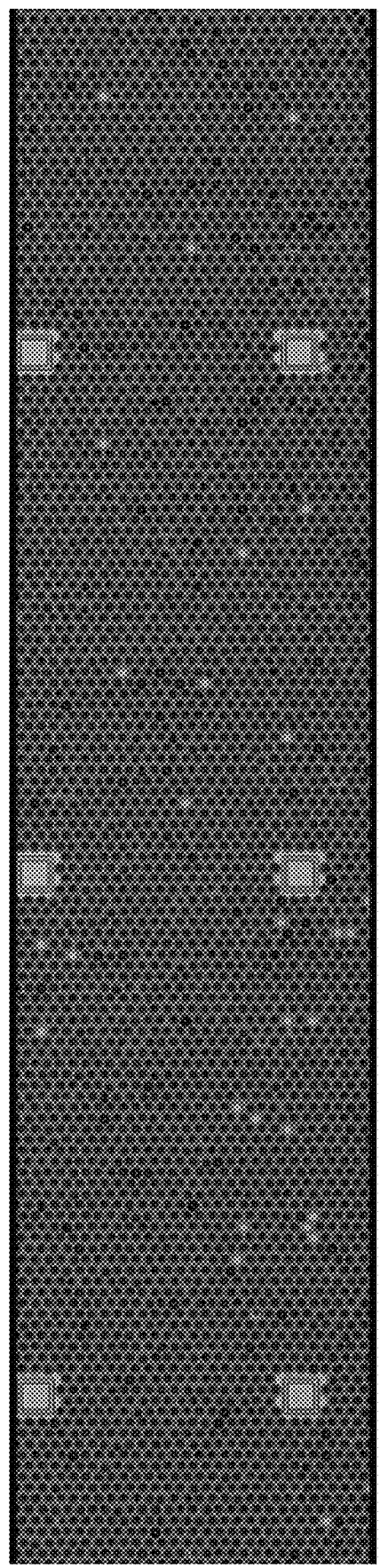

FIGS. 15A1-15J2 are images of microwell arrays of flowcells for 10 of the 207 loading experiments. The 10 loading experiments show that good loading efficiency can be achieved with a hydrophilic coating of silicon dioxide at the central portion of the flowcell ceiling (FIGS. 14B, 14C, 15A1-15J2). Table 1 is a summary of the loading efficiency of the 10 loading experiments. The loading experiments also show minimal bead aggregation at the flowcell boundaries and little variation of bead loading uniformity or consistency were achieved (FIGS. 14D-14G, 15A1-15J2). FIGS. 14B-14C are images from one of the loading experiment showing that the percentages of the microwells of the microwell array with bead doublets were similar at the center and the boundary of the fluidic channel for the microwell array. FIGS. 14D-14G are plots for two loading experiments showing no edge effect with respect to the percentages of the microwells of the microwell array with no bead, single beads, or bead doublets along the flow direction.

TABLE 1

| Loading efficiency of 10 loading experiments. After bead wash, % wells with beads |
|---|
| 91.2 |
| 95.1 |
| 95.3 |
| 96.1 |
| 93.7 |
| 96.5 |
| 95.4 |
| 93.7 |
| 95.6 |
| 96.0 |

TABLE 2

Loading efficiency of 207 loading experiments.
After bead wash, % wells with beads

| | | | | | | | | | |
|---|---|---|---|---|---|---|---|---|---|
| 91.18 | 94.85 | 95.49 | 96.43 | 94.06 | 94.31 | 93.31 | 95.73 | 96.54 | 95.93 |
| 92.98 | 93.59 | 96.26 | 95.90 | 96.24 | 93.68 | 90.02 | 96.39 | 96.66 | 95.78 |

TABLE 2-continued

Loading efficiency of 207 loading experiments.
After bead wash, % wells with beads

| | | | | | | | | | |
|---|---|---|---|---|---|---|---|---|---|
| 90.67 | 93.30 | 94.93 | 95.39 | 95.30 | 93.59 | 94.15 | 95.92 | 92.40 | 94.01 |
| 92.94 | 93.22 | 95.11 | 94.48 | 95.31 | 94.85 | 95.11 | 97.16 | 95.73 | 94.42 |
| 95.99 | 94.30 | 94.78 | 95.41 | 95.21 | 96.15 | 93.50 | 96.71 | 96.98 | 95.87 |
| 89.70 | 93.30 | 95.05 | 95.20 | 95.53 | 94.60 | 94.35 | 97.08 | 97.06 | 95.63 |
| 92.88 | 93.94 | 95.85 | 95.29 | 95.44 | 94.10 | 95.22 | 94.03 | 96.73 | 92.43 |
| 96.20 | 94.55 | 96.47 | 94.90 | 96.08 | 91.17 | 95.41 | 95.90 | 96.58 | 94.09 |
| 95.74 | 93.72 | 96.33 | 91.69 | 95.75 | 95.24 | 95.67 | 95.97 | 95.99 | 95.15 |
| 95.71 | 94.76 | 96.11 | 92.09 | 95.83 | 95.08 | 95.08 | 96.14 | 95.74 | 96.31 |
| 95.93 | 94.31 | 94.98 | 92.07 | 96.69 | 93.15 | 92.55 | 90.45 | 94.67 | 95.15 |
| 96.23 | 94.46 | 92.89 | 94.57 | 95.43 | 95.41 | 93.56 | 94.73 | 95.97 | 96.20 |
| 95.77 | 94.11 | 93.80 | 92.54 | 95.86 | 94.63 | 94.25 | 95.63 | 95.30 | 94.76 |
| 95.91 | 95.01 | 95.00 | 92.82 | 96.79 | 96.39 | 93.73 | 94.12 | 96.97 | 94.90 |
| 95.42 | 95.02 | 96.08 | 89.10 | 96.51 | 96.37 | 91.14 | 95.37 | 96.58 | 94.88 |
| 96.34 | 94.74 | 95.67 | 92.89 | 96.49 | 96.49 | 91.63 | 89.97 | 96.67 | 91.79 |
| 95.34 | 94.64 | 95.81 | 93.70 | 85.25 | 95.75 | 95.79 | 94.58 | 96.56 | 95.70 |
| 94.60 | 95.15 | 96.10 | 90.24 | 95.22 | 96.00 | 96.68 | 95.24 | 96.51 | |
| 94.97 | 95.27 | 92.75 | 94.16 | 94.82 | 95.65 | 96.45 | 94.99 | 96.91 | |
| 95.05 | 91.38 | 95.88 | 94.16 | 94.35 | 96.47 | 96.21 | 94.84 | 95.98 | |
| 94.14 | 93.46 | 95.71 | 92.84 | 95.48 | 92.28 | 96.51 | 96.44 | 95.98 | |

Figure 16B:
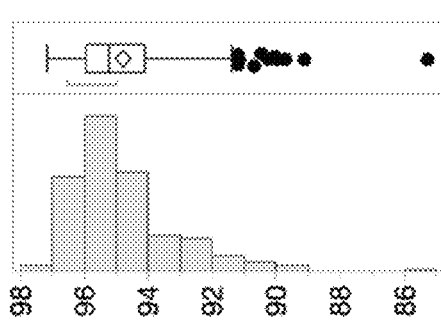
Figure 16A:
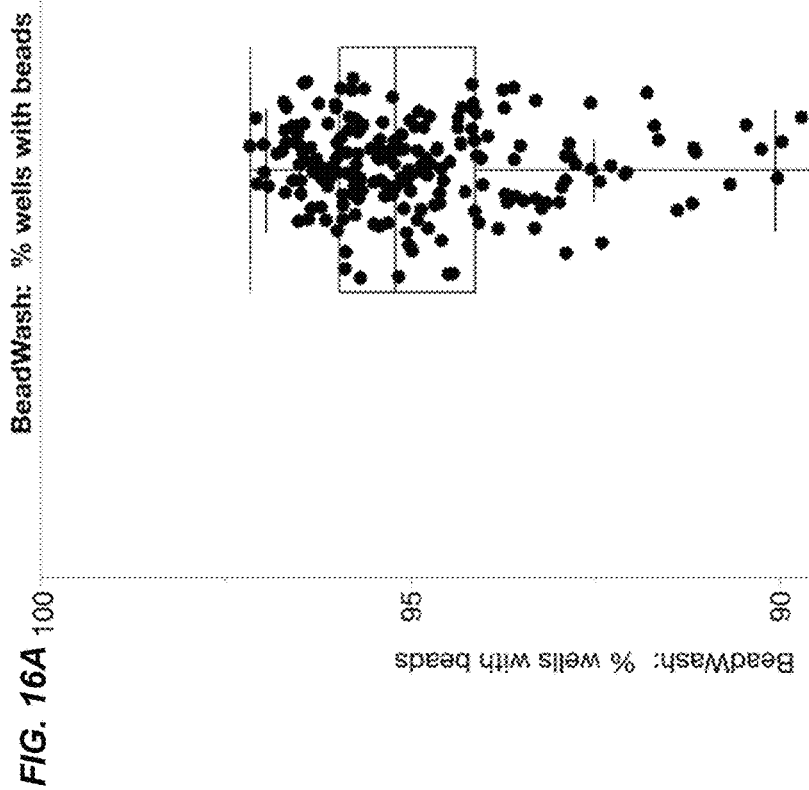

FIGS. 16A-16D shows the consistent high loading efficiency of the 207 loading experiments. FIG. 16A is a plot showing the loading efficiency for the 207 loading experiments. FIG. 16B is a bar chart showing consistent, high loading efficiency for the 207 loading experiments. FIGS. 16C and 16D are tables summarizing the statistics of the 207 loading experiments. Table 2 is a summary of the loading efficiency of the 207 loading experiments.

Altogether, these data demonstrate that consistent high loading efficiency, minimal bead aggregation at flowcell boundaries, and little variation of bead loading uniformity or consistency can be achieved when the contact angle of the central portion of the fluidic channel ceiling of a flowcell is smaller than the contact angles of the non-central portions of the fluidic channel ceiling and the flowcell sidewalls.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
   a flowcell comprising a fluidic channel, an inlet port, and an outlet port,
   wherein the fluidic channel comprises a ceiling, a first sidewall, and a bottom, wherein the ceiling and the first sidewall form a ceiling-first sidewall edge, and wherein the bottom and the first sidewall form a bottom-first sidewall edge,
   wherein the ceiling comprises a central portion that is offset from the ceiling-first sidewall edge, thereby forming an offset from the ceiling-first sidewall edge,
   wherein the central portion is more hydrophilic than the offset,
   wherein the bottom of the fluidic channel comprises a substrate which comprises a plurality of microwells, and
   wherein the inlet port and the outlet port are in fluid communication with the flowcell via the fluidic channel.

2. The device of claim 1, wherein the fluidic channel has a non-circular cross section.

3. The device of claim 1, wherein the fluidic channel comprises a second sidewall, wherein the ceiling and the second sidewall form a ceiling-second sidewall edge, and wherein the bottom and the second sidewall for a bottom-second sidewall edge.

4. The device of claim 1, wherein the fluidic channel has a width of at least 2 mm.

5. The device of claim 1, wherein the fluidic channel is at least 0.8 mm in height.

6. The device of claim 1, wherein the first sidewall has a positive draft angle of 1-15 degrees.

7. The device of claim 1, wherein the flowcell comprises silicon, fused-silica, glass, polydimethylsiloxane (PDMS), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resin, metal, or a combination thereof.

8. The device of claim 1, wherein the ceiling is hydrophilic.

9. The device of claim 1, wherein the contact angle of the ceiling is 0-80 degrees.

10. The device of claim 1, wherein the contact angle of the first sidewall is about 88 degrees.

11. The device of claim 1, wherein the contact angle of the ceiling is sufficiently smaller than the contact angle of the first sidewall to enable non-laminar flow within the fluidic channel.

12. The device of claim 11, wherein the non-laminar flow within the fluidic channel enables agitation of a particle on the surface of the substrate by a flow within the fluidic channel, and wherein a speed of the flow at a boundary between the flow and the bottom is non-zero.

13. The device of claim 11, wherein the non-laminar flow is approximately plug flow, and wherein the relative flow velocity of a flow across a cross section of the fluidic channel is approximately constant.

14. The device of claim 11, wherein the non-laminar flow is plug flow, and wherein the relative flow velocity of a flow across a cross section of the fluidic channel is constant.

15. The device of claim 14, wherein the plug flow is approximately horizontal plug flow.

16. The device of claim 15, wherein the horizontal plug flow is capillary aided horizontal plug flow.

17. The device of claim 14, wherein the plug flow does not depend on buoyancy of a gas, or wherein the plug flow does not depend on tilting of the device.

18. The device of claim 14, wherein the plug flow is at a buffer-gas interface.

19. The device of claim 1, wherein the ceiling comprises a hydrophilic coating having a contact angle.

20. The device of claim 19, wherein the hydrophilic coating comprises polyethylene glycol (PEG), poly-Hema, pluronic acid F68, pluronic acid F108, pluronic acid F127, polysorbate 20, silicon dioxide ($SiO_2$), silicon nitride, or any combination thereof.

21. The device of claim 20, wherein the hydrophilic coating comprises silicon dioxide ($SiO_2$), silicon nitride, or any combination thereof.

22. The device of claim 19, wherein the contact angle of the hydrophilic coating is at most 23 degrees.

23. The device of claim 19, wherein the ceiling is coated with the hydrophilic coating by sputtering, thermal growth, adsorption, covalent binding, or any combination thereof.

24. The device of claim 19, wherein the hydrophilic coating is offset from the ceiling-first sidewall edge.

25. The device of claim 24, wherein the hydrophilic coating is offset from the ceiling-first sidewall edge by 100-1000 micrometers.

26. The device of claim 24, wherein the hydrophilic coating is offset from the ceiling-first sidewall edge by 1%-25% of the width of the ceiling.

27. The device of claim 1, comprising a plurality of particles residing in the plurality of microwells of the substrate, and wherein at least 25% of the plurality of microwells each contains a single particle.

28. A method for sample loading, comprising
   (a) providing a device that comprises:
   a flowcell comprising a fluidic channel, an inlet port, and an outlet port,
      wherein the fluidic channel comprises a ceiling a first sidewall, and a bottom, wherein the ceiling and the first sidewall forms a ceiling-first sidewall edge, and wherein the bottom and the first sidewall forms a bottom-first sidewall edge,
      wherein the ceiling comprises a central portion that is offset from the ceiling-first sidewall edge, thereby forming an offset from the ceiling-first sidewall edge,
      wherein the central portion is more hydrophilic than the offset,
      wherein the bottom comprises a substrate which comprises a plurality of microwells, and
      wherein the inlet port and the outlet port are in fluid communication with the flowcell via the fluidic channel;
   (b) introducing a gas into the fluidic channel via the inlet port; and
   (c) introducing a first sample comprising a first plurality of particles into the fluidic channel via the inlet port, whereby at least 25% of the plurality of microwells each contains a single particle of the first plurality of particles.

29. The method of claim 28, comprising:
(d) introducing the gas or another gas into the fluidic channel via the inlet port after step (c); and
(e) introducing a second sample into the fluidic channel via the inlet port after introducing the first sample into the fluidic channel,
wherein the second sample comprises a second plurality of particles, and
whereby at least 25% of the plurality of microwells each contains a single particle of the second plurality of particles.

30. The method of claim 29, comprising:
prior to introducing the gas into the fluidic channel via the inlet port in (d), introducing a first buffer into the fluidic channel via the inlet port to remove the first plurality of particles that are on the bottom and are not contained in any of the plurality of microwells, or
after introducing the second sample into the fluidic channel via the inlet port in (e), introducing a second buffer into the fluidic channel via the inlet port to remove the second plurality of particles that are on the bottom and are not contained in any of the plurality of microwells.

* * * * *